United States Patent
Rang (12)

(10) Patent No.: US 6,551,623 B1
(45) Date of Patent: Apr. 22, 2003

(54) IMMUNOMODULATING COMPOSITIONS FROM BILE

(75) Inventor: Romeo Rang, Bucharest (RO)

(73) Assignee: Lorus Therapeutics Inc., Toronto (CA)

( * ) Notice: Subject to any disclaimer, the term of this patent is extended or adjusted under 35 U.S.C. 154(b) by 0 days.

(21) Appl. No.: 09/479,835

(22) Filed: Jan. 7, 2000

Related U.S. Application Data

(63) Continuation of application No. 08/612,921, filed as application No. PCT/CA94/00494 on Sep. 9, 1994, now Pat. No. 6,280,774.

(51) Int. Cl.$^7$ ............................................. A61K 35/413
(52) U.S. Cl. ...................................................... 424/528
(58) Field of Search ........................................ 424/528

(56) References Cited

U.S. PATENT DOCUMENTS

| | | | |
|---|---|---|---|
| 4,372,949 A | 2/1983 | Kodama et al. | 514/78 |
| 4,562,179 A | 12/1985 | Teraji et al. | 514/77 |
| 4,585,762 A | 4/1986 | Teraji et al. | 514/129 |
| 4,767,610 A | 8/1988 | Long | 424/9.4 |
| 4,837,023 A | 6/1989 | Eibl | 424/439 |
| 4,879,226 A | 11/1989 | Wallace et al. | 435/68.1 |
| 4,900,724 A | 2/1990 | Kato et al. | 514/62 |
| 4,916,249 A | 4/1990 | Brachwitz et al. | 558/169 |
| 4,935,520 A | 6/1990 | Nojima et al. | 546/22 |
| 4,965,391 A | 10/1990 | Counsell et al. | 558/169 |
| 5,049,552 A | 9/1991 | Eibl | 514/77 |
| 5,081,245 A | 1/1992 | Nomura et al. | 514/316 |
| 5,087,721 A | 2/1992 | Counsell et al. | 558/166 |
| 5,103,007 A | 4/1992 | Nomura et al. | 544/316 |
| 5,118,674 A | 6/1992 | Braquet et al. | 514/77 |
| 5,138,067 A | 8/1992 | Kamata et al. | 548/204 |
| 5,310,958 A | 5/1994 | Mizushima | 554/41 |
| 5,369,097 A | 11/1994 | Salari et al. | 514/77 |

FOREIGN PATENT DOCUMENTS

| | | |
|---|---|---|
| EP | 0285285 | 10/1988 |
| GB | 337797 | 12/1930 |
| WO | WO 89/06977 | 8/1989 |
| WO | WO 90/12583 | 11/1990 |

OTHER PUBLICATIONS

Ren Yun-fang, et al., "The effects of swine bile acids—sodium salt on the inhibition of proliferation and induction of differentiation in human promyelocytic leukemia cell line HL-60," Chinese Journal of Pharmacology and Toxicology, vol. 3[3], (1989), pp. 236-240.

Watanabe et al., "Antitumor Effect of Tumor Necrosis Factor Against Various Types of Human Cancer Cells," Jpn J. Cancer Chemother., vol. 12[11], 1985, pp. 2185-2189.

Bandurski et al., (1951), "The Chromatographic Identification of Some Biologically Important Phosphate Esters," J. Biol. Chem., 193: pp. 405-410.

Greve et al., (Oct. 1989) "Bile Acids Inhibit Endotoxin-Induced Release of Tumor Necrosis Factor by Monocytes: An in vitro Study," Hepatology, vol. 10, No. 4, pp. 454-458.

Larsen et al., (1981), "Improved Thin-Layer Chromatographic Assay for Monitoring Lecithin/Sphingomyelin Ratios in Amniotic Fluid," J. Chroma., 226: pp. 484-487.

Munder et al., (1981), "Alkyllysophospholipids in Cancer Therapy," Augmenting Agents in Cancer Therapy, pp. 441-458.

Rigler et al., (1983), "Rapid Quantification of Chromarods of Cholesterol, Total Bile Salts and Phospholipids from the Same Micoliter Sample of Human Gallbladder Bile," Journal of Chromatography, 277, pp. 321-327.

Sundaram et al., (1971), "Thin-Layer Chromatographic Separation of Chenodeoxycholic and Deoxycholic Acids.", Cli. Chem. Acata., 34: pp. 425-429.

Tamari et al., (1976), "Etudes sur les Phosphonolipides de la Bile de Bouef," Agr. Biol. Chem., 40: pp. 2057-2062.

Braun, et al. "The in vitro Development of Cytotoxicity in Response to Granulocyte/Macrophage-colony-stimulating Factor or Interferon Y in the Peripheral Blood Monocytes of Patients with Solid Tumors: Modulation by Arachidonic Acid Metabolic Inhibitors" Cancer Immunol. Immunother. (1990), vol. 32, pp. 55-61.

Braun, et al. "Sensitivity of Tumoricidal Functrion in Macrophages from Different Anatomical Sites of Cancer Patients to Modulation of Arachidonic Acid Metabolism" Cancer Research (1993), vol. 53, pp. 3362-3368.

Grewal, et al., "Induction of Tumor Necrosis Factor in Severe Acute Pancreatitis and its Subsequent Reduction after Hepatic Passage" Surgery (1994), vol. 115, pp. 213-221.

Kabuta, et al., "The Prevention and Therapy By Simian Liver Extract and Bovine Gallbladder Bile Against Herpes Simplex Virus Infected Mice," J. Kuruma Med. Assoc., vol. 48, No. 6, pp. 443-448.

Miller, et al., "Reporting Results of Cancer Treatment" Cancer (1981), vol. 47, pp. 207-214.

(List continued on next page.)

Primary Examiner—Jean C. Witz
(74) Attorney, Agent, or Firm—Gary M. Nath; Todd L. Juneau; Joshua B. Goldberg

(57) ABSTRACT

The present invention relates to a composition for use as an immunomodulator comprising small molecular weight components of less than 3000 daltons, and having the following properties: a) is extractable from bile of animals; b) is capable of stimulating monocytes and macrophages in vitro; c) is capable of modulating tumor necrosis factor production; d) contains no measurable IL-1a, IL-1b, TNF, IL-6, IL-8, IL-4, GM-CSF or IFN-gamma; e) has an antiproliferative effect in a malignant mouse hybridoma cell line; f) shows no cytotoxicity to human peripheral blood mononuclear cells; and g) is not an endotoxin. The invention also relates to a method of preparing the composition and its use as an immunomodulator.

20 Claims, 21 Drawing Sheets

OTHER PUBLICATIONS

Ren, et al., *Chinese J. of Pharm. and Toxic.*, vol. 3, No. 3, pp. 236–240.

Shinoda, et al., "Purification of a Leukocytosis Promotion-inhibiting Factor from Bovine Bile" *Chem. Pharm. Bull.* (1982), vol. 30, pp. 4429–4434.

Smith, et al., "Measurement of Protein Using Bicinchoninic Acid" *Anal. Biochem.* (1985), vol. 150, pp. 76–85.

Szabo, et al., "Regulatory Potential of Ethanol and Retinoic Acid on Human Monocyte Functions" *Alcohol Clin. Res.* (1994), vol. 18(3), pp. 548–552.

Taber's Cyclopedic Medical Dictionary, 15th Edition (1986) (F.A. Davis: Philadelphia, PA) p. 195–6 and 1481.

Thirwell, et al., "Phase I–II Trial of an Unconventional Agent Virulizin in Patients with Advanced Cancer" *J. Cancer Res. Clin. Oncol.* Suppl., vol. 116(1), pp. 51 (abstract A1.240.01).

Warner, et al., "A Phase II Study of Virulizin in Patients with Pancreatic Cancer" *Clin Invest Medicine*, Suppl. (1992), vol. 15(4), pp. A89 (abstract 546).

Warner, et al, "A Phase II Study of Virulizin in Patients with Pancreatic Cancer" *Clin. Invest. Medicine*, Suppl. (1994), vol. 17(1), pp. 37–41.

Watanabe, et al., "Antitumor Effect of the Tumor Necrosis Factor Against Various Types of Human Cancer Cell" *Jap. J. Cancer. Chemother.* (1985), vol. 12(11), pp. 2158–9 (abstract only).

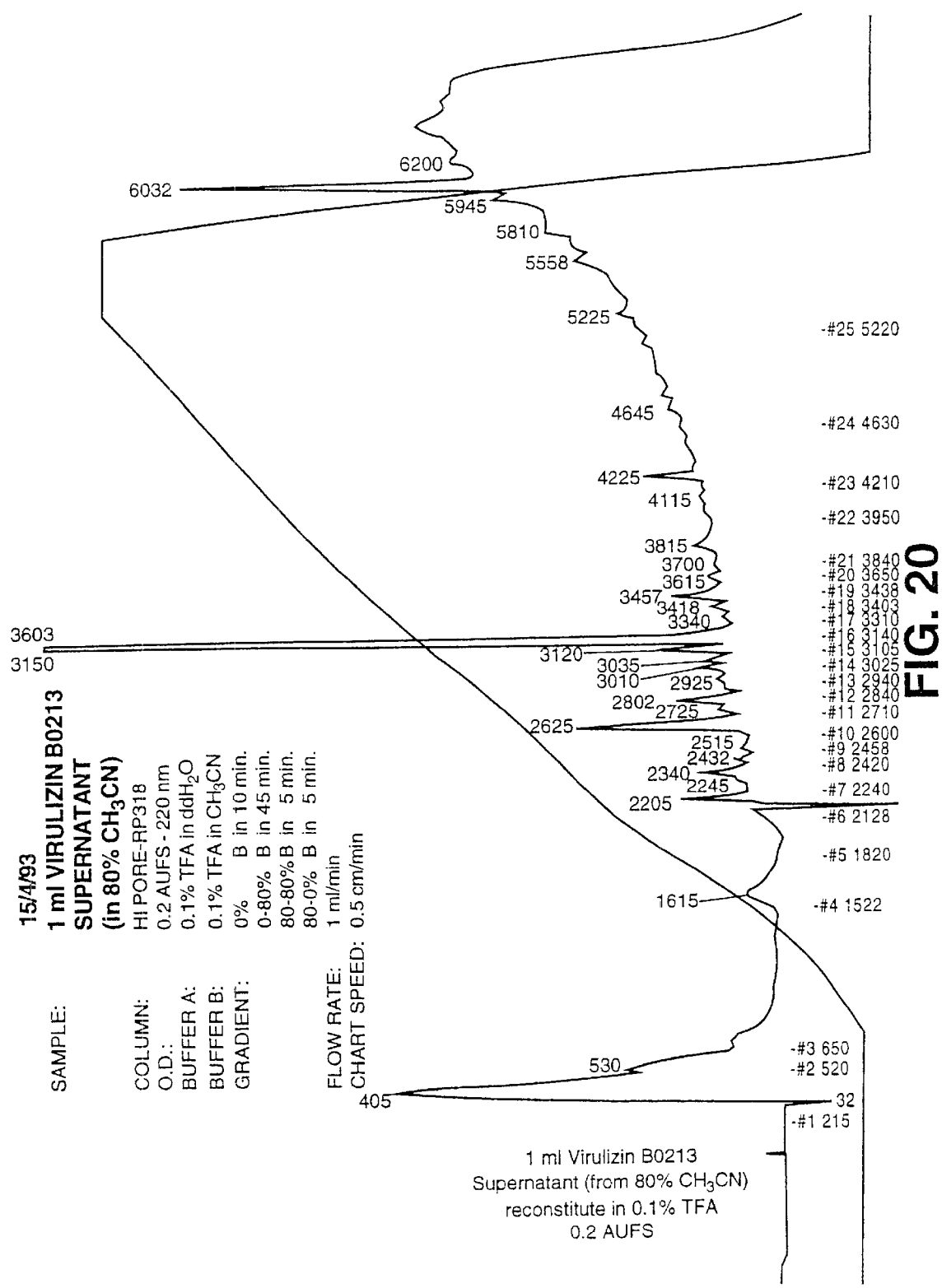

HYDROPHILIC COLUMN

Date:            14 Sept. 1993

COLUMN:          HYDROXYETHYL
BUFFER:          50mM Formic
FLOW RATE:       1ml/min
O.D.:            254 nm
CHART SPEED:     0.5 cm/min

| Time (min) | Substance | Peak Height (inch) |
|---|---|---|
| | Virulizin B0213 | |
| 6.32 | | 8.00 |
| 8.22 | | 2.60 |
| 9.07 | whole | 10.00 |
| 10.30 | | 0.70 |
| 13.25 | | 0.90 |
| 6.58 | | 10.00 |
| 8.29 | supernatant | 1.00 |
| 10.00 | | 0.55 |
| 13.40 | | 0.60 |
| 6.38 | precipitate | 3.50 |
| 8.23 | | 0.25 |

FIG. 21A

IMMUNOMODULATING COMPOSITIONS FROM BILE

This application is a con. of Ser. No. 08/612,921, filed May 16, 1996 which is a 371 of PCT/CA94/00494 filed Sep. 9, 1994, which claims priority to Ser. Nos. 08/118,269, filed Sep. 9, 1993, abandoned, 08/155,303, filed Nov. 22, 1993, abandoned, and 08/231,726, filed Apr. 22, 1994, abandoned.

FIELD OF THE INVENTION

The present invention relates to immunomodulating compositions, pharmaceutical agents containing the compositions, and the use of the compositions and agents in the treatment of animals.

BACKGROUND OF THE INVENTION

Therapies are continuously being developed for the prophylaxis and treatment of cancer and infectious diseases, such as Acquired Immunodeficiency Syndrome (AIDS). Some of these therapies attempt to use the immune system therapeutically. One approach is based on the antigen specific elements of the immune system, namely antibodies and T cells. For example, research has been aimed at developing vaccines against foreign agents, or against certain endogenous chemical messengers, such as interleukins, to suppress antibody reactions. A second approach is based on the isolation, cloning, expression and production of peptides and proteins from the non-antigen specific parts of the immune system. For example, proteins, such as cytokines, which comprise the interleukins produced by white blood cells, and interferons which stimulate lymphocytes and scavengers cells that digest foreign antigens, offer possibilities for therapies.

The treatment of cancer could be greatly enhanced if the early immune response to a tumor could be augmented so that the tumor does not reach a critical size. Strategies which have been suggested to augment the immune response to a tumor include vaccines specific for tumor-associated antigens; the use of monoclonal antibodies against antigens on the surface of tumor cells such as against the interleukin-2 receptor; the use of bispecific molecules containing antitumor antibodies and superantigens.

Relatively recently, the role of the physiologically active polypeptide, known as tumor necrosis factor ("TNF") has been studied, particularly with respect to its ability to induce necrosis of tumors, with no effect upon the normal tissues of the living body. The amino acid sequence of TNF, as well as the base sequence of the DNA coding for TNF has been disclosed in U.S. Pat. No. 4,879,226.

Because TNF has been shown to have a role in inducing necrosis of tumors, any agent that can stimulate the production or bioavailability of TNF in vivo has potential utility as a treatment for various tumorous conditions. Additionally, any agent that can stimulate human monocytes and macrophages to produce TNF in vitro, is useful as a means for providing a source of TNF for therapeutic administration, as well as for analytical and diagnostic purposes.

Bile, which is secreted by the liver and stored in the gall bladder, has been investigated for various purposes, including the use of bile extracts to enhance bioavailability of drugs that are readily metabolized by normal liver function (see WO 90/12583) and to inhibit leucocytosis promotion in a mammal (see Shinoda et al., Chem. Pharm. Bull., 30, 4429–4434 (1982)). However, bile has never been considered to be a source of therapeutically useful compositions with respect to neoplastic or infectious diseases. Interestingly, in accordance with British Patent No. 337,797, it was suggested to use the gall bladder itself as a potential source of anti-cancer agents, but only after the bile had been removed from the gall bladder, and the gall bladder thoroughly washed.

SUMMARY OF THE INVENTION

It has now been discovered that bile is an important source of a composition that can stimulate TNF production both in vitro and in vivo and is effective in treating various carcinomas, especially pancreatic cancer.

The bile composition of use is obtained by extraction of bile with a water soluble or miscible solvent. The extract so obtained may be further processed to remove unnecessary or undesirable components therefrom.

The product obtained by the process of extracting bile disclosed in further detail hereinbelow has been found to have TNF stimulating activity and is believed to have anti-cancer activity, especially against pancreatic and other cancers. Obviously, the entire composition so obtained may not be necessary to obtain such activity. Accordingly, it is possible to further separate, fractionate, or otherwise process the product thus obtained, and still retain the desired TNF stimulatory and anti-cancer activity. Moreover, it is envisioned that it is possible to obtain synthetically a product with the same or similar TNF stimulatory and anti-cancer activity. Thus, it is envisioned that the components of the product may be analyzed as to the components, or combination thereof, that are responsible for the desired activity, and a synthetic product made, based on such analysis.

In one aspect, the present invention relates to a composition for use as an immunomodulator comprising small molecular weight components of less than 3000 daltons, and having one or more of the following properties:

a) is extractable from bile of animals;

b) is capable of stimulating monocytes and macrophages in vitro;

c) is capable of modulating tumor necrosis factor production;

d) contains no measurable level of IL-1$\alpha$, IL-1$\beta$, TNF, IL-6, IL-8, IL-4, GN-CSF or IFN-gamma;

e) has an anti-proliferative effect in a malignant mouse hybridoma cell line;

f) shows no cytotoxicity to human peripheral blood mononuclear cells; and g) is not an endotoxin.

In accordance with a preferred embodiment the composition is extracted from the bile of bovines and is capable of stimulating the release of tumor necrosis factor.

The composition of the invention may be prepared by (a) mixing bile from an animal, preferably a bovine, with a solvent that is soluble or miscible with water, preferably an alcohol, and preferably with an equal volume of an alcohol, to produce a bile/alcohol solution; (b) separating the solution which preferably is an alcohol soluble fraction, and isolating therefrom a solution substantially free of alcohol, as by removing most of the alcohol, such as by the use of heat; (c) removing bile pigments from the solution to obtain a colorless liquid; (d) optionally treating the colorless liquid to substantially remove any residual alcohol; (e) removing fatty organic materials, as by extracting the colorless liquid with ether and isolating the aqueous phase; and (f) optionally removing residual ether from the aqueous phase.

The composition may be used without further modification by simply packaging it in vials and sterilizing. The composition may be also be used in a concentrated form. A preferred concentrated form is prepared as follows. Prior to step (e) the colorless liquid may optionally be concentrated to about one eighth of the volume of the bile/alcohol solution and after step (f) the aqueous phase may be concentrated so that it is one tenth of the volume of the bile/ethanol solution.

The invention also relates to a pharmaceutical agent comprising the novel composition of the invention.

The invention further relates to a method of treating a patient comprising administering to said patient an effective amount of a composition of the invention. The invention still further relates to the use of a composition of the invention in the prophylaxis and treatment of diseases and conditions requiring modulation of the immune response; preferably infectious diseases and neoplasias.

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

Further details of the invention are described below with the help of the examples illustrated in the accompanying drawings in which:

FIG. 20 is a graph showing the RP-HPLC profile of a supernatant of the composition of the invention;

DETAILED DESCRIPTION OF THE INVENTION

Figure 1:
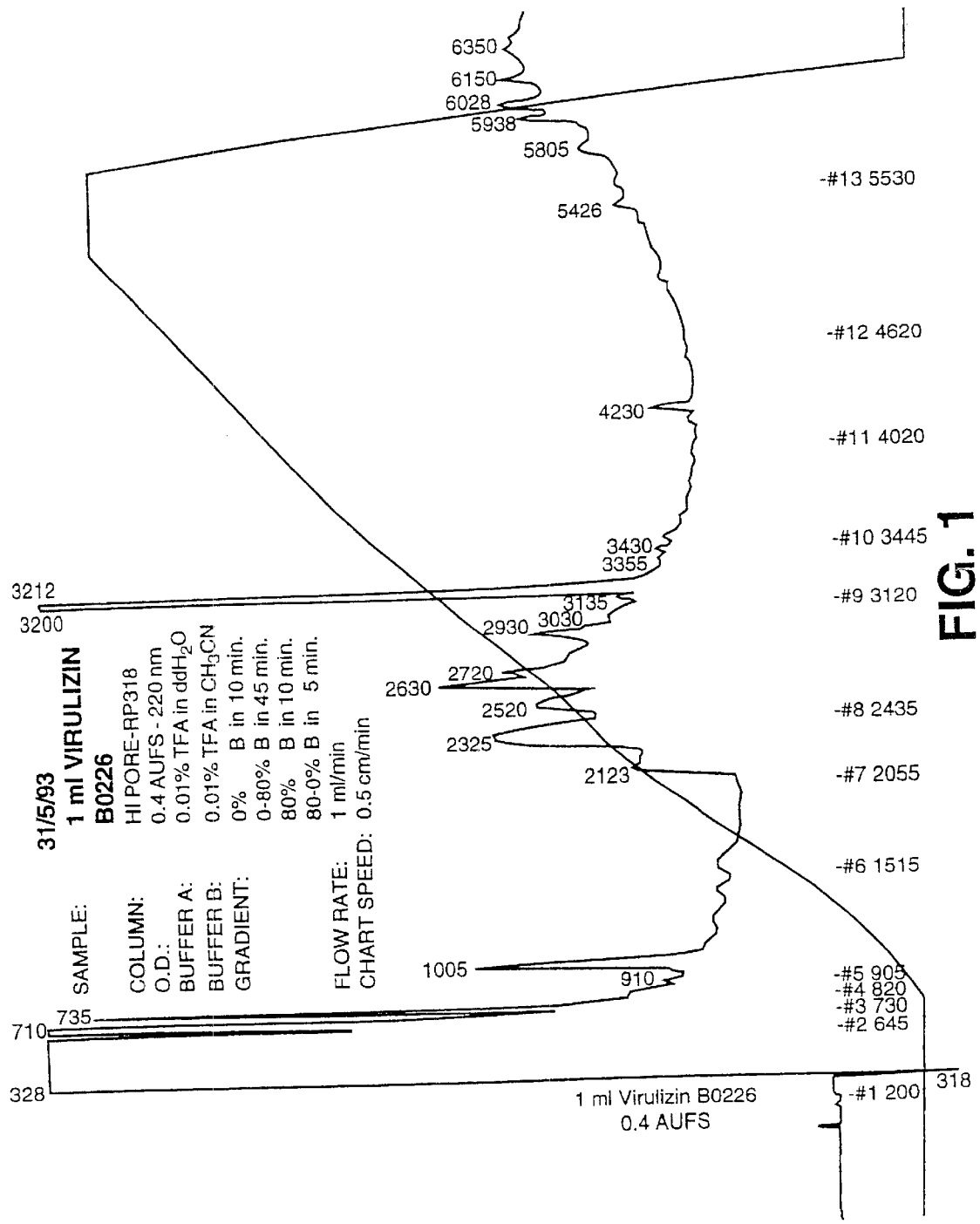
FIG. 1 is an HPLC profile for a concentrated composition of the invention.

As hereinbefore mentioned, the present invention relates to a composition for use as an immunomodulator comprising small molecular weight components of less than 3000 daltons, and having the following properties:

a) is extractable from bile of animals;

b) is capable of stimulating monocytes and macrophages in vitro;

c) is capable of modulating tumor necrosis factor production;

d) contains no measurable level of IL-1α, IL-1β, TNF, IL-6, IL-8, IL-4, GN-CSF or IFN-gamma;

e) has an anti-proliferative effect in a malignant mouse hybridoma cell line;

f) shows no cytotoxicity to human peripheral blood mononuclear cells; and g) is not an endotoxin.

More particularly, investigations have shown that the at least some of the compositions of the invention will stimulate normal monocytes to effect cytotoxicity towards the Chang hepatoma cell line, which is used to measure monocyte toxicity. Monocytes and macrophages from cancer patients (cervical and ovarian cancer) also have been reported to be stimulated by the composition to attack and destroy their own particular tumor cells.

The composition of the invention can modulate tumor necrosis factor (TNF) production. A preferred composition of the invention isolated from bile from bovines, promotes the release of TNF from human peripheral blood mononuclear cells in what appears to be physiological quantities. Because TNF is known to initiate a cascade of inflammatory and antitumor cytokine effects, the preferred composition could exert its antineoplastic effect by stimulating human leucocytes to release TNF (and possibly other cytokines). Accordingly, the present invention also may enhance lymphocyte and macrophage cytotoxicity towards tumor cells.

The composition of the invention has also been found to inhibit the growth of cells of mouse hybridoma cell line #6-1. The inhibitory effect of the composition in the mouse hybridoma cells suggests antiproliferative activity.

The effect of the composition on the survival of human peripheral blood mononuclear cells (PBMN) was also examined. The composition was found to be non-cytotoxic to human PBMN.

As further exemplified below, the composition of the present invention has, among others, the following characteristics:

1) The component or components responsible for TNF-release from PBMN eluted early from a $C_{18}$ RP-HPLC column.

2) The TNF-releasing component(s) is (are) precipitated, in part, by 80% acetonitrile.
3) The material unprecipitated by 80% acetonitrile retains some TNF-releasing activity.
4) The TNF-releasing activity in both the 80% acetonitrile precipitate and supernatant fractions eluted at the same early time from RP-HPLC. The results suggest that active TNF-releasing components in the composition belong to the same molecular family with perhaps some subtle molecular differences that account for solubility differences.
5) The composition causes the release of interleukin-1β (IL-1β), and the component responsible for the IL-1β release elutes early from RP-HPLC, suggesting that it is likely the same substance(s) that releases TNF.
6) The composition also causes the release of low quantities of interleukin-2 (IL-2).
7) The composition causes the release of granulocyte macrophage colony stimulating factor (GM-CSF); the 80% acetonitrile precipitate fraction is more active than the supernatant fraction.
8) The ratio of TNF to GM-CSF release is about 2:1.
9) The 80% acetonitrile precipitate fraction contains component(s) that release about 3 fold more TNF and GM-CSF than component(s) in the supernatant fraction.
10) Analysis of the aforementioned precipitates and supernatants fractions separated by RP-HPLC shows that releasing activity for TNF, IL-1β and GM-CSF elutes early for both the precipitate and supernatant. However, in the supernatant, some IL-1β activity elutes late.
11) It is likely that the same molecule(s), i.e., component (s), in the composition are responsible for releasing TNF, IL-1β and GM-CSF. It is possible that the composition acts to stimulate the release of multiple different cytokines, or alternatively, the composition triggers the production and release of one cytokine that in turn stimulates production and release of other cytokines.
12) Physicochemical analysis of the composition, including the precipitates and supernatants thereof, by SDS gel electrophoresis and molecular sieve HPLC indicates that the principal components are less than 2500 daltons.
13) Further physicochemical separation by hydrophilic (polyhydroxyethyl) molecular sieve HPLC confirms the small molecular weight of the components in the composition.
14) Amino acid analysis before and after acid hydrolysis suggest the presence of peptide bonds, indicating the presence of peptides.
15) Amino acid content of the active fraction from RP-HPLC shows high levels of glutamate/glutamine and glycine. In addition, residues of asparagine, threonine, serine and alanine were detected.
16) There are some unidentified ninhydrin positive residues that are likely free amino acids.

As hereinbefore mentioned, the composition of the invention may be prepared by (a) mixing bile from an animal, preferably a bovine, with an equal volume of an alcohol to produce a bile/alcohol solution; (b) separating out the alcohol soluble fraction and isolating a solution substantially free of alcohol; (c) removing bile pigments from the solution to obtain a colorless liquid; (d) treating the colorless liquid to substantially remove any residual alcohol; (e) extracting the colorless liquid with ether and isolating the aqueous phase; and (f) removing residual ether from the aqueous phase.

The composition is obtained from the bile of any animal which produces bile, preferably non-human animals. While the composition may possess a different activity toward a specific disease if obtained from the bile of one species as opposed to another, a generally suitable source of bile is that taken from bovines, ovines and swine. In most cases, it is practical to obtain the bile of slaughtered healthy food animals, such as bovines, ovines and pigs, for use in the preparation of the composition of the invention. The bile thus collected should come directly from the gall bladders of the slaughtered animals and should be substantially clear, thereby indicating that the bile preparation has a low mucus content and is substantially free of pus or blood.

In a preferred embodiment of the method, bile from bovine sources is utilized. Bovine bile is plentiful, because, in part, relatively large quantities can be extracted from each animal. Moreover, bovines are routinely slaughtered and inspected under health-related regulations, thus such animals provide a reliable source for preparing the composition of the invention. Furthermore, humans are less likely to have an allergic reaction to material of bovine origin.

The bile is mixed with an equal volume of an alcohol to produce a bile/alcohol solution, which is 50% alcohol. The alcohol may be an aliphatic alcohol, preferably methanol, ethanol, or propanol, most preferably ethanol.

A solution that is substantially free of the 50% alcohol-insoluble material may be isolated by centrifuging. Preferably, the bile/alcohol mixture is centrifuged at 3000–5000 RPM, most preferably 4200 RPM, for at least 2 hours, at about 15–25° C. The alcohol contained in the bile/alcohol-soluble fraction then may be removed by taking advantage of the different volatility of alcohol and water, using conventional methods, i.e., heating the fraction to a suitable temperature, e.g., 80–85° C., for a suitable amount of time, e.g., up to about 10 hours.

Bile pigments may be removed from the solution to obtain a colorless liquid by using activated charcoal, polyamidic microgranules, or filtration. Preferably, an activated charcoal treatment is utilised. The procedure may be repeated in order that the solution satisfies optical density and conductivity standards.

The colorless liquid is treated to remove substantially any residual alcohol, using conventional methods. Preferably the colorless liquid is filtered using a filter having about a 1.0–3.5 μm retention, most preferably a retention of 2.5 μm.

The colorless liquid is then extracted with ether and the aqueous phase is isolated. The ether used in this step is preferably dimethyl ether, ethyl ether, n-propyl ether, isopropyl ether, or n-butyl ether, most preferably ethyl ether.

Residual ether may be removed from the aqueous phase by, for example, heating the solution up to 55° C., preferably up to about 40° C. for about 5–15 hours, most preferably for about 10 hours.

The composition may be used without further modification simply by packaging it in vials and sterilizing. The composition also may be used in a concentrated form. A preferred concentrated form is prepared as follows. Prior to step (e) described hereinabove, the colorless liquid optionally may be concentrated to about one eighth of the volume of the bile/alcohol solution by, for example, heating to a temperature of less than about 85° C., preferably, to about 60°–70° C. After step (f), the aqueous phase may be concentrated so that it is one tenth of the volume of the bile/ethanol solution by, for example, heating to about 80–85° C.

In a preferred method to prepare a composition of the invention, the collected bile is mixed with an equal volume of ethyl alcohol. The bile/alcohol mixture is then centrifuged at about 4200 RPM for at least 2½ hours, at about 20±2° C. The supernatant liquid is decanted and checked for pH and ethanol content. Bile pigments are then removed using activated charcoal. The treated bile/ethanol solution is then monitored for optical density (O.D.) and conductivity. O.D. levels or conductivity levels outside acceptable specifications require that the bile/ethanol solution be given additional treatment to remove bile pigments, for example treatment again with activated carbon to achieve a reading within specification limits.

Following activated carbon treatment, the solution is filtered through a filter having a 2.5 μm retention, the alcohol is evaporated off by heating to less than 85° C. and the solution is concentrated to approximately one eighth of the original bile/ethanol solution volume. The concentrated solution is cooled to between about 20–25° C. This solution is then mixed with ethyl ether and the ether phase is discarded. Preferably, relatively small volumes of ether and strong agitation are used, such as 0.1 to 1 volume, preferably 0.2 to 0.5 volume. This step may be repeated once. The aqueous phase is heated to remove residual ether by heating up to 55° C. for about 10 hours, and further reduced in volume to one tenth of the original bile/ethanol volume by heating to about 80–85° C. This solution is then tested for appearance, biological activity, and ethanol and ether content.

The pH of the composition may be adjusted to physiological pH, i.e. 7.4–7.5, using hydrochloric acid (1%) solution and sodium hydroxide (1% solution), and a buffered solution may be obtained using dibasic and monobasic sodium phosphate salts as buffers, using conventional methods.

The composition may be used without further modification by simply packaging it in vials and sterilizing. A preferred sterilization method is to subject the composition to three sterilization cycles by autoclaving followed by incubation.

The composition may be used in a concentrated form. The preparation of the concentrated form is described above. The composition may also be lyophilized.

The composition and concentrated composition are clear yellowish solutions essentially free of foreign matter, containing not more than 10 ppm ethanol and not more than 5 ppm ether. In the bioassay described in Example 4, the composition has been shown to cause non-proliferative growth at about 18 units per ml.

Figure 2:
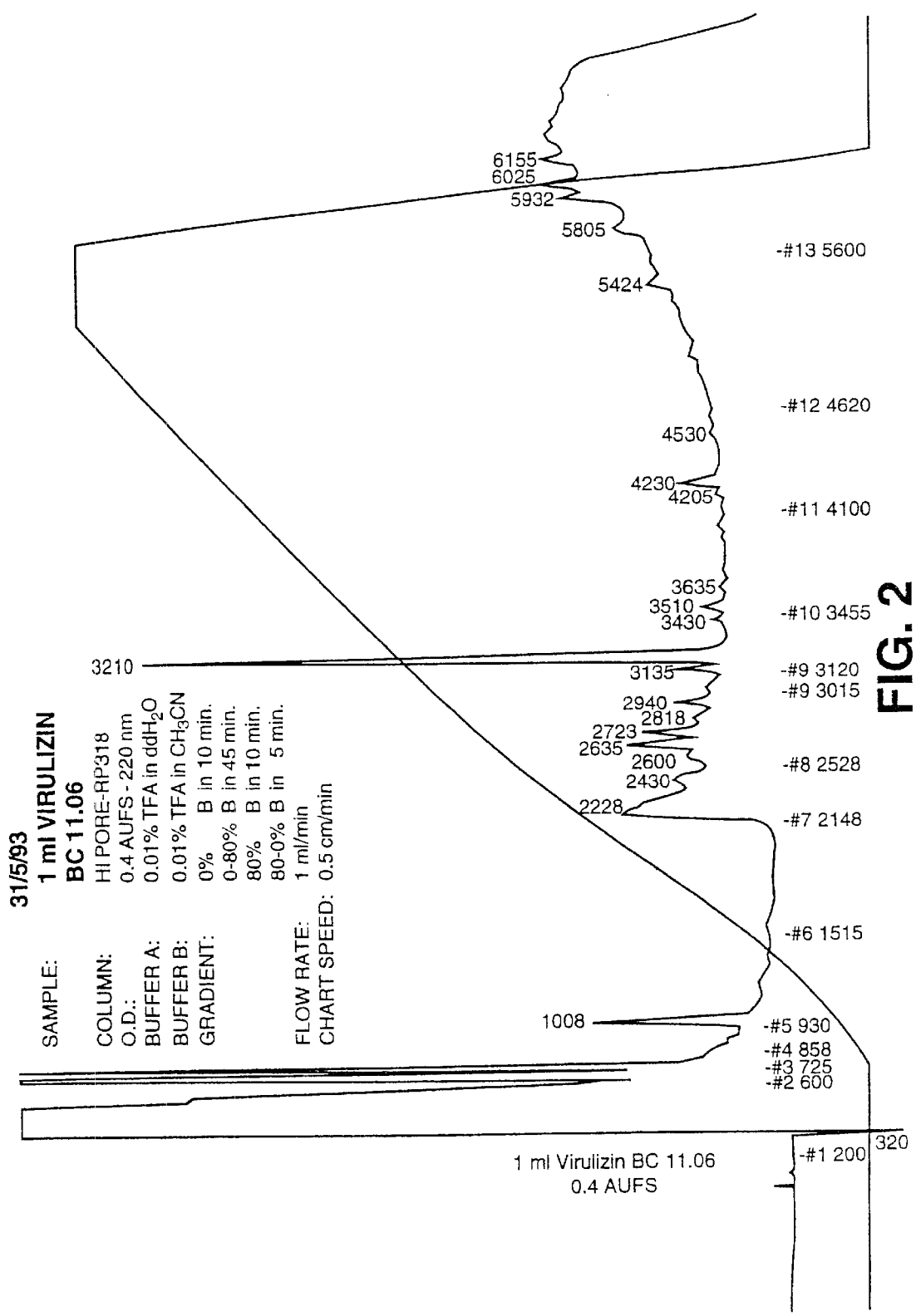
FIG. 2 is an HPLC profile for a concentrated composition of the invention.
Figure 3:
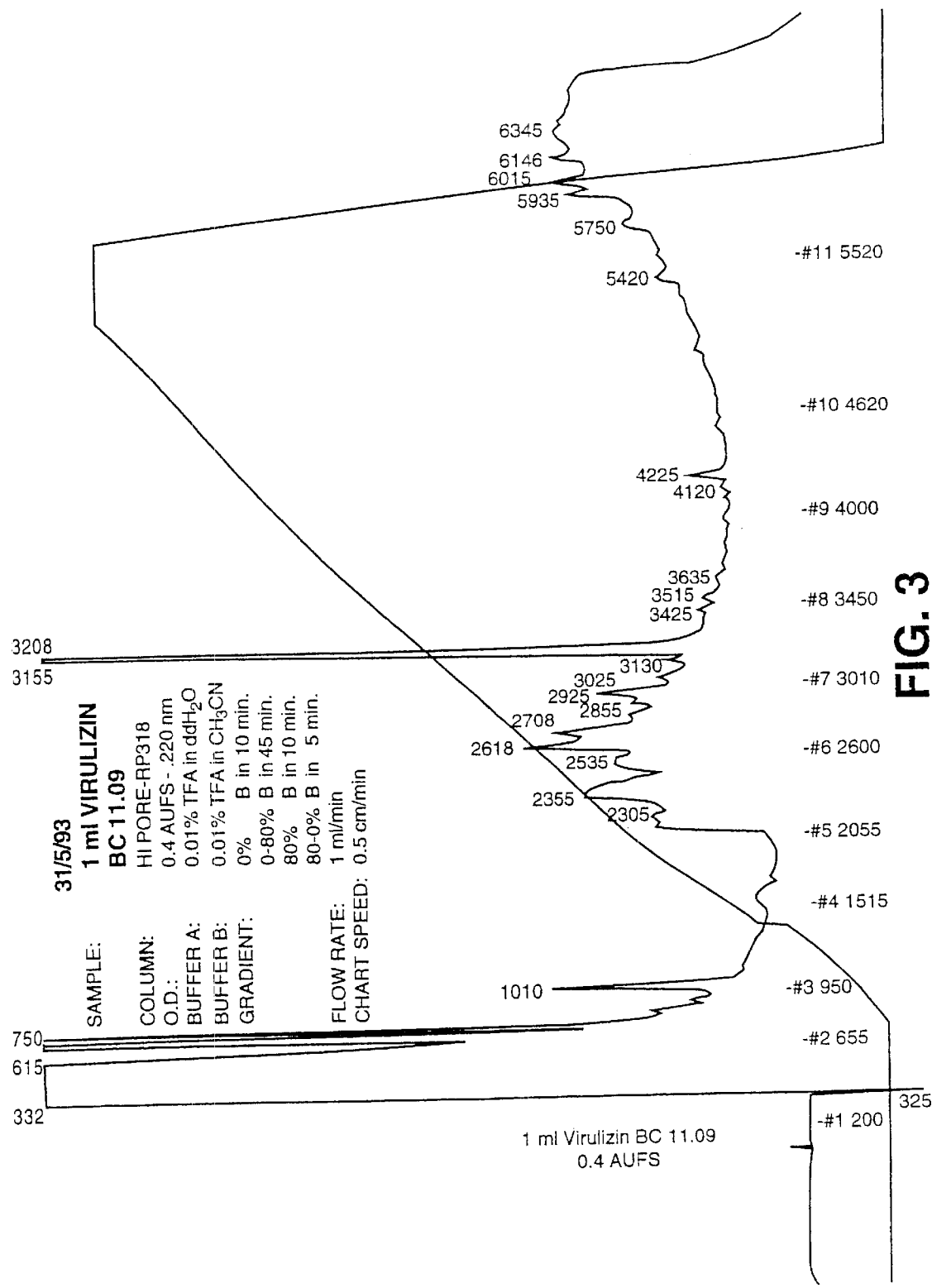
FIG. 3 is an HPLC profile for a concentrated composition of the invention.
Figure 4:
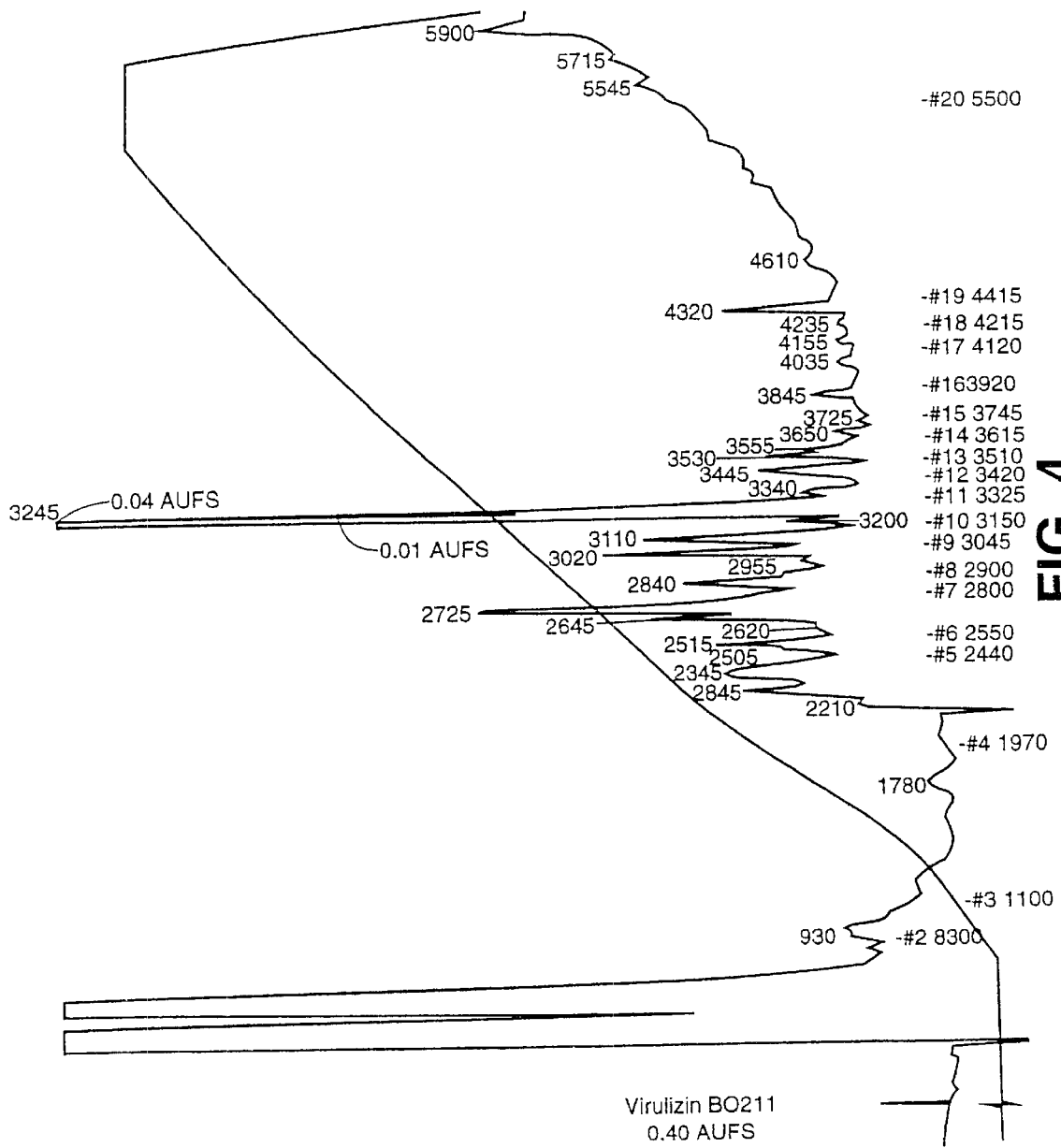
FIG. 4 is an HPLC profile for a composition of the invention.
Figure 5:
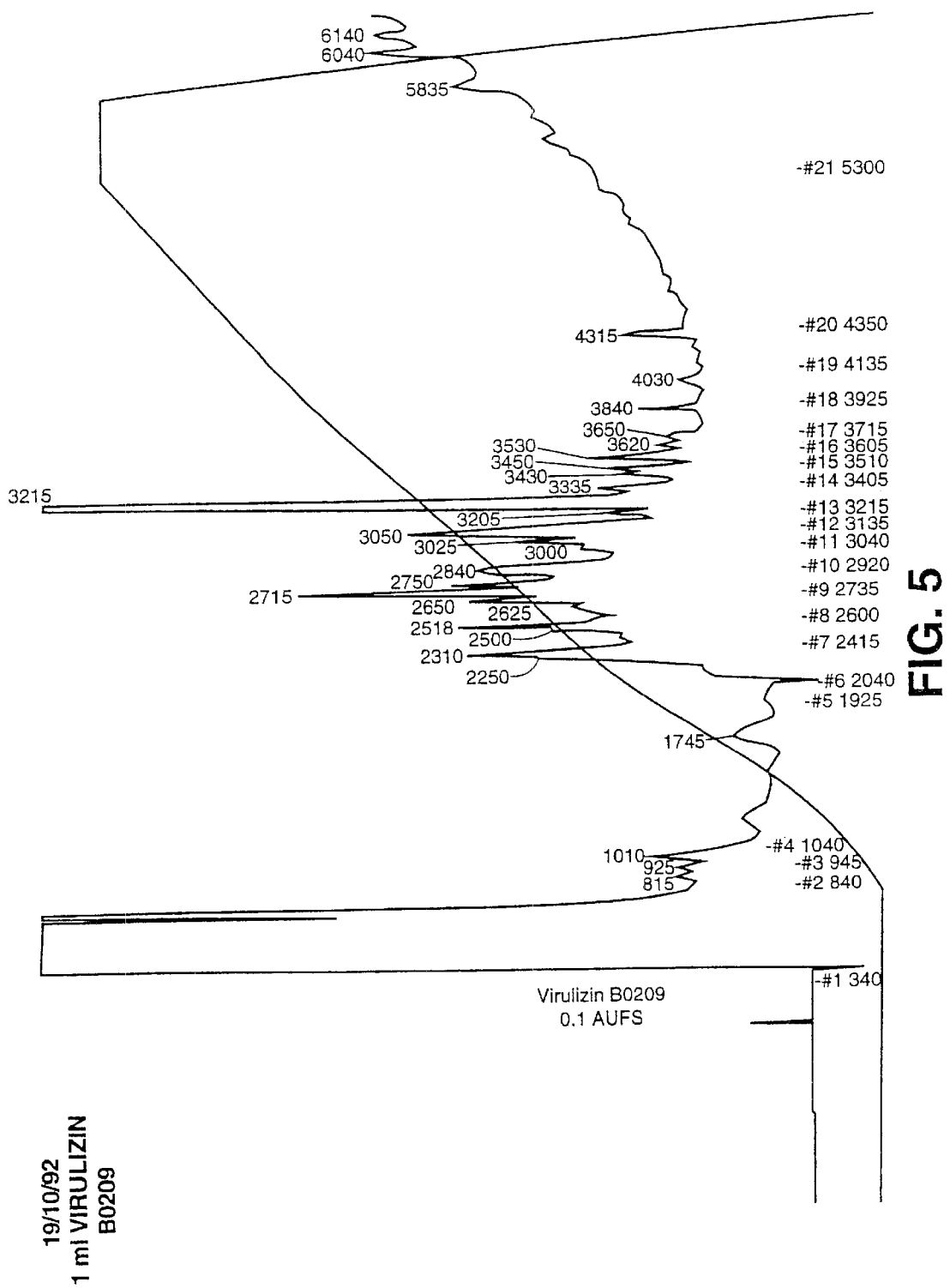
FIG. 5 is an HPLC profile for a composition of the invention.
Figure 6:
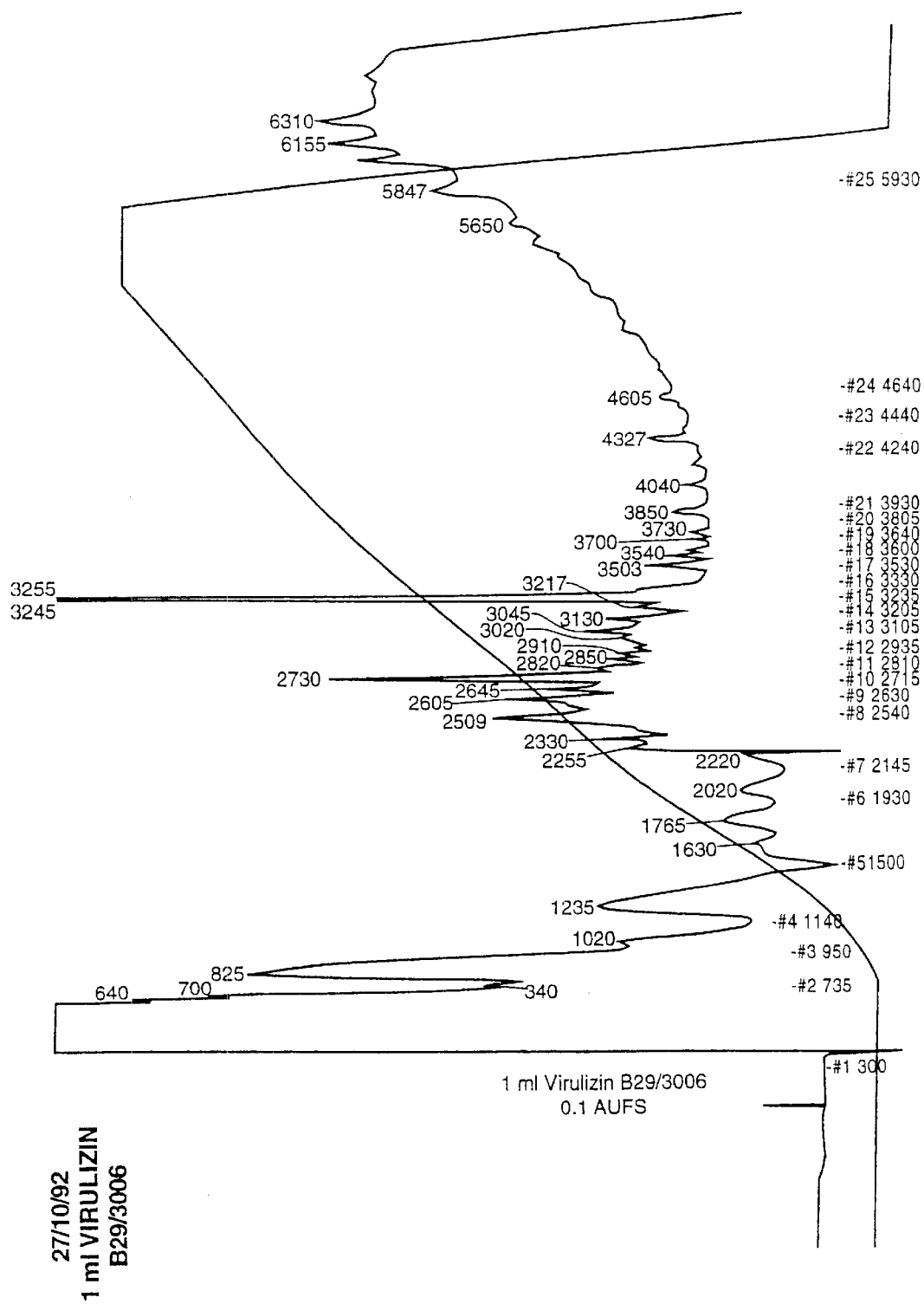
FIG. 6 is an HPLC profile for a composition of the invention.
Figure 7:
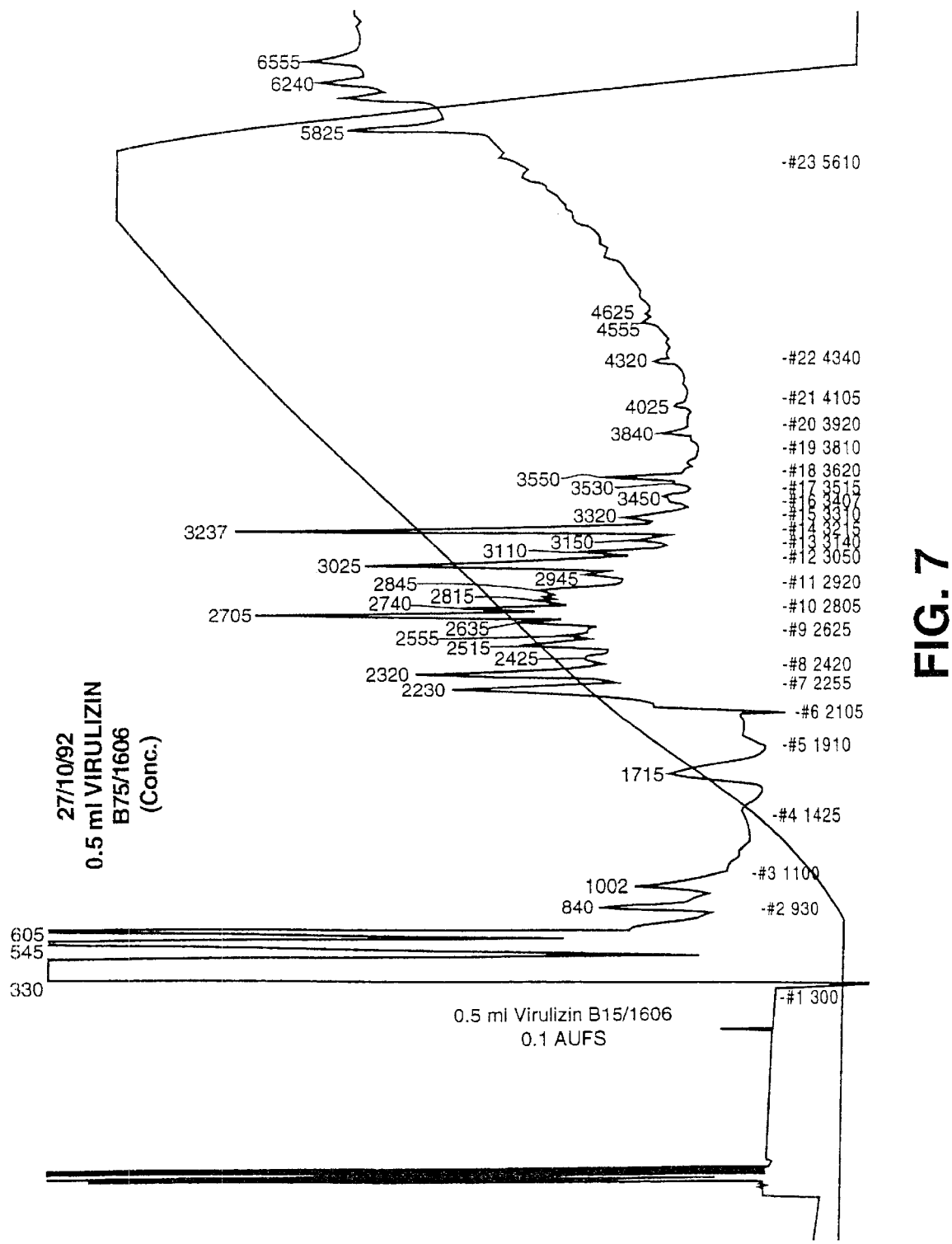
FIG. 7 is an HPLC profile for a composition of the invention.

The compositions of the invention can be produced in a consistently reproducible form using the method as generally described above with demonstrated identity, potency and purity from batch to batch. Identity and purity are determined using reverse-phase high pressure liquid chromatography. (See Example 1). The compositions of the invention have a consistently reproducible pattern on reverse-phase HPLC, in which peaks are seen early in the exclusion fraction at about 27 and 32 minutes. Before, in-between and after the tall peaks, there are smaller peaks that vary in intensity. The HPLC readings for three lots of the concentrated composition of the invention are shown in FIGS. 1 to 3. RP-HPLC profiles for batches B0211 (FIG. 4), B0209 (FIG. 5), B29/3006 (FIG. 6) and B15/1606 (FIG. 7), also show a very reproducible pattern. The compositions also display non-proliferative growth of about 18 units per ml in the bioassay described in Example 4. The compositions are also characterized by the properties hereinbefore mentioned, for example their ability to stimulate monocytes and macrophages in vitro, etc.

Compounds likely to be present in the present composition, considering the source, include sulfonated bile acids, oxidized bile acids, other naturally occurring bile acids, and their amino acid (especially glycine and taurine) conjugates and sterols. Accordingly, it is believed that the present composition includes at least one compound having the formula

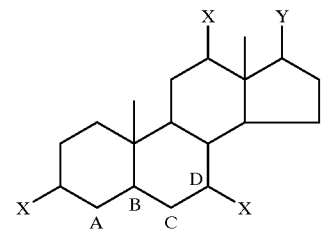

wherein the molecule may or may not be fully saturated, such that, for example, the bond between A and B, B and C, or C and D may be single or double bonds, and wherein X is H, OH, =O, or $OSO_3H$; and Y is

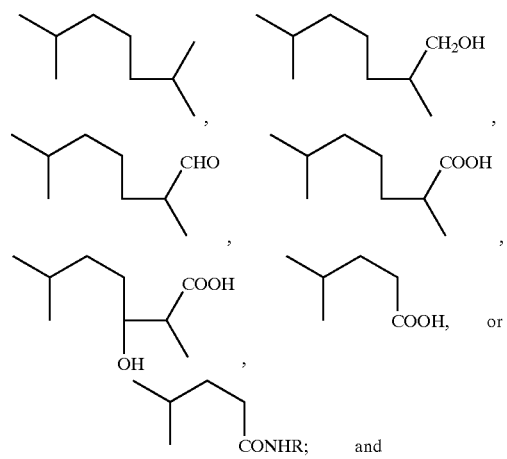

wherein R is an amino acid residue, such as, for example, glycyl, glutamyl, or tauryl, thereby forming the glycine or taurine conjugate.

In particular, the composition of the present invention has been analyzed as to its component compounds, including organic and inorganic components. Such information was derived using standard methods of analytical chemistry, including mass spectroscopy (MS). The results of such studies include, for example, the identification of specific bile acid compounds thought to be present, including cholic acid, glycocholic acid, deoxyglycocholic acid, ursodeoxycholic acid, cholesterol sulfate, deoxycholic acid, chenodeoxycholic acid, and taurocholic acid.

From the MS it is not distinguishable if the loss of OH and $H_2$ of some compounds are occurring in the MS or if the deoxy, dideoxy and unsaturated analogs of such compounds are also present to begin with. These compounds may all be present as salts of ammonium, alkylammonium and inorganic cations.

The MS analysis also supports the identification in the present composition of phospholipids, sphingolipids and related agents capable of forming miscelles. Specific compounds thought to be present include:

stearic acid $CH_3(CH_2)_{16}COOH$, palmitic acid $CH_3(CH_2)_{14}COOH$ oleic acid Z-9 octadecanoic acid: $CH_3(CH_2)_2CH_2CH=CHCH_2(CH_2)_6COOH$ oxidized or hydroxylated/unsaturated short chain fatty acids: $C_6H_8O_3$ (e.g., $CH_3CH=CHCOCH_2COOH$ or a $C_6$ acid with 2 double bonds and a hydroxide)

acetic acid stearic acid diglyceride palmitic acid diglyceride stearic acid, palmitic acid diglyceride stearic acid-monoglyceride-phosphocholine (a lysolecithin)

stearic acid monoglyceride stearic acid triglyceride palmitic acid monoglyceride phosphocholine phosphoserine phosphosphingosine stearic acid-sphingosine sphingosine stearic acid amide stearic acid methylamide palmitic acid amide lecithin sialic acid-glycerol dimer In addition, preliminary HPLC and titration evidence has been obtained which shows that shorter chain fatty acids are also present.

Phospholipid, sphingolipid, and related hydrolysis product compounds likely to be present considering the source and the information derived from the MS and HPLC analyses include at least one compound having the formula

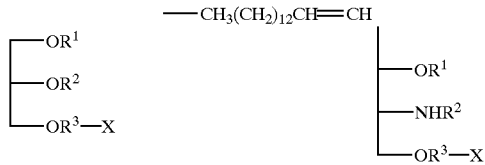

where $R^1, R^2, R^3$ are different or the same and are H, $COR^4$, $CH=CH-R^5$, X, $-P(O)(OH)O-$, or $-S(O)_2O-$; X is selected from the group consisting of choline, ethanol amine, N-alkylated ethanolamines, serine, inositol, sugars bearing free hydroxyls, amino-sugars, sulfonated sugars, and sialic acids; $R^4$ is $C_1-C_{30}$ alkyl that is saturated or unsaturated, oxidized or hydroxylated; and $R^5$ is an alkyl group or oxidized and/or hydroxylated analogs thereof.

The fatty acids and their conjugates may be present in the aforementioned aqueous extract as salts. The solubility of such compounds is also enhanced by other components of the mixture. Amides of the included carboxylic acids, $RCONR^1R^2$, where $R^1$ and $R^2$ are the same or different and are H or alkyl, are also believed to be present.

A third class of compounds, namely mucin and proteoglycan hydrolysis products, are also likely to be present, considering the source of the composition and the aforementioned MS analysis thereof. Such compounds include hydrolysis products of mucoproteins from bile and from the gallbladder wall, such as: chondroitin 4- and 6-sulfates, dermatan sulfate, heparin, heparin sulfate, hyaluronic acid and the hydrolysis products (monomers, dimers, oligomers and polymers) of these mucins. Chitin and other mucins may be similarly hydrolyzed, which hydrolysis products would include:

N-acetyl-D-glycosamine, N-acetyl-D-galactosamine-4-sulfate, galactose-6-sulfate, N-acetyl-D-glucosamine-6-sulfate, glycosamine-6-sulfate, D-glycosamine 2-sulfate, D-glycosamine 2,3-disulfate, D-galactose-6-sulfate, glucuronic aid 2-sulfate, N-acetylneuraminic acid, sialic acid, N-acetyl chondrosine, chondroitin 4-sulfate, chondroitin 6-sulfate, D-glucosamine, D-galactosamine, glucuronic acid, glucose, galactose, mannose, fucose, iduronic acid, hexose, hexosamine, ester sulfate, glucuronic acid, chondrosamine, 2-amino-2-deoxy-D-galactose, serine, proline, threonine, alanine glycine taurine, glutamic acid, aspartic acid, histidine, and small peptides.

Similar products would be obtained by hydrolysis of mucins such as keratin sulfates, dermatan sulfates the natural sugar—sugar linkages in the dimers, oligomers and polymers may be replaced by $-O-Si(OH)_2-O-$ bridges between the sugar monomers or adjacent sugar chains.

In particular, specific mucin and proteoglycan hydrolysis product compounds thought to be present include:

sialic acids and their mono and diacetylated and glycolylated monomers;

N-acetylneuraminic acid;

hexosamines;

L-fucose;

hexosamine-hexuronic acid (dimer) disulfate;

glucuronic acid or iduronic acid disulfate, monoacetylated;

sialic acid-glycerol (dimer); and dimers, trimers, oligomers and polymers of the above monomers in acetylated and sulfated form.

A fourth class of compounds, namely fat-soluble vitamins, likely to be present considering the source and the aforementioned MS analysis, include A, D, and K vitamins (e.g., D1, D3, D4, K1, K2, K5, K6, K7, K-S(II), and Vitamin E acetate, for example.

In particular, specific fat-soluble vitamin compounds thought to be present include at least one of the group consisting of Vitamin A2, Vitamin D1, Lumisterol (present from its vitamin D1 complex), Vitamin E, Vitamin K1 oxide, and Vitamin K5.

Various miscellaneous organic compounds are likely to be present, considering the source and the aforementioned MS analysis. Such compounds include:

bilirubin, and its gluconuride conjugate;

biliverdin, and its gluconuride conjugate;

traces of steroids;

other plasma solutes, such as sugars, purines and pyrimidines;

miscellaneous dietary lipids; and glutathione and its hydrolysis products.

In particular, specific miscellaneous organic compounds believed to be present in the composition include at least one of the group consisting of urea, methyl amine, dimethylamine, ethylamine, methylethylamine, diethylamine, dipropylamine, butylethylamine, ammonia, choline, taurine, glutamic acid, glycine, alanine, p-ser, p-eu, p-ea, asp thr ser sar, a-aba, cit, val, ile, leu, B-ala, G-aba, OH-lys, orn, lys, butylated hydroxy toluene (BHT), and polyethylene glycol.

Amines present in the present composition, particularly the secondary amines, may include nitrogen oxides from the air, thus forming nitroso compounds. N-oxides and N-carbamate byproducts may also be included. This series of amines cited above should be extended to include all primary, secondary and tertiary alkylamines.

Certain inorganic elements have been identified and quantified (mg/l) as follows:

| | |
|---|---|
| Tungsten | 0.07 |
| Zinc | 0.666 |
| Phosphorus | 378 |
| Cadmium | 0.01 |
| Cobalt | 0.008 |
| Nickel | 0.022 |
| Barium | 0.032 |
| Iron | 0.022 |
| Manganese | 0.039 |
| Chromium | 0.060 |
| Magnesium | 7.46 |
| Aluminum | 0.136 |
| Calcium | 5.97 |
| Copper | 0.087 |
| Titanium | 0.01 |
| Strontium | 0.060 |
| Sodium | 9600 |
| Potassium | 483 |
| Chloride | 15400 |
| Ammonia | 218 |
| Vanadium | 1 ppm |

The compositions of the invention have valuable pharmacological properties. In particular, the compositions of the invention have anti-proliferative effects, effect neoplastic growth, and effect release of tumor necrosis factor. The compositions have been shown to cause no significant toxicity and only transient adverse side effects (for example, slight fever, polydipsia, pain at injection site). They have also been found to contain no detectable components of high molecular weigh matter (i.e., above about 5,000 daltons), which can cause harmful immunologic reactions. The compositions may be used as agents for the prophylaxis and treatment of conditions requiring modification of the immune response, in particular infectious disease, neoplasias, and autoimmune diseases. They may be especially useful in the treatment of various forms of neoplasia, such as leukemias, lymphomas, melanomas, adenomas, sarcomas, and carcinomas. In particular, the composition may be useful for treating malignant melanoma, pancreatic cancer, cervico-uterine cancer, cancer of the kidney, stomach, lung, rectum, breast, bowel, gastric, liver, thyroid, neck, cervix, salivary gland, leg, tongue, lip, bile duct, pelvis, mediastinum, urethra, bronchogenic, bladder, esophagus and colon, and Kaposi's Sarcoma, which is a form of cancer associated with HIV-infected patients with Acquired Immune Deficiency Syndrome (AIDS). The composition may also be used for other anti-proliferative conditions, such as arthrosclerosis and viral infections, in particular AIDS. It may also be used in the treatment of autoimmune diseases, including multiple sclerosis, rheumatoid arthritis, systemic lupus erythematosus, Type I diabetes, myasthenia gravis, Addison's Disease, autoimmune hemolytic anaemia, Crohn's disease, Goodpasture's syndrome, Graves' disease, Hashimoto's thyroiditis, idiopathic thrombocytopenic purpura, pernicious anaemia, post-streptococcal glomerulonephritis, psoriasis, scleroderma, Sjogren's syndrome, spontaneous infertility, and pemphigus vulgaris.

The compositions of the invention may be converted using customary methods into pharmaceutical agents. The pharmaceutical agents contain the composition of the invention either alone or together with other active substances. Such pharmaceutical agents can be for oral, topical, rectal, parenteral, local, inhalant, or intracerebral use. They are therefore in solid or semisolid form, for example pills, tablets, creams, gelatin capsules, capsules, suppositories, soft gelatin capsules, gels, membranes, and tubelets. For parenteral and intracerebral uses, those forms for intramuscular or subcutaneous administration can be used, or forms for infusion or intravenous or intracerebral injection can be used, and can therefore be prepared as solutions of the compositions or as powders of the active compositions to be mixed with one or more pharmaceutically acceptable excipients or diluents, suitable for the aforesaid uses and with an osmolarity which is compatible with the physiological fluids. For local use, those preparations in the form of creams or ointments for topical use or in the form of sprays may be considered; for inhalant uses, preparations in the form of sprays, for example nose sprays, may be considered. Preferably, the composition is administered intramuscularly.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in *Remington's Pharmaceutical Sciences* (Nack Publishing Company, Easton, Pa., USA 1985).

On this basis, the pharmaceutical agents include, albeit not exclusively, the composition of the invention in association with one or more pharmaceutically acceptable vehicles or diluents, and are contained in buffered solutions with a suitable pH and iso-osmotic with the physiological fluids.

The compositions are indicated as therapeutic agents either alone or in conjunction with other therapeutic agents or other forms of treatment. For example, in the case of a malignant tumor, the present treatment may render a tumor suitable for surgical removal where it was not previously operable. The compositions and agents of the invention are intended for administration to humans or animals.

In general, a dosage range of the composition is envisaged for administration in human medicine of from about 0.01 to 20 mg/kg, preferably from about 0.1 to 10 mg/kg, most preferably 0.1 to 1 mg/kg of body weight daily may be employed. In the case of intravenous administration, the dosage is about 0.1 to 5 mg/kg of body weight daily, and in the case of oral administration the dosage is about 1 to 5 mg/kg of body weight daily. Where the concentrated composition is used, approximately half the above mentioned dosages may be used. For example, for intramuscular administration, a dosage of about 0.2 to 1.0 mg/kg of body weight daily, preferably 0.275–0.75 mg/kg of body weight daily may be used.

It will be appreciated by medical practitioners that it may be necessary to deviate from the amounts mentioned and, in particular, to do so as a function of the body weight and condition of the animal to be treated, the particular disease to be treated, the nature of the administration route and the therapy desired. In addition, the type of animal and its individual behaviour towards the medicine or the nature of its formulation and the time or interval at which it is administered may also indicate use of amounts different from those mentioned. Thus it may suffice, in some cases, to manage with less than the above-mentioned minimum amounts whilst in other cases the upper limit mentioned must be exceeded. Where major amounts are administered, it may be advisable to divide these into several administrations over the course of the day.

Thus, the present invention comprises a process for preparing an immunomodulator composition comprising (a) mixing bile from an animal with a water-soluble solvent to produce a bile/solvent solution; (b) isolating an aqueous solution substantially free of solvent from the bile/solvent solution; and (c) removing bile pigments from the substantially solvent-free solution to obtain a colorless liquid, preferably where the water soluble solvent is an alcohol, and where the bile from the animal is mixed with an equal volume of the alcohol. Preferred aspects of the aforementioned process also comprise further concentrating the colorless liquid to about one-eighth, or one-tenth, the original volume of the bile/solvent solution. Obviously, compositions produced via the above process form a preferred aspect of the invention.

The present invention also comprises a composition for use as an immunomodulator, comprising at least one component having a molecular weight of less than about 3000 daltons, which shows no cytotoxicity to human peripheral blood mononuclear cells, and has at least one of the following properties:
  (a) is capable of stimulating monocytes and macrophages in vitro or in vivo to produce one or more cytokines;
  (b) is capable of stimulating monocytes or macrophages to produce tumor necrosis factor in vitro or in vivo; or
  (c) has an anti-proliferative effect in a malignant mouse hybridoma cell line; and
wherein said component is not an endotoxin, IL-1α, IL-1β, TNF, IL-4, IL-6, IL-8, GM-CSF or IFN-gamma. Such compositions may be obtained from the bile of animals, preferably bovines, or from other sources. In a preferred embodiment of the composition, the composition stimulates tumor necrosis factor production in vitro or in vivo, and most preferably in humans, in the absence of exogenous IL-1α, IL-1β, TNF, IL-4, IL-6, IL-8, GM-CSF, and IFN-gamma.

The compositions of the present invention also have components which can be characterized by column chromatography such that when said composition is dried to obtain a solid residue, and 2 grams of said residue are dissolved in 20 ml of a 10% concentrated ammonium hydroxide solution in methanol, and after any insoluble material is removed, is subjected to column chromatography in a methanol column having dimensions of 5 cm×12.5 cm, and containing 102 g of 60 A flash silica gel, and operating at a pressure of 10 pounds per square inch and a flow rate of 11 ml/min with a 10% concentrated ammonium hydroxide in methanol solvent solution, said component is eluted from the column in a fraction taken when the total column elution is between about 180 and about 220 ml, between about 220 ml to about 260 ml, or between about 260 ml and about 300 ml.

Characterization of components may also be accomplished by ion-exchange chromatography, such that when 10 ml of said composition is subjected to anion-exchange chromatography in a column containing Bio-Rad AG-1 hydroxide form resin in an amount sufficient to bind substantially all the anions present in said 10 ml of said composition, said component is eluted from the column using a step gradient of ammonium bicarbonate buffer at a buffer concentration from about 0.5 M to about 1.5 M, preferably at a buffer concentration from about 1.0 M to about 1.5 M, and most preferably at a buffer concentration of about 1.5 M.

Reversed-phase (C18) HPLC can also be used for characterization of components, such that when said composition is lyophilized and reconstituted in 0.1% TFA in water and then subjected to reversed-phase (C18) HPLC in a Phenomenex WP60009-C18 column, having dimensions of 250×4.6 mm, where a first buffer of 0.1% TFA in water is run through the column for about 10 minutes, then a linear gradient from 0 to 80% of a second buffer of 0.1% TFA in acetonitrile is run for about 55 minutes, followed by an 80% solution of the second buffer for about 5 minutes, and an 80%-0% gradient of the second buffer for about 5 minutes, and where flow rate is 1 ml/min. and the capacity of the column and buffers are not exceeded, said component is eluted from the column at a time from about 2.4 minutes to about 3.4 minutes after said reconstituted composition is applied to the column. Characterization of components of the composition can also be accomplished by an additional reversed-phase HPLC method, such that when said composition is dialyzed or dissolved in a first buffer of 0.1% TFA in water and then subjected to reversed-phase (C18) HPLC in a Bio-Rad Hi-Pore RP 318 (C18) column, having dimensions of 250×4.6 mm, where the first buffer is run through the column for about 10 minutes, then a linear gradient from 0–80% of a second buffer of 0.1% TFA in acetonitrile is run for about 55 minutes, followed by an 80% solution of the second buffer for about 5 minutes, and an 80-0% gradient of the second buffer for about five minutes, and where the flow rate is 1 ml/min. and the capacity of the column and the buffers are not exceeded, said component is eluted from the column at a time from about 2 minutes to about 21.4 minutes, or at a time from about 21.4 minutes to about 25.6 minutes after said dialyzed composition is applied to the column.

The compositions of the present invention can also be characterized by TLC, such that when said composition is subjected to thin layer chromatography on silica gel plates in 10% concentrated ammonium hydroxide in methanol and visualized with a ninhydrin spray, a positive reaction with ninhydrin occurs at an $R_f$ value from about 0.80 to about 0.90.

The present invention also comprises a method of stimulating tumor necrosis factor production in humans, comprising administering an effective amount of a composition comprising at least one of the following compounds:

(a) a compound of the formula

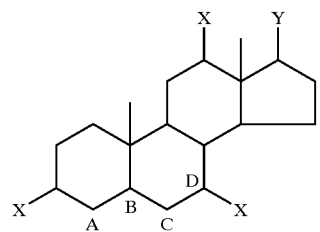

where the bonds between A–B, B–C, and C–D may be single or double bonds, and where X=H, OH, =O, or $OSO_3H$; and Y=

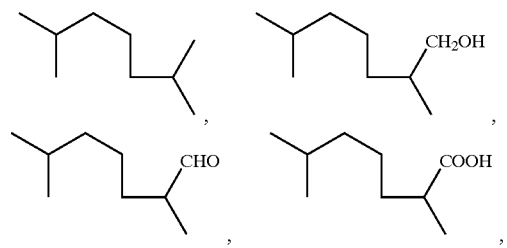

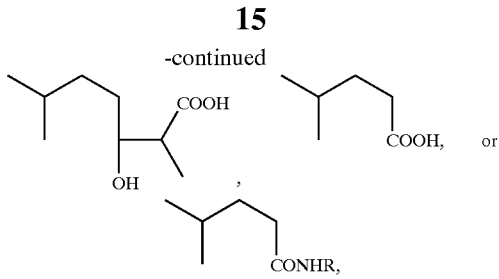

where R is an amino acid residue;

(b) a compound of the formula $$(R^1O)CH_2CH(OR^2)CH_2(OR^3-X)$$

or

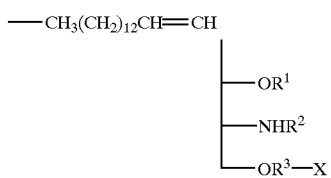

where $R^1$, $R^2$ and $R^3$ are H, $COR^4$, $CH=CH-R^5$, X, $P(O)(OH)O-$, or $-S(O)_2O-$;

X is choline, ethanolamine, N-alkylated ethanolamines, serine, inositol, sugars bearing free hydroxyls, amino-sugars, sulfonated sugars, or sialic acids; and $R^4$ is a saturated or unsaturated alkyl group having a carbon chain from about $C_1$ to $C_{30}$, or oxidized and hydroxylated analogs thereof; and $R^5$ is an alkyl group or oxidized and hydroxylated analogs thereof;

(c) a mucin hydrolysis product or a proteoglycan hydrolysis product; or (d) a fat-soluble vitamin.

Preferably, compositions of the inventive method comprise at least one compound selected from the group consisting of taurocholic acid and its sulphated derivatives; glycocholic acid and its sulphated derivatives; sphingosine; a diacyl glycerol; lecithin; an oligosaccharide of less than 10 saccharide units in length, where said oligosaccharide is comprised of sialic acid, fucose, hexosamines, or sulphated hexosamines; Vitamin A; retinolic acid derivatives; retinol derivatives; taurine; and glutamic acid and its conjugates. The composition may also additionally comprise at least one compound selected from the group consisting of ammonia; primary alkyl amines; secondary alkyl amines; tertiary alkyl amines; and a carboxylic acid $R^4CO_2H$, wherein $R^4$ is $C_1$–$C_{30}$ alkyl that is saturated or unsaturated, and oxidized and/or hydroxylized derivatives thereof.

The method of the invention also embraces stimulation of TNF production by administration of a composition comprising at least one compound selected from the group consisting of taurocholic acid and its sulphated derivatives; glycocholic acid and its sulphated derivatives; sphingosine; a diacyl glycerol; lecithin; an oligosaccharide of less than 10 saccharide units in length, where said oligosaccharide is comprised of sialic acid, fucose, hexosamines, or sulphated hexosamines; Vitamin A; retinoic acid derivatives; retinol derivatives; taurine; and glutamic acid and its conjugates.

The present invention also provides a method of treating pancreatic cancer comprising administering to a patient suffering from said cancer a therapeutically effective amount of the compositions of the invention.

Also forming part of the present invention are compositions comprising (1) micelles of sphingosine or sphingosine complexed with a salt, or (2) micelles of retinolic acid or its derivaties, which have at least one of the following properties:

(a) is capable of stimulating monocytes and macrophages in vitro to produce one or more cytokines;

(b) is capable of stimulating monocytes or macrophages to produce tumor necrosis factor in vitro or in vivo; or (c) has an anti-proliferative effect in a malignant mouse hydridoma cell line.

The micelles may also comprise a diacyl glyceride or lecithin, and may further comprise a bile acid salt, and a source of ammonium or alkyl ammonium ions.

Finally, the present invention also contemplates compositions comprising (1) sphingosine, a bile acid salt and a source of ammonium or alkyl ammonium ions, (2) a bile acid salt, sphingosine, a diacyl glycerol, a source of ammonium or alkyl ammonium ions, and a retinol derivative, (3) a diacyl glyceride, lecithin, and a bile acid salt, or (4) (a) a diacyl glyceride, (b) lecithin, and (c) a mucin hydrolysis product or a proteoglycan hydrolysis product, which has at least one of the following properties:

(a) is capable of stimulating monocytes and macrophages in vitro to produce one or more cytokines;

(b) is capable of stimulating monocytes or macrophages to produce tumor necrosis factor in vitro or in vivo; or (c) has an anti-proliferative effect in a malignant mouse hybridoma cell line.

The following non-limiting examples are illustrative of the present invention:

EXAMPLE 1

Preparation of the Composition of the Invention

Bovine bile is collected from healthy herds at least one and one half years old which have been slaughtered for food use at a licensed and inspected abattoir. The gall bladders are collected from the slaughtered animals which have been inspected and the gall bladders are separated from the livers and examined by a veterinarian to confirm that the gall bladders are free of parasites and evidence of infection, and thus are suitable for use as a source of bile.

Gall bladder which pass this inspection are wiped with a solution of 70% ethanol to sanitize the exterior and a syringe is inserted to remove the bile. The bile removed is visually examined by the veterinarian in the syringe to assure that it contains no blood or pus and is otherwise satisfactory. Bile found to be satisfactory is transferred into a graduated amber bottle containing ethyl alcohol. The bile is a greenish fluid substantially free of blood and pus. Bile is added to each bottle to a level marked on the bottle, twice the level of ethanol present to give a 50% bile/ethanol solution. The bile/ethanol solution is a greenish fluid substantially free of foreign material in an approximate 50%/50% bile/ethyl solution. It also shows positive for ethyl alcohol USP XXII Part B. These bottles are labelled with the date of collection which serves as the lot number. A minimum of fifty animals serve as the pool for each lot. Fragments of livers, spleen, and lymph nodes are also collected from the animals whose bile made up the pool and the fragments are examined for the presence of parasites or other indications of disease.

The bile/alcohol mixture is then centrifuged at 4200 RPM for at least 2 ½ hours at 20 +/−2° C. The supernatant liquid is decanted and checked for pH and ethanol content. The decanted liquid is then subjected to an activated charcoal treatment. The treated bile/ethanol is then monitored for Optical Density ("O.D.") and conductivity. O.D. levels or conductivity levels outside acceptable specifications will require that the bile ethanol solution be given additional treatment with activated carbon to achieve a reading within specification limits.

Following activated carbon treatment, the solution is filtered through a filter (for example using filters having a 2.5 μm retention), the alcohol is evaporated off (for example, by heating to less than 85° C.) and the solution is concentrated to approximately one eighth of the original bile/ethanol solution volume. The concentrated solution is cooled to 20–25° C. This solution is then mixed with ethyl ether and the ether phase is discarded. This step may be repeated once. The aqueous phase is heated to remove residual ether (for example by heating up to about 55° C. for about 10 hours) and further reduced in volume to one tenth of the original bile/ethanol volume by heating to about 80–85° C. The resultant composition is then tested for appearance, biological activity and ethanol and ether content. The composition is a clear yellowish solution essentially free of foreign matter, and it contains not more than 10 ppm ethanol and not more than 5 ppm ether. In the bioassay described in Example 4, the non-proliferative growth is 18 +/−Units/ml.

Identity and purity are determined using reverse-phase high pressure liquid chromatography. Potency is assayed using the antiproliferative method as described in Example 4.

Initial batches of the composition of the invention were manufactured as a non-buffered liquid. Subsequent batches were manufactured as a buffered liquid, prepared by adjusting the pH of the composition to about 7.4 +/−0.05, using hydrochloric acid (1%) solution and sodium hydroxide (1% solution), as well as using dibasic and monobasic sodium phosphate salts as buffers. Bioburden reduction is conducted in a steam autoclave at 104 +/−2° C. for 60 minutes. The bulk solution is filled into 5 ml or 10 ml sterile bottles and capped. The filled and capped bottles are subjected to three sterilization cycles by autoclaving them at 104° C. +/−2° C. for 60 minutes followed by incubation at 35° C. for 23 +/−1 hrs. Between each cycle (autoclave plus incubation samples) are taken and tested for bioburden. Following the last cycle, the bottles are visually inspected against a black and a white background to detect any particulates which may be present.

Following inspection, the lot is sampled and tested for conformance to specifications. Tests include identity, sterility, pyrogenicity, endotoxin, bioassay, HPLC and general safety (See Table 1).

TABLE 1

Results for Individual Batches

|  | BATCH # BC0226 | BATCH # BC0227 | BATCH # BC0228 |
|---|---|---|---|
| FINAL PRODUCT TEST |  |  |  |
| Biological Activity (18.0 +/− 5 units/ml) | 17 | 14.0 | 22.5 |
| Identity/Purity Agrees with reference | Pass | Pass | Pass |
| Safety (Passes test) | Pass | Pass | Pass |
| Pyrogeniticy (temp. increase shall not exceed 0.4° C.) |  |  |  |

TABLE 1-continued

Results for Individual Batches

|  | BATCH # BC0226 | BATCH # BC0227 | BATCH # BC0228 |
|---|---|---|---|
| Endotoxin ≦ 0.4 EU/ml | ≦0.25 | ≦0.25 | ≦0.25 |
| Sterility (no growth) | Pass | Pass | Pass |
| pH (7.40 +/− 0.05) | 7.45 | 7.39 | 7.36 |
| Appearance - Visual (clear, light yellowish liquid with little or no precipitate) | Pass | Pass | Pass |
| Appearance - O.D. (passes test) | 0.088 | 0.118 | 0.088 |
| Osmolarity | 540 | 603 | 445 |
| IN-PROCESS TEST |  |  |  |
| Solids (18 +/− 3 mg/ml) | 18 | 15 | 20 |
| Amino Acids (800 +/− 10% mg/ml) | 790 | 742 | 878 |
| Ethyl Alcohol (not more than 10 ppm) | Pass | Pass | Pass |
| Ethyl Ether (not more than 10 ppm) | Pass | Pass | Pass |
| Conductivity (26 +/− 5 mMHO) | 25 | 22 | 29 |

EXAMPLE 2

Physical Chemical and Biochemical Characteristics of the Composition of the Invention A number of the physicochemical characteristics of the preparation (conductivity, osmolarity and total solids) are shown in Table 2. More particularly, test results for three manufactured batches of a composition prepared in accordance with Example 1 were carried out. The results shown in Table 2 demonstrate the sterility, potency, and reproducibility of the manufactured product. It is noted that the ethyl alcohol and ethyl ether are measured as in-process tests only. A summary of the method for determination of the biological activity is provided in Example 4.

TABLE 2

Product Specification

| Test | Specification | Method |
|---|---|---|
| Biological Activity | 18 +/− 5 units/ml | Biological Activity |
| Identity/Purity | Agrees with reference | HPLC |
| Safety | Passes test | General safety test (mice and guinea pigs) 21 CFR part 610.11 |
| Pyrogenicity | Temperature increase shall not exceed 0.4° C. | Pyrogen test (rabbits) USP |
| Endotoxin | <2 EU/ml | Limulus Amoebocyte Lysate Test USP |
| Sterility | No growth | Sterility Test USP |
| pH | 7.40 +/− .05 | pH test USP |
| Appearance | Clear, light yellowish liquid with little or no precipitate | Visual Inspection |
| Solids | 18 +/− 3 mg/ml | Lyophilization |
| Amino Acids | 800 +/− 10% ug/ml | Trinitrobenzene-sulfonic Acid Method |
| Osmolarity |  | Freezing point depression USP |
| Ethyl Alcohol | Not more than 100 ppm | Direct Injection Gas Chromatography |
| Ethyl Ether | Not more than 100 ppm | Direct Injection Gas Chromatography |
| Conductivity | 26 +/− 5 mMHO | Copenhagen Radiometer Model |

Physical and chemical properties such as conductivity, osmolarity and total solids are consistent with a composition of over 99% salt. Less than 1% of the solids in the composition is organic material, there are no lipids, around half are carbohydrates and the rest are amino acids. Proteins and peptides are present. SDS Gel electrophoresis confirmed that there may be more peptides than proteins in the compositions. High molecular weights are not detected. This is an important feature of a peptide drug because it is not expected to be immunogenic.

HPLC and bioassay test methods for the composition of the invention were developed using the nonbuffered product. These tests are used to characterize the product as the buffered liquid and the concentrated formula. The HPLC results described below indicate that the product is the same in all of the presentations. The bioassay shows that the activity of the concentrated composition is two and a half times greater than the original composition. Therefore, the product used in the studies has been demonstrated as being equivalent.

Reversed Phase ($C_{18}$) HPLC Analysis of the Composition of the Invention

The composition of the invention has a consistently reproducible pattern on reversed phase HPLC in which peaks are seen early in the exclusion fraction and at about 27 and 32 minutes. Before, in-between and after the tall peaks, there are smaller peaks that vary in intensity. The HPLC readings for three lots of the concentrated composition of the invention are shown in FIGS. 1 to 3. RP-HPLC profiles for batches B0211 (FIG. 4), B0209 (FIG. 5), B29/3006 (FIG. 6) and B15/1606 (FIG. 7), also show a very reproducible pattern.

The RP-HPLC to characterize the composition of the invention was carried out as follows. Bio-Rad Hi-Pore RP 318 guard column ($C_{18}$), 4.6×30 mm (Bio-Rad) and Bio-Rad Hi-Pore RP 318 ($C_{18}$) column, 4.6×250 mm was used. The samples were dialyzed in 0.1% trifluoroacetic acid (TFA Pierce) in $H_2O$ (Buffer A) and applied to the column. Buffer A was run for 10 minutes, then a linear gradient 0–80% of Buffer B (0.1% TFA in 100% acetonitrile) was run for 55 minutes. At the end of this period, 80% Buffer B was run for 5 minutes and 80–0% of Buffer B for 5 minutes. Flow rate was 1.0 ml/minutes. Fractions from successive runs were collected and pooled and concentrated in a Speedvac (Model SVS 200H, Savant Instruments, Farmington, N.Y.)

Preliminary Characterization of the Composition

Peaks from HPLC were submitted for protein sequencing. The initial sample, the major HPLC peak designated RP-HPLC –31.00 min, batch 0210 in TFA/$CH_3CN$, failed to yield data when subjected to N-terminal sequence analysis. The results may be interpreted as either a quantity problem or N-terminal blockage. Quantitation of protein content of that fraction by amino acid analysis after acid hydrolysis revealed that sufficient quantity should have been subjected to sequence analysis; however, because of the composition it was thought the sample may not be a protein and thus N-terminal blockage would not be the problem. The samples displayed the following composition: about 70% Glx (glutamate/glutamine) plus about 15% glycinen (Gly). Furthermore, analysis of the equivalent sample from RP-HPLC gave similar results: 68% Glx and 15% Gly (Table 3). Further characterizations of unfractionated material plus several other fractions revealed the following. The starting material (32 mg/ml) yielded a sequence signal indicating a polyglutamate peptide/protein, consistent with the amino acid composition data.

TABLE 3

Mole % Glx Gly - HPLC Fraction run R1 (see profile)

| Fraction # | Analysis # (July 11, 1992) | Mole % Glx | Mole % Gly | SUM Glx + Gly |
|---|---|---|---|---|
| 1a | 393 | 28 | 44 | 72 |
| 1b + c | 394 | 35 | 37 | 72 |
| 2a | 395 | 39 | 36 | 75 |
| 2b | 396 | 35 | 43 | 78 |
| 2c | 397 | 44 | 30 | 74 |
| 3a | 398 | 69 | 21 | 90 |
| 3b | 399 | 70 | 10 | 80 |
| 3c | 400 | 52 | 18 | 70 |
| 4 | 401 | 68 | 15 | 83 |
|  | 402 | 48 | 30 | 78 |

Analysis of several HPLC fractions (Table 3) revealed that all are very rich in Glx (Glu/Gln) (28–70 mol %) and Gly (10–44 mol %). Each fraction, however, displayed real differences in the relative amounts of the other amino acids.

EXAMPLE 3

Biological Activity of Fractions of the Composition

The biological activity of fractions of the composition have been investigated. The biological activity of the composition is thought to be attributable to small molecular weight components (m.w. less than 3000 daltons). This was determined through an experiment in which four fractions of the composition and unfractionated composition were tested for biological activity. The first fraction contained proteins and peptides with molecular weight less than 3000 daltons, while the remaining three fractions contained additional larger molecular weight proteins and polypeptides. All fractions contained additional larger molecular weight proteins and polypeptides. All fractions and unfractionated compositions demonstrated the same biological activity. Since all fractions were as effective as the unfractionated product, and since the common denominator of all fractions was the presence of the same concentration of molecules smaller than 3000 daltons, this led to the conclusion that the biological activity of the composition is due to components with molecular weights smaller than 3000 Daltons.

EXAMPLE 4

Effect on Malignant Cell Lines

The effect of the composition of the invention on the proliferation of cultures of four malignant cell lines (Daudi-human lymphoma cells, ME-180 human cervical carcinoma cells, T-24-human bladder carcinoma cells, and mouse hydridoma cells #6-1) was measured. The composition of the invention had an antiproliferative effect on the mouse hydridoma cells. The studies suggested that the inhibitory effect of the composition in mouse hydridoma cells is antiproliferative rather than cytocidal.

A bioassay based on the reproducible antiproliferative effect of the composition of the invention was designed in a mouse hydridoma cell model to facilitate characterization of the composition. The bioassay is carried out as follows. The osmolarity and pH of the composition are adjusted to match that of the cell culture medium in order to isolate the composition's biological activity from its physical and chemical properties. Serial dilutions of isotonic composition from 1:5 to 1:10,000 are prepared in culture medium.

Hybridoma cell samples are specifically quantitated. Using a hemocytometer the cells in a 100 µl sample are counted. The cells are concentrated by centrifugation and then cell concentration is adjusted to 1,000 cells/ml (twice the final desired concentration) by addition of appropriate volumes of fresh media. Hybridoma cell suspensions (1 ml) mixed with corresponding dilutions of the composition (1 ml) are incubated in 24 well plates at 37° C. in a humid atmosphere with $CO_2$ controlled at 6. After 96 hours, each well is sampled at 100 µl×3 and placed in a 96 well plate. (A blank of 100 µl of medium without cells is included.) Cell density is determined using a PROMEGA CellTiter 96™ kit. Cell concentration is measured by reading absorbance at 595 nm (650 nm reference) and recorded by ELISA plate reader. For each assay, a standard curve of cell concentration is prepared. Cultured cells in the log phase of growth are sampled, counted, concentrated and resuspended in serial dilutions. Each dilution is sampled at 100 µl×3 and placed in a 96 well plate. The standard curve is constructed by plotting cell density versus "net" OD at 595 nm after subtraction of zero cell blanks and OD at 650 nm. Cell density of unknown samples is determined by interpolation.

To calculate biological activity, cell density as a percentage of the control (no composition) is plotted against final composition dilution (in log and linear scale), and a curve is fitted through the points utilizing the Spline curve fitting method. Then, the composition dilution that corresponds to 50% inhibition of cell proliferation is determined manually and converted directly to UNITS of composition. By definition, one unit of composition inhibits by 50% the proliferation of 1 ml cell culture of cell line HYB #6-1, seeded at 500 cells/ml, after 96 hours at 37° C. and 6% $CO_2$. The average activity of the composition of the invention in the bioassay is 18.24 +/−1.82 Units/ml.

EXAMPLE 5

Effect on T and B Lymphocytes in Cultures

The composition of the invention has been shown to be non-toxic to normal T and B lymphocytes in culture. The growth of human lymphocytes was examined under carefully controlled conditions in the presence and absence of the composition. Standard concentrations of lymphocytes were incubated in wells containing various concentrations of the composition. When normal T and B human lymphocytes were incubated with the composition in concentrations similar to those that are used clinically, there were no adverse effects as judged by Trypan Blue exclusion.

The effect of the composition on the survival of human peripheral blood mononuclear cells (PBMN) was examined. In this experiment, PBMN were incubated for 24 and 48 hrs in plastic microwell plates with various volumes of the composition and tissue culture medium. At the end of this period, the number of surviving cells was estimated by trypan blue dye exclusion. Table 4 shows that the number of surviving cells fell at 24 and again at 48 hours; however, the number of surviving cells in the presence or absence of the composition was not different. Moreover, increasing volumes of the composition had no effect on survival (Table 4). Thus, the composition showed no cytotoxicity to human PBMN.

TABLE 4

Concentrations of Viable PBMN After Incubation

| | | No. of live PBMN per Well by Trypan Blue (×10$^6$)[1] | |
|---|---|---|---|
| Concentration (µl/well) | Zero time | After 24 hrs No. % viable | After 48 hrs No. % viable |
| Patient S. Z. | | | |
| 0 | 0.70[2] | 0.23 (33) | 0.10 (14) |
| 25 | | 0.43 (61) | 0.15 (21) |
| 50 | | 0.10 (14) | 0.23 (33) |
| 100 | | 0.15 (21) | 0.18 (26) |
| 200 | | 0.48 (69) | 0.23 (33) |
| LPS (µg/well) | | | |
| 1 | | 0.30 (43) | 0.28 (40) |
| 10 | | 0.25 (36) | 0.13 (18) |
| Patient E. S. | | | |
| 0 | 1.30[2] | 0.70 (54) | 0.33 (25) |
| 25 | | 0.65 (50) | 0.15 (12) |
| 50 | | 0.68 (52) | 0.38 (29) |
| 100 | | 0.75 (58) | 0.23 (18) |
| 200 | | 0.65 (50) | 0.20 (15) |
| LPS (µg/well) | | | |
| 1 | | 0.60 (46) | 0.53 (41) |
| 10 | | 0.15 (12) | 0.15 (12) |

[1]Approximately 1 × 10$^6$ cells plated/well in triplicate.
[2]Actual number of cells counted/well (×10$^6$).

EXAMPLE 6

Cytokine Content of Composition

ELISA assays for TNF-α, IL-1a, IL-2, IL-4, IL-6, IL-8, GM-CSF and IFN were conducted on the composition of the present invention. It was determined that the composition of the invention contained no measurable levels of cytokines (TNF, IL-1 alpha, IL-1 beta, IL-4, IL-6, IL-8, GM-CSF and IFN gamma) (See Table 5).

TABLE 5

ELISA DETERMINATION OF CYTOKINES IN COMPOSITION

| | COMPOSITION | |
|---|---|---|
| Cytokine | 50 µl | 100 µl |
| TNF pg/ml | <5 | <5 |
| | Detection Limit: 5 pg/ml | |
| IL-1β pg/ml | — | 6.5 |
| | Detection Limit: 4.3 pg/ml | |
| GM-CSF pg/ml | >5 | — |
| IL-6 pg/ml | <7 | — |
| | Detection Limit: 7 pg/ml | |
| IFNγ pg/ml | <5 | — |
| | Detection Limit: 5 pg/ml | |
| IL-1α pg/ml | <50 | — |
| | Detection Limit: 50 pg/ml | |
| IL-4 pg/ml | — | <3 |
| | Detection Limit: 3 pg/ml | |
| IL-8 ng/ml | Detection Limit: 4.7 ng/ml | <4.7 |

EXAMPLE 7

Physical, chemical, and biological properties, were determined for a number of batches of the composition of the invention prepared in accordance with the method as described in Example 1. In addition, the chemical composition of the batches was determined and an amino acid analysis of the batches was conducted. The results are shown in Tables 6–8.

TABLE 6

| | CHEMICAL COMPOSITION | | | | High M.W. | PHYSICAL, CHEMICAL AND BIOLOGICAL PROPERTIES | | | | | |
|---|---|---|---|---|---|---|---|---|---|---|---|
| Batch No. | Solids mg/ml | Amino Acids μg/ml | Sugars μg/ml | Lipids μg/ml | >3 kD PROT μg/ml | pH | Conduct. mMHO | Osmolar. mOsM | Absorban. O.D. 280 nm | UV, VIS Peaks | Activity Units/ml |
| B0201 | 15.3 | 4.59 | 40.85 | ND < 0.5 | NA | 7.37 | 16.9 | 361 | 0.98 | 404 nm | 10.5 |
| B0202 | 15.7 | 13.16 | 54.95 | ND < 0.5 | NA | 7.35 | 17.3 | 298 | 0.777 | None | 6.5 |
| B0203 | 15.0 | 72.67 | 25.5 | ND < 0.5 | NA | 7.3 | 17.7 | 360 | 0.67 | 365 nm | 21.0 |
| B0208 | 7.8 | 4.53 | 30 | ND < 0.5 | ND < 1.0 | 7.00 | 16.1 | 250 | 0.453 | None | 8.1 |
| B0209 | 8.5 | 2.27 | 24 | ND < 0.5 | ND < 1.0 | 7.31 | 11.2 | 259 | 0.594 | None | 6.7 |
| B0211 | 5.6 | 1.47 | 19.2 | ND < 0.5 | ND < 1.0 | 7.35 | 34.9 | 175 | 0.287 | None | 7.5 |
| B0106 | 32.2 | 1.16 | 32.6 | ND < 0.5 | ND < 1.0 | 7.57 | 34.3 | 627 | 0.341 | None | 17.2 |
| B0706 | 32.7 | 1.42 | 26.2 | ND < 0.5 | ND < 1.0 | 7.57 | 11.6 | 627 | 0.387 | None | 23.0 |
| B1306 | 22.3 | 8.01 | 48 | ND < 0.5 | ND < 1.0 | 8.02 | 35.6 | 790 | 1.147 | None | 17.0 |
| B2006 | 21.7 | 9.73 | 38.4 | ND < 0.5 | ND < 1.0 | 8.56 | 33.9 | 651 | 1.024 | None | 21.0 |
| B2306 | 28.5 | 16.35 | 42 | ND < 0.5 | ND < 1.0 | 8.01 | 35.1 | 623 | 1.054 | None | 19.0 |

Comments:
1. To batches No. B0106 and B0706 full isotonic PBS solids were added.
2. Batches B1306, B2006 & B2306 were concentrated X2, no pH adjustment.

TABLE 7

| | CHEMICAL COMPOSITION | | | | High M.W. | PHYSICAL, CHEMICAL AND BIOLOGICAL PROPERTIES | | | | | |
|---|---|---|---|---|---|---|---|---|---|---|---|
| Batch No. | Solids mg/ml | Amino Acids μg/ml | Sugars μg/ml | Lipids μg/ml | >3 kD PROT μg/ml | pH | Conduct. mMHO | Osmolar. mOsM | Absorban. O.D. 280 nm | UV, VIS Peaks | Activity Units/ml |
| B0213 | 31.6 | 21 | 61 | ND | ND | 7.75 | 29.5 | 628 | 0.48 | none | 14.5 |
| R0201/−pH | 52.5 | 1553 | 216 | ND | ND | 7.95 | 44.5 | 877 | 1.59 | 271 nm 0.65 O.D. | 51.5 |
| R0201/+pH | 55.8 | 1530 | 280 | ND | ND | 7.60 | 50.0 | 1162 | 2.29 | 266nm 1.6 O.D. | 61.5 |
| C0203 | 36.1 | 113 | 42 | ND | ND | 7.90 | 34.8 | 657 | 0.96 | none | 5.0 |
| 0-13/2109 | 12.1 | 149 | 36 | ND | ND | 7.73 | 17.0 | 316 | 0.83 | none | 14.5 |
| B27/2806 | 17.5 | 28 | 37 | ND | ND | 7.71 | 22.0 | 453 | 0.49 | none | 12.4 |
| B29/3006 | 28.7 | 26 | 60 | ND | ND | 7.67 | 28.8 | 605 | 0.55 | none | 14.0 |
| B15/1606 | 26.8 | 41 | 45 | 75 | ND | 7.84 | 35.0 | 753 | 1.04 | none | 14.0 |

TABLE 8

AMINO ACID COMPOSITION

| | Batch # | | | | | | | |
|---|---|---|---|---|---|---|---|---|
| | B-0208 | B-0209 | B-0211 | 01/06 | 07/06 | 1306 | 2006 | 2306 |
| Asparagine | 365 | | | | 113 | | 119 | 289 |
| Serine | | 69 | 12 | 7 | 17 | 144 | | 308 |
| Glycine | 22 | 449 | 274 | 279 | 417 | 3731 | 5314 | 10371 |
| Histidine | | 192 | | 90 | 68 | 938 | 1335 | 2114 |
| Arginine | | | | 161 | 533 | | | |
| Threonine | | 19 | 13 | | 30 | 148 | 142 | 250 |
| Alanine | | 173 | 112 | 24 | 64 | 949 | 1002 | 1423 |
| Proline | 1092 | | | | 74 | 817 | 639 | 1075 |
| Tyrosine | 15 | 55 | 57 | 43 | 39 | 205 | 135 | 45 |
| Valine | 121 | 63 | 31 | 10 | 15 | 367 | 335 | 224 |
| Methionine | | 970 | 461 | 462 | 13 | 107 | 121 | 70 |
| Cysteine | | 103 | 90 | 41 | 12 | 86 | 49 | 10 |
| Isoleucine | 2721 | 84 | 95 | 17 | | 232 | 216 | 68 |
| Leucine | | 58 | | | 9 | 221 | 242 | 84 |
| Phenylalanine | | 57 | 200 | 16 | | 45 | 80 | 23 |
| Lysine | 191 | 36 | 123 | 6 | 18 | 15 | | |
| Total AA μg/ml | 4.53 | 2.27 | 1.47 | 1.16 | 1.42 | 8.01 | 9.73 | 16.35 |

EXAMPLE 8

Activation of Monocytes and Macrophages

Investigations have shown that the composition of the invention will activate normal monocytes to demonstrate cytotoxicity towards the Chang hepatoma cell line which is used to measure monocyte toxicity and that the monocytes and macrophages from cancer patients (cervical and ovarian cancer) have been stimulated by the composition to attack and destroy their own particular tumor cells.

More particularly, the monocyte tumoricidal function has been tested in the presence of the composition of the invention and the basic procedure for these experiments is outlined below.

Venous blood is collected in heparinized vacutainer tubes. The blood is diluted 3:1 in Hanks balanced salt solution (HBSS) layered onto lymphocyte separation medium and centrifuged to obtain a band of peripheral blood mononuclear cells (PBMN). After centrifugation, the mononuclear cell layer is recovered from the interface washed twice in medium and monocytes are enumerated by latex ingestion. Nonocytes are isolated by adherence in 96 well plates (for 2 hours at 37° C. followed by two cycles of washing). Adherent cells are estimated to be greater than 90% monocytes. Wells containing adherent cells are incubated overnight in the presence of the composition 11:10 dilution) granulocytemacrophage stimulation factor or PMA. Then adherent cells are washed and incubated overnight with tumor cells. For studies using a standard cell line $^{51}$CR-labelled Change hepatoma cells are used because this cell line is insensitive to natural killer cell cytotoxicity. These hepatoma target tumor cells are added to adherent cell monolayers at an effector:target (E:T) cell ratio of 20:1. This E:T ratio is used because it falls well into the plateau range on a curve prepared by varying the E:T ratio from 5:1 to 30:1.) After 24 hours supernatants are collected and $^{51}$Cr release is quantitated. The percent specific cytotoxicity is calculated as:

% specific release=(E-S)/(T-S)×100 where E=CPM; S=CPM released from target cells in the presence of effector cells; S=CPM released from target cells in the absence of effector cells; T=CPM released from target cells after treatment with 2% sodium dodecyl sulfate.

Using this protocol, the composition was found to cause monocytes from healthy donors to exert cytotoxicity toward the Change hepatoma cell line. Subsequently, whether monocytes and macrophages from a cancer patient could be stimulated by the composition to attack and destroy their own particular tumor was investigated. Using similar protocols as described for the standard cell line (Chang hepatoma cells), monocytes and/or peritoneal macrophages from cancer patients were isolated. (Peritoneal macrophages were isolated from peritoneal fluids collected at the time of laparoscopy). The composition was found to activate peripheral monocytes and peritoneal macrophages from a patient with cervical cancer to produce cytotoxicity against the patient's own tumor cells. This effect was comparable to or better than that produced by interferon or lipopolysaccharide. Peritoneal macrophages from a patient with ovarian cancer were also found to be stimulated by the composition to attach destroy the ovarian tumor cells in culture.

EXAMPLE 9

Effect on TMF

Studies were conducted to evaluate the effect of the composition of the invention on cytokine release from peripheral blood mononuclear cells (PBMN). ELISA assays for TNF-α, IL-1a, IL-2, IL-4, IL-6, IL-8, GM-CSF and IFN were conducted.

The following methods were used in the studies described in the Example.

In the studies of TNF, whole blood was drawn from 5 healthy subjects into heparinized Vacutainer tubes. Peripheral blood mononuclear cells (PBMNs) were isolated by gradient centrifugation of Ficoll-Hypaque (Pharmacia). The PBMN were washed twice with phosphate buffered saline (PBS), counted and resuspended in RPMI 1640 culture medium (Gibco Labs) at a concentration of $10^6$ cells/0.5 ml. These cells were cultured in 24 well, flat-bottomed tissue culture plates (Falcon, Becton, Dickinson). Of the PBMN suspension, 0.5 ml was added to each well containing 50 ng Lipopolysaccharide (LPS) (from E.coli), 10 μl fetal calf serum and the respective volumes of composition tested 10–300 μl). To neutralize the hyperosmolar effect of the composition, distilled water was added to the culture wells at a volume equivalent to 10% of the volume of composition used. The total volume was then made up to 1 ml/well with RPMI. As control, PBS was used instead of composition. The cells were cultured for 2, 6, 24, 48 and 72 hours at 37° C. in a humidified 5% $CO_2$ incubator. At the end of each incubation period, the cells were harvested and cell free culture fluids were obtained by centrifugation at 9000 rpm for 10 minutes. The samples were then stored at −70° C. until ELISA for cytokines was carried out (within 2 weeks).

Protein estimation of the composition was done using the Pierce Micro BCA Protein determination technique (Smith et al., Anal. Biochem. 1985, 150:76–85). 10 μl of a sample of the composition was made up to 1 ml with distilled water. Five concentrations of Bovine Serum Albumin (0.150 μg/ml) was also made up to be used as standards. As a blank, 0.1N NaOH was used. To all these samples was added a mixture of BCA, 2% Bicinchonic Acid sodium salt) (Pierce), Copper Sulfate 4% and Microreagent Å ($NaCO_3$, $NaHCO_3$, Na tartrate in 0.2N NaOH). The sample mixtures were incubated for 1 hr at 60° C., cooled and the resultant absorbency read at 562 nm using a spectrophotometer. The amount of protein in the test sample was then compared to the plotted standard curve and the appropriate calculations made. The protein concentration of the composition was found to be low and estimated to be 32 μg/ml.

Cytokine synthesis in the supernatants were measured after stimulating human PBMN with the composition of the invention at volumes of 200 and 300 μl/well. The initial preparations of the composition show no stimulatory effect on cytokine production (Table 9). If there was any effect there was the suggestion that cytokine production was below the constitutive level when PBMN were incubated in medium alone.

TABLE 9

Direct Effect of Composition on Cytokine Production after 24 hrs
Amount of Cytokine Released (pg/ml)[1]

| Cytokine Assayed | Medium | Composition 100 μl | Composition 200 μl | LPS 1 μg |
|---|---|---|---|---|
| IL-1α | 61.6 ± 12 | 59.6 ± 7.8 | 54.3 ± 6.0 | 315 ± 117 |
| IL-1β | 199 ± 184 | 218 ± 165 | 188 ± 174 | 965 ± 99 |
| TNF[2] | 203 ± 149 | 151 ± 117 | 107 ± 120 | 1501 ± 284 |
| IL-6 | 928 ± 776 | 853 ± 673 | 829 ± 543 | 2016 ± 41 |
| IL-8 | 126 ± 70[3] | 94 ± 50[3] | 77 ± 41[3] | 361 ± 165[3] |
| GM-CSF | 13 ± 4 | 13 ± 7 | 15 ± 11 | 54 ± 20 |

TABLE 9-continued

Direct Effect of Composition on Cytokine Production after 24 hrs
Amount of Cytokine Released (pg/ml)[1]

| Cytokine Assayed | Medium | Composition 100 μl | Composition 200 μl | LPS 1 μg |
|---|---|---|---|---|
| IFN-γ | 11 ± 18 | 9 ± 14 | 5 ± 6 | 54 ± 94 |
| IL-4 | <3.0 | <3.0 | <3.0 | <3.0 |

[1]Mean of eight patient samples in duplicate
[2]Mean of seven patient samples in duplicate
[3]ng/ml Experiments were performed to determine whether the composition of the invention would impair LPS-stimulated release. LPS was used as a positive stimulus, and the ability of the composition to impair LPS stimulated release of cytokines was compared for the different cytokines (Table 10). The composition clearly inhibits IL-1 alpha, IL-1 beta and TNF. The effects on the other cytokines IL-6, IL-8, IFN-gamma and GM-CSF were not as marked. However, in no instance did the composition tested augment the effect of LPS stimulated release of cytokines.

TABLE 10

Difference between LPS Released Cytokine and LPS plus Composition

| | Stimulant of Cytokine | | |
|---|---|---|---|
| Cytokine Assayed[1] | LPS (50 ng/ml) | LPS + Composition[2] | Mean Difference |
| IL-1α | 129 ± 135 | 77 ± 27 | −52 |
| IL-16 | 1314 ± 723 | 919 ± 460 | −395 |
| TNF | 915 ± 763 | 497 ± 525 | −418 |
| IL-6 | 2320 ± 1081 | 2320 ± 1145 | 0 |
| IL-8 (ng/ml) | 118 ± 62 | 109 ± 56 | −9 |
| IFN-γ | 30 ± 24 | 13 ± 10 | −17 |
| GM-CSF | 54 ± 65 | 50 ± 63 | −4 |

[1]PBMN from six patients were tested in duplicate
[2]Composition batch B0209

Figure 8:
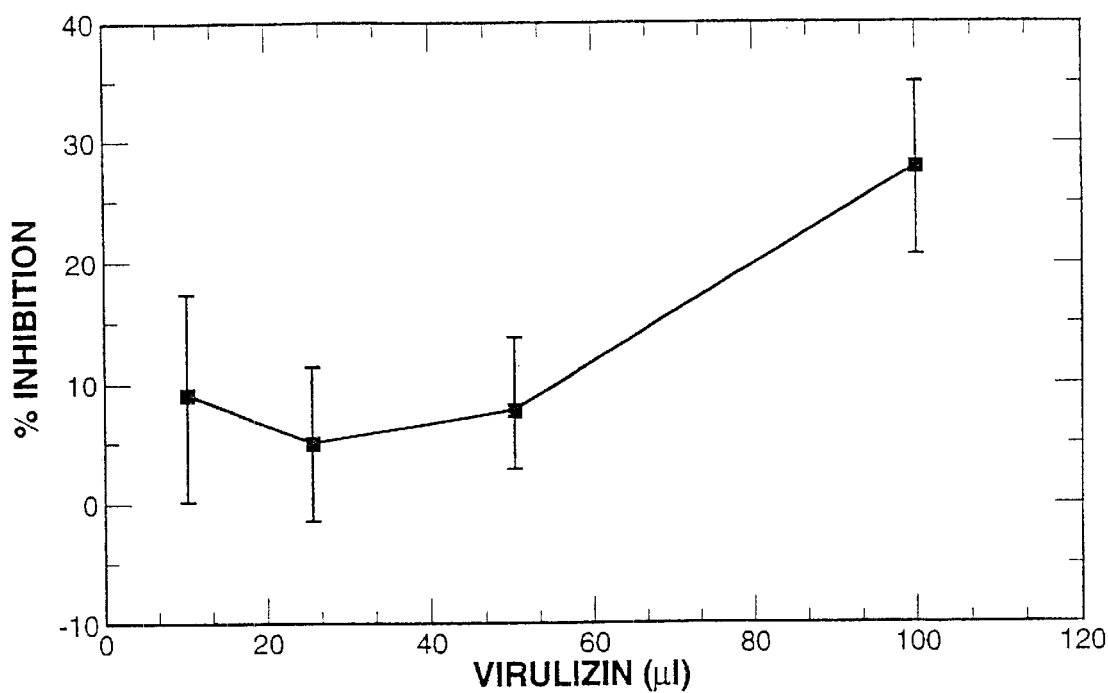
FIG. 8 is a graph showing the effect of the composition on LPS-induced release of TNF by PBMN.

The effect of different volumes of the compositions of the invention in inhibiting LPS stimulated release of TNF was examined. FIG. 8 shows a dose-response curve of the composition inhibiting release of TNF by PBMN stimulated with LPS. Ten μl of the composition inhibited about 10% and increased close to 30% inhibition at 100 μl of the composition. Another batch (B0201) of the composition inhibited LPS-induced TNF production at 200, 100 and 10 μl by 45, 21 and 12 percent, respectively.

Similarly, IL-1 beta production was inhibited in a dose-dependent manner by the composition: 100, 25 and 10 μl of the composition inhibited by 16, 10 and 9 percent, respectively.

Different batches of the composition were examined for their effect on LPS-induced release of TNF. In summary, it was found that batches of the composition produced in the same way and from the same animal induced an identical effect. However, changes in the method of preparation or the composition from different animal species had different effects. Batches B29/3006, B0213 (B=bovine) and C0203 (goat) induced a strong release of TNF above that induced by LPS alone (Table 11).

TABLE 11

Dose-Response Effect on TNF Release of Strong Stimulatory Batches of Composition
Differences in TNFα Release Between LPS + Composition − LPS Alone

| Batch | Composition Volume (μl) | TNF (pg/ml) |
|---|---|---|
| B0213 | 10 | 193 ± 161 |
| | 100 | 858 ± 819 |
| | 200 | 2131 ± 1742 |
| B29/3006 | 10 | 121 ± 102 |
| | 50 | 422 ± 78 |
| | 100 | 834 ± 811 |
| | 200 | 2252 ± 676 |
| C0203 | 10 | 101 ± 47 |
| | 50 | 643 ± 231 |
| | 100 | 2650 ± 1372 |
| | 200 | 1851 ± 980 |

Table 12 shows the results with batches B15/1606 (concentrated preparation) and B27/2806, which were moderately stimulatory.

TABLE 12

Dose Response Effect on TNF Release of Moderate Stimulatory Batches

| Batch | Composition Volume (μl) | Difference in TNFα Release Between LPS + Composition − LPS Alone TNF (pg,ml) |
|---|---|---|
| B27/2806 | 10 | −24 ± 120 |
| | 50 | 71 ± 103 |
| | 100 | 667 ± 844 |
| | 200 | 984 ± 200 |
| B15/1606 | 10 | 299 ± 351 |
| | 50 | 294 ± 145 |
| | 100 | 667 ± 800 |
| | 200 | 1224 ± 446 |

Table 13 shows that batch 013/2109 (sheep) was minimally stimulatory.

TABLE 13

Dose-Response Effect on TNF Release of Minimal Stimulatory Batch

| Batch | Volume (μl) | Difference in TNFα Release Between LPS + − LPS Alone TNF (pg/ml) |
|---|---|---|
| 013/2109 | 50 | −9 ± 73 |
| | 200 | 179 ± 162 |
| | 300 | 178 ± 373 |

Table 14 shows that batch R0201 (shark) was inhibitory at most concentrations for LPS-induced TNF production.

TABLE 14

Dose-Response Effect on TNF Release of Inhibitory Batch

| Batch | Volume (μl) | Difference in TNFα Release Between LPS + − LPS Alone TNF (pg/ml) |
|---|---|---|
| R0201 | 50 | 145 ± 256 |
| | 200 | −370 ± 385 |
| | 300 | −400 ± 185 |

Initially, the composition was shown to affect LPS-induced release of TNF from human PBMN. Thus, in the next series of experiments, the time effect of the composition on LPS-induced release of TNF was examined (Table 15). LPS stimulated release of TNF. By 2 hours the level had risen to 697 pg/ml and peaked at 6 hrs at about 2006 pg/ml. At 24, 28 and 72 hrs the release of TNF progressively fell. In fact, by 48 and 72 hrs, the TNF release was just above constitutive production levels. By contrast, Batch 0213 of the composition, which was strongly stimulatory for TNF release, showed no release of TNF above that produced by LPS alone at 2 and 6 hrs. Whereas LPS induced peak release of TNF at 6 hrs, the composition in combination with LPS induced peak release at 24 hrs at a time when the stimulatory effect of LPS had begun to fall. Unlike LPS alone, composition+LPS continued to stimulate TNF release at 48 and 72 hrs although the quantity of TNF released fell progressively (Table 15). Thus batch 0213 was stimulatory for TNF release. Batch B15/1606, which was only moderately stimulated, inhibited LPS-induced release at 2 and 6 hrs. At 24 hrs, B15/1606 in combination with LPS was mildly stimulatory for TNF-release. At 48 and 72 hrs, B15/1606 in combination with LPS, had a mild stimulatory effect on TNF release. Thus, batch B15/1606 had a biphasic effect; early it inhibited LPS induced TNF release, and mainly at 24 hrs combination with LPS, had a mild stimulatory effect on TNF release. Thus, batch B15/1606 had a biphasic effect; early it inhibited LPS induced TNF release, and mainly at 24 hrs it caused a mild additive effect in conjunction with LPS in inducing TNF-release.

TABLE 15

Time Effect on Different Batches on TNF Release by LPS
Mean Difference in TNFα (pg/ml)
Release Between LPS + Composition
LPS Alone by Three Different Batches

| Time (hr) | TNF Released by LPS (50 ng/ml) | BO213 | B15/1605 | R0201 |
|---|---|---|---|---|
| 2 | 697 ± 94 | 693 ± 339 | 363 ± 189 | 62 ± 42 |
| 6 | 2006 ± 736 | 1949 ± 422 | 1080 ± 377 | 430 ± 260 |
| 24 | 800 ± 222 | 2301 ± 658 | 876 ± 351 | 343 ± 183 |
| 48 | 170 ± 149 | 1419 ± 447 | 234 ± 183 | 129 ± 78 |
| 72 | 132 ± 147 | 945 ± 367 | 184 ± 107 | 153 ± 68 |

Batch R0201, which was inhibitory for LPS-induced release of TNF, was markedly inhibitory for LPS induced TNF release at 2, 6 and 24 hrs. At 48 and 72 hrs, LPS induced minimal TNF release and batch R0201 had minimal positive or negative affects at these times.

The direct stimulatory effect of Batch B0203 was tested at different volumes and then at different times.

Batch B0203 stimulated maximum TNF-release at about 100 μl (Table 16). The maximum effect was observed at 24 hrs for a volume of 200 μl (Table 17). Thus, the composition was able to stimulate TNF-release on its own, that is in the absence of LPS and the curves for TNF-release were similar to when the composition and LPS were combined. It appears that the composition by itself was less stimulatory for TNF release than the additive effect it had when combined with LPS.

TABLE 16

Dose-Response of Batch B0203 on Stimulating Release of TNF

| Volume (pg/ml) (μl) | Mean Amount of TNF Released at 24 hrs |
|---|---|
| None (PBS 50 μl) | 123 ± 207 |
| 50 | 223 ± 65 |
| 100 | 327 ± 90 |
| 200 | 105 ± 54 |
| 300 | 189 ± 94 |

TABLE 17

Effect of Batch B0203 on Release of TNF over Time

| Time (hrs) | TNF Released[1] (pg/ml) |
|---|---|
| 6 | 47 ± 154 |
| 24 | 106 ± 73 |
| 43 | 20 ± 25 |
| 72 | 13 ± 8 |
| 96 | 5.5 ± 6 |
| 120 | 9.5 ± 2 |

[1]Median

Figure 9:
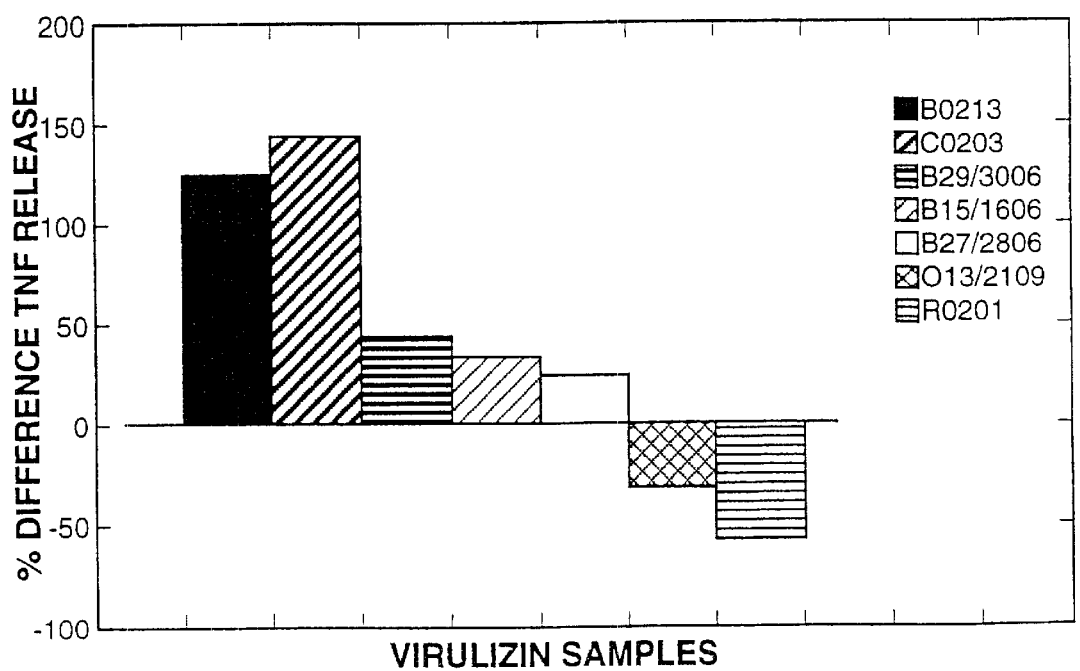
FIG. 9 is a bar graph showing the effect of the composition on LPS-induced release of TNF by PBMN.

In summary, the experimental results indicate that some batches of the composition are able to inhibit TNF release when human PEMN are stimulated with LPS. Other batches have biphasic effects suggesting that they partially inhibit LPS-induced TNF release and have, as a late effect, the ability to induce a mild release of TNF. A third preparation had no inhibitory effect on LPS-induced release of TNF; but at a different time point than LPS, the preparation was able to stimulate human PEMN to release TNF. In conclusion, the composition of the invention can modulate TNF production, an important mediator of antitumor responses. A summary of the data is shown in FIG. 9 and in Table 18.

TABLE 18

TNF Bioassay Results

| Batch No. | RP-HPLC Peaks 1 Min | Source | Normal or Concentrated | Buffer | TNF Release |
|---|---|---|---|---|---|
| B0213 | 27, 32 | Bovine | Normal | Yes | ↑↑ |
| C0203 | 27, 32 | Caprine | Normal | Yes | ↑↑ |
| 013/2109 | 27, 32, 21:50, 25 | Ovine | Concentrated | Yes | ↓/↑ |
| R0201 | 21–25, 28, 29, 29.5, 27, 32 | Shark | Normal | Yes | ↓↓ |
| B29/3006 | ↓27, ↓32 | Bovine | Normal | Yes | ↑↑ |
| B27/2806 | 427, 432 | Bovine | Normal | Yes | ↑ |
| B15/1606 | 27, 32, 22, 28 | Bovine | Concentrated | Yes | ↑ |
|  |  |  |  | Yes | ↓ |

EXAMPLE 10

This Example demonstrates, in summary, the following: The composition has TNF-α releasing activity and the TNF-α releasing activity is not related to any contamination with endotoxin. Priming of macrophages enhances the ability of the composition to stimulate release of TNF-α. The hyperosmolarity of the composition is not responsible for TNF-α releasing activity. The TNF-α releasing activity of the composition can be separated, in part, from other constituents. The TNF-α releasing activity of the composition does not bind or binds poorly to $C_{18}$ RP-HPLC. Most of compositions activity elutes early from RP-HPLC. Less than 20% of the activity of the composition is recoverable from the fractions that are retained on the RP-HPLC and elute later. The TNF-α releasing activity is precipitated by 80% acetonitrile, a high content of organic buffer. The precipitated material when reconstituted in aqueous buffer and analyzed on RP-HPLC shows great similarity to the excluded peak on RP-HPLC of the composition. It is possible to separate and concentrate the active component of the composition in a fraction that constitutes about 30% of the original material.

A. Polymyxin and TNF-alpha Release

To eliminate any possibility of an endotoxin effect of the composition experiments were performed with Polymyxin added to the reactants. Polymyxin inhibits the action of endotoxin on leukocytes. Table 19 shows that polymyxin completely inhibits the LPS-induced release of TNF-α. In the absence of polymyxin, LPS induces 517 pg/ml of TNF-α, whereas in the presence of Polymyxin 11 pg/ml of TNF-α is released. The composition, on the other hand, releases 1591 pg/ml of TNF-α in the presence of Polymyxin. In the absence of Polymyxin, LPS and the composition show more than just an additive effect of the stimulators, suggesting that the composition acts with greater intensity when macrophages are primed.

TABLE 19

Effect of Polymyxin on TNF Release by LPS + Composition

| Sample Tested | Additive | TNF Released (pg/ml) Total | -LPS |
|---|---|---|---|
| LPS | Polymyxin | 11 ± 7 | 0 |
|  | None | 517 ± 118 | 0 |
| Composition (#B0213) | Polymyxin | 1591 ± 413 | 1581 |
|  | None | 5256 ± 2585 | 4738 |

Notes:
1. Total TNF Released is corrected for TNF release by 1640 Medium.
2. Polymyxin concentration: 50,000 units/ml.
3. Composition volume: 200 μl.
4. With polymyxin, 8 patients tested. With no additive, 3 patients tested.
5. LPS concentration: 50 ng/10 μl.

Figure 10:
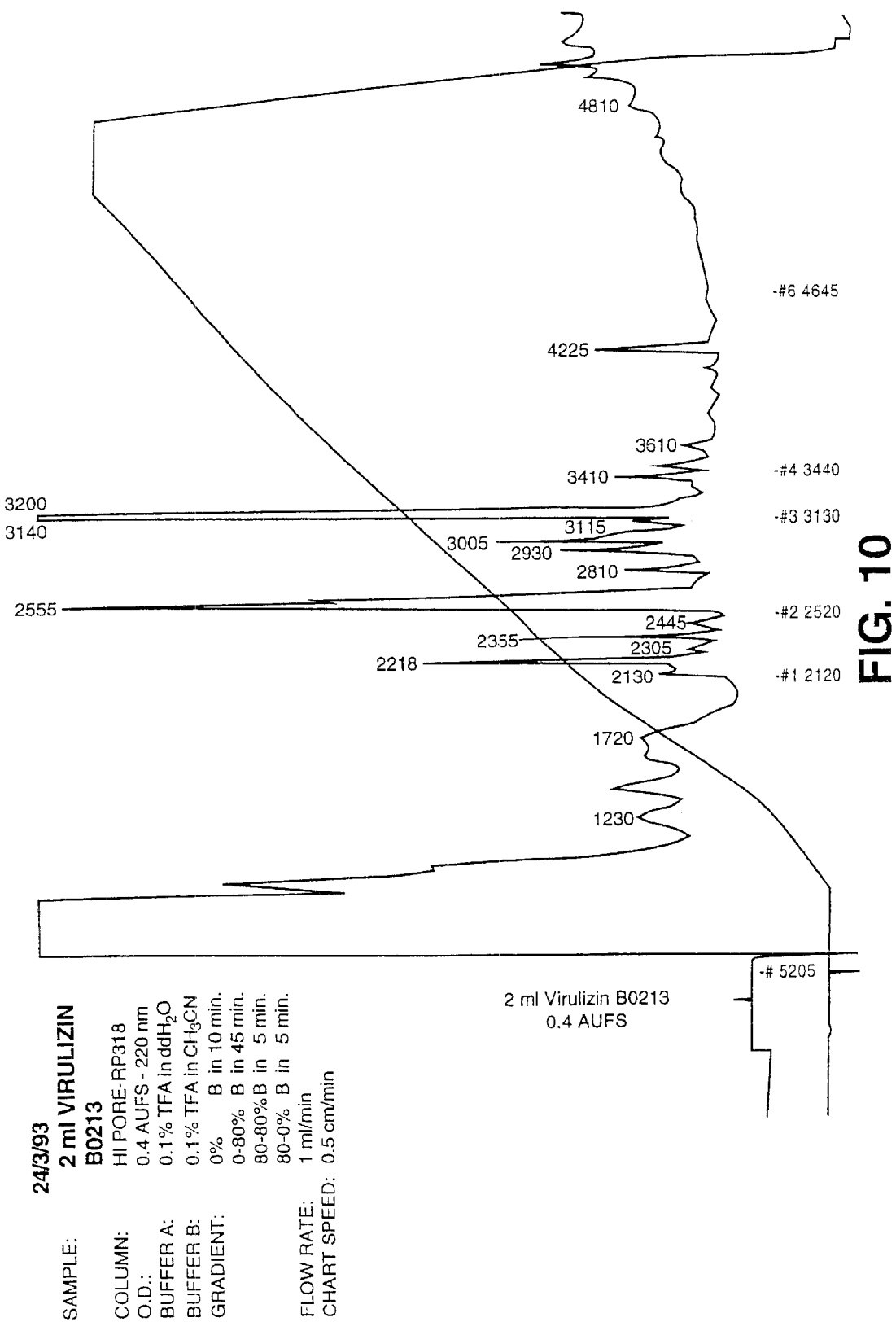
FIG. 10 shows the $C_{18}$ RP-HPLC profile of a composition of the invention.

B. TNF-Releasing Activity of Reversed-Phased High Pressure Liquid Chromatoaraphy (RP-HPLC) Fractions FIG. 10 shows the $C_{18}$ RP-HPLC profile of the composition, Batch 0213 and the 5 separate fractions that were tested for TNF-releasing activity.

Initially, the effect of different fractions were examined in the presence of Polymyxin. Table 20 shows that the early eluting fraction (2:05 to 21:20 minutes) from RP-HPLC had most of the detectable TNF-releasing activity. However, this activity was only about 50% of the starting composition. The right hand column of Table 20 shows the osmolarity of the samples. Batch BO213 was 369 and high. Fractions from 21 minutes and later had normal osmolarity, whereas the first fraction which was active was even more hyperosmolar than the starting material, indicating that much of the salt in the composition also eluted early. Therefore, whether the hyperosmolarity of the samples was inhibiting or enhancing TNF-α release was investigated as set out below.

TABLE 20

Separation and Testing of Different HPLC Fractions of Composition in the Presence of Polymyxia

| Sample Tested | TNF Released (pg/ml) Total | -LPS | Osmolarity (mOsm) |
|---|---|---|---|
| 1640 RPMI Medium | 0 | — | 287 |
| LPS (50 ng/10 μl) | 40 ± 25 | 0 |  |
| Composition #B0213 | 1222 ± 448 | 1182 | 369 |
| Fractions (minutes) |  |  |  |
| 2:05–21:20 | 554 ± 394 | 514 | 434 |
| 21:20–25:32 | 7 ± 7 | 0 | 301 |
| 25:32–31:55 | 0 | 0 | 299 |
| 31:55–34:58 | 4 ± 4 | 0 | 292 |
| 34:58–46:55 | 32 ± 28 | 0 | 295 |

Note:
1. Total TNF Released is corrected for TNF release by RPMI Medium.
2. Fractions are reconstituted in PBS.
3. Volume of composition and fractions: 200 μl.
4. Polymyxin concentration: 50,000 units/ml.
5. Number of patients tested: 5.
6. Osmolarity not measured for LPS.

Table 21 shows additional testing on two patients with composition fractions 1 (2:05–21:20) and 2 (21:20–25.32). Once more, most of the activity was recovered in fraction 1, but there was some activity in fraction 2. However, fraction 1 and 2 had only about 50% of the starting activity of the composition.

TABLE 21

Repeat Evaluation of Composition HPLC Fractions 2:05–21:20 and 21:20–25:32 minutes for release of TNF in the Presence of Polymyxin.

| Sample Tested | TNF Released (pg/ml) Total | -LPS |
|---|---|---|
| 1640 RPMI Medium | 0 | — |
| LPS (50 ng/10 μl) | 31 ± 31 | 0 |
| Composition #B0213 | 2013 ± 726 | 1983 |
| Fractions (minutes): |  |  |
| 2:05–21:20 | 526 ± 126 | 496 |
| 21:20–25:32 | 132 ± 108 | 101 |

Note:
1. Total TNF Released in corrected for release by RPMI Medium.
2. Fractions are reconstituted in PBS.
3. Volume of composition and fractions: 200 μl.
4. Polymyxin concentration: 50.000 units/ml.
5. Number of patients tested: 2

To determine whether there was any non-specific activity in the fractions, a blank run, was made and the same fractions were collected, concentrated and tested. The blank fractions produced virtually no TNF release. This result indicated that fractions from RP-HPLC could be used to test for TNF-α releasing activity without concern that the column or buffers contributed to TNF-α releasing activity.

Next the fractions of the composition were tested in the absence of Polymyxin in order to have the priming effect of LPS. Table 22 shows that Batch BO213 induced a marked release of TNF-α. There were 5 fractions of the composition from the RP-HPLC, with the elution times as indicated. Once again, fraction 1 had the most TNF-α releasing activity. However, with the priming effect of LPS, fractions 2 through 4 had some TNF-α releasing activity. Fraction 2 (21:20–25:32) had about 25% of the activity of fraction 1, and double the activity of the later fractions.

TABLE 22

Separation and Testing of HPLC Fractions of
Composition in the Absence of Polymyxin.

| Sample Tested | TNF Released (pg/ml) Total | −LPS | Osmolarity (mOsm) |
|---|---|---|---|
| 1640 RPMI Medium | 0 | — | 299 |
| LPS (50 ng/10 µl) | 219 | 0 | 305 |
| Composition #B0213 | 1575 ± 470 | 1356 | 376 |
| Fractions (minutes): | | | |
| 2:05–21:20 | 656 ± 206 | 436 | 321 |
| 21:20–25:32 | 345 ± 82 | 126 | 309 |
| 25:32–31:55 | 287 ± 70 | 68 | 305 |
| 31:55–34:58 | 262 ± 50 | 43 | 304 |
| 34:58–46:55 | 237 ± 59 | 18 | 376 |

1. Total TNF Released is corrected for release by RPMI Medium.
2. Fraction Reconstitution: 2:05–21:20 in water, 21:20 to 48:55 in PBS.
3. Volume of composition and fractions: 200 µl.
4. Number of patients tested for TNF release: 5.
5. Osmolarities are averages for 2 of 5 patients; standard errors very small, therefore, not reported.

Whereas Table 22 shows the results of using 200 µl volumes, Table 23 shows the results of testing an additional three patients with 100 µl of the compositions and 100 µl of its RP-HPLC fractions in the absence of Polymyxin. Although the release by the composition is lower than with 200 µl of the composition (Table 22), the results are similar. Fraction 1 contains most of the activity with some activity in the later fractions 2 and 3.

TABLE 23

Separation and Testing of HPLC Fractions of
Composition in the Absence of Polymyxin.

| Sample Tested | TNF Released (pg/ml) Total | −LPS | Osmolarity (mOsm) |
|---|---|---|---|
| 1640 RPMI Medium | 0 | — | 303 |
| LPS (50 ng/10 µl) | 195 ± 72 | 0 | 302 |
| Composition #B0213 | 692 ± 266 | 497 | 347 |
| Fractions (minutes): | | | |
| 2:05–21:20 | 575 ± 82 | 379 | 310 |
| 21:20–25:32 | 226 ± 65 | 31 | 337 |
| 25:32–31:55 | 210 ± 71 | 14 | 305 |
| 31:55–34:58 | 192 ± 40 | 0 | 313 |
| 34:58–46:55 | 182 ± 73 | 0 | 344 |

1. Total TNF Released is corrected for release by RPMI Medium.
2. Fraction Reconstitution: 2:05–21:20 in water, 21:20 to 48:55 in PBS.
3. Volume of composition and fractions: 200 µl.
4. Number of patients tested for TNF release: 3.
5. Osmolarities are averages of patients tested; standard errors very small, therefore, not reported.

C. Effect of Osmolarity of TNF Release by the Composition

The composition of the invention is hyperosmolar. The effect of the hyperosmolarity of the composition on TNF-α releasing activity was studied. It was found that the composition, when adjusted for osmolality even to the point of being hypoosmolar, continued to release TNF-α.

D. Physicochemical Separation of the Composition by Precipitation with High Content of Organic Solvent Since most of the TNF-releasing activity of the composition did not bind to the RP-HPLC as evidenced by its quick elution, it was decided to use a column that acts on the inverse principle of reversed-phase chromatography separation where the sample is in a high content of organic solvent and permits hydrophilic interaction. This separation technique is used for small polar substances. However, when the composition was brought to 80% acetonitrile a precipitate formed. Thus, some of the contents of the composition in a high organic solvent buffer precipitated. The precipitate and the soluble fraction were separated. Both the precipitate and soluble fraction were taken to dryness by lyophilization. The precipitate and soluble fraction were reconstituted in aqueous solutions and both analyzed by RP-HPLC and tested for TNF-α releasing activity. Table 24 shows that most of the TNF-α releasing activity was contained in the precipitated material.

TABLE 24

TNF-Releasing Activity of Fractions of Composition
Prepared by Precipitation in 80% Acetonitrile.

| Sample Tested | Volume/ Concentration | TNF Released (pg/ml) Total | −LPS | Osmolarity (mOsm) |
|---|---|---|---|---|
| 1X 199 Medium | | 0 | — | 306 |
| LPS | 50 ng/10 µl | 161 ± 50 | 0 | 301 |
| Composition #B0213 | 100 µl | 471 ± 304 | 310 | 307 |
| | 200 µl | 505 ± 210 | 344 | 318 |
| Supernatant | 100 µl | 192 ± 63 | 31 | 309 |
| | 200 µl | 221 ± 69 | 60 | 310 |
| Precipitate | 100 µl | 626 ± 212 | 465 | 307 |
| | 200 µl | 1299 ± 565 | 1138 | 346 |

Note:
1. Total TNF Released is corrected for 1X 199 Medium.
2. Reconstitution: supernatant in PBS, precipitate in double distilled water.
3. Precipitate is in (hypotonic) 70% 1X 199 Medium.
4. Number of patients tested: 5.
5. Osmolarities are averages of 4 of 5 patients tested; standard errors very small, therefore, not reported.

Figure 11:
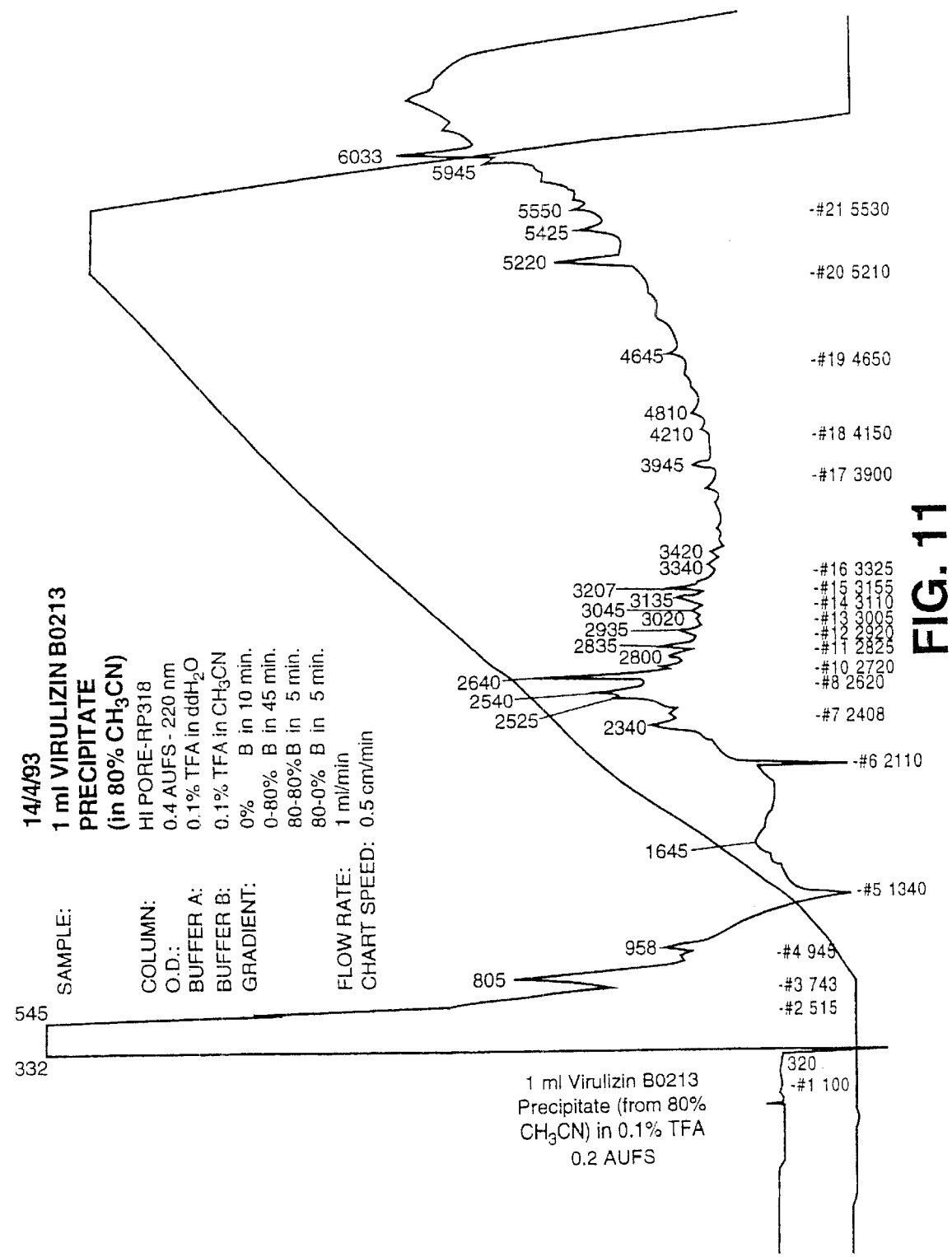
FIG. 11 shows the RP-HPLC analysis of precipitated fractions of the composition of the invention.
Figure 12:
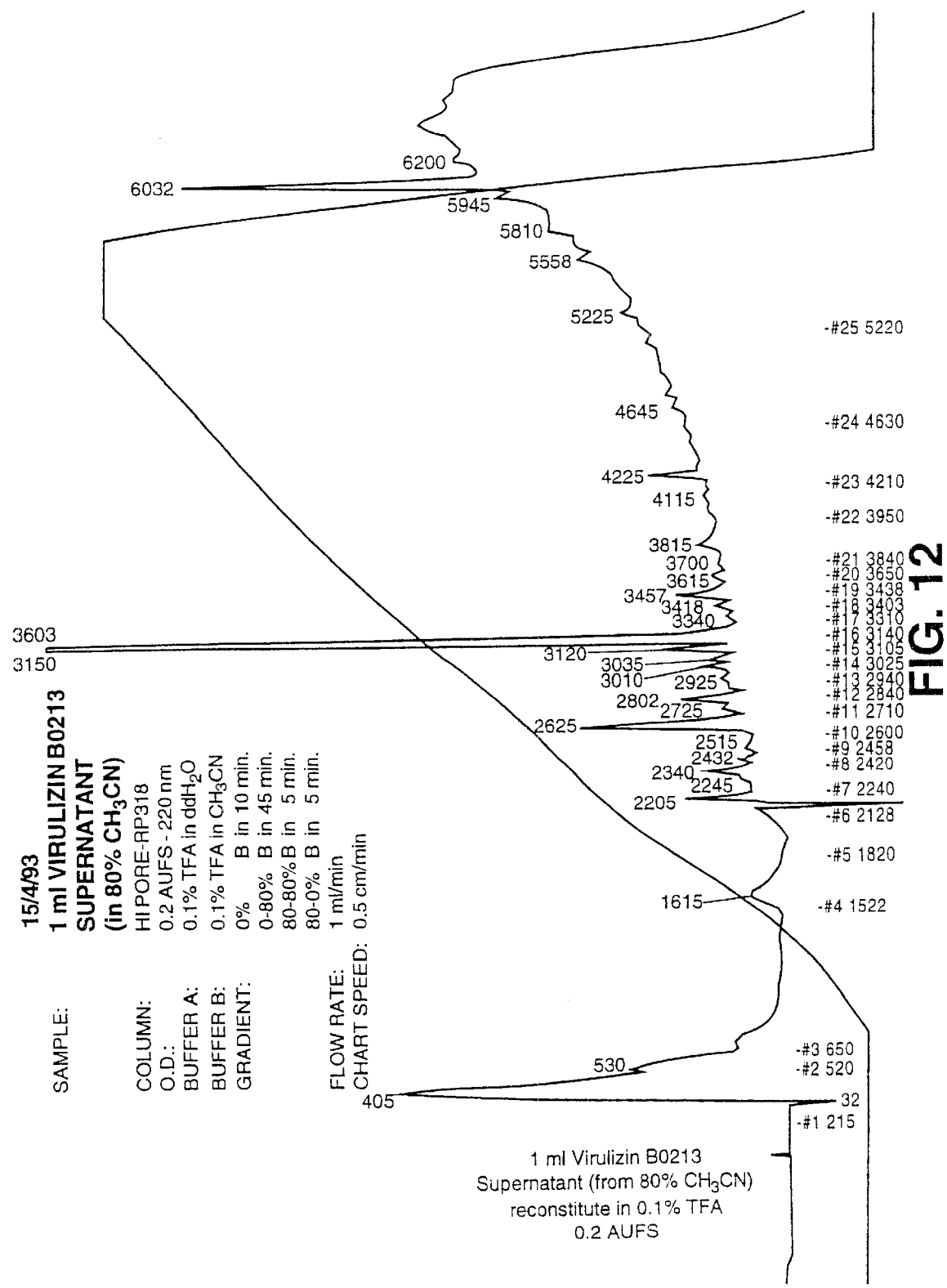
FIG. 12 shows the RP-HPLC analysis of soluble fractions of the composition of the invention.

RP-HPLC analysis of both the precipitated (FIG. 11) and soluble fractions (FIG. 12) of the composition shows that the precipitate is principally the material contained in fraction 1 of the RP-HPLC of the composition (FIG. 10), and the soluble material contains the other fractions of the RP-HPLC of the composition (FIG. 10). Thus in two different ways, it was shown that the composition's activity is contained in the fraction that is minimally retained by RP-HPLC. In fact, the precipitate had equal activity to unprecipitated composition when tested at 100 and 200 µl.

Only the 200 µl precipitate had about normal osmolarity. Consequently, the precipitate and soluble fractions (supernatant) of the composition were separated by RP-HPLC (FIGS. 11 and 12) and divided into two fractions (see profiles of RP-HPLC). Fraction 1 (2:00–21:10 min) was equivalent to the same fraction 1 of the composition separated by RP-HPLC and fraction 2 was equivalent to fractions 2 through 5 of the composition separated by RP-HPLC. The isolates were then tested for their TNF-α releasing activity. Table 26 shows that for two patients neither the precipitate or supernatant after RP-HPLC separation had any TNF-releasing activity. However, the results for the initial two patients (Table 25) suggested the possibility that the precipitate may not have been tested at the ideal volume. Consequently, the fractions were retested on two additional patients and at one lower concentration. Table 26 shows that at 50 and 100 µl, fraction 1 of the precipitate had the most activity. At 50 µl it released twice as much TNF-α as did 50 ng LPS. However, minor releasing activity was also found in RP-HPLC fraction 2 of the precipitate as well as minor activity was found on fractions 1 and 2 of RP-HPLC of the supernatant.

TABLE 25

TNF-Releasing Activity of HPLC Separated Fractions of 80% Acetonitrile Precipitated Composition.

| Sample Tested | 199 Medium Used | Volume/Conc. | TNF Released (pg/ml) Total | -LPS | Osmolarity (mOsm) |
|---|---|---|---|---|---|
| Medium | 1X | | 0 | — | 294 |
| LPS | 1X | 50 ng/10 µl | 194 ± 93 | 0 | 294 |
| (#B0213) | 1X–70% 1X | 100 µl | 855 ± 88 | 661 | 281 |
| | | 200 µl | 926 ± 163 | 732 | 291 |
| Supernatant | | | | | |
| 2:15–21:28 | 1X | 100 µl | 92 ± 75 | 0 | 269 |
| | 1X | 200 µl | 25 ± 25 | 0 | 242 |
| 21:43–46:13 | 70% 1X | 100 µl | 61 ± 56 | 0 | 296 |
| | 70% 1X | 200 µl | 2 ± 2 | 0 | 297 |
| Precipitate: | | | | | |
| 2:00–21:10 | 1X | 100 µl | 183 ± 15 | 0 | 305 |
| | 1X | 200 µl | 0 | 0 | 354 |
| 21:10–46:20 | 70% 1X | 100 µl | 62 ± 61 | 0 | 299 |
| | 70% 1X | 200 µl | 0 | 0 | 302 |

Note:
1. Total TNF released is corrected for TNF release by 199 Medium 1X.
2. Reconstitution: first fractions in double distilled water, second fractions in PBS.
3. Number of patients tested: 2.
4. Osmolarities are averages of patients tested: standard errors vary small, therefore not reported.
5. Averages of values in 1X and 70% 1X 199 Medium.

TABLE 26

TNF Release with further Titraton of Precipitate and Supernatant from 80% Acetonitrile Fractioned

| Sample Tested | Volume/Conc. | TNF Released (pg/ml) Total | -LPS | Osmolarity (mOsm) |
|---|---|---|---|---|
| 1X 199 Medium | | 0 | — | 317 |
| LPS | 50 ng/10 µl | 136 ± 38 | 0 | 320 |
| #B0213 | 100 µl | 274 ± 80 | 138 | 317 |
| Supernatant | | | | |
| 2:15–21:28 | 50 µl | 171 ± 66 | 35 | 319 |
| | 100 µl | 193 ± 73 | 57 | 322 |
| 21:48–46:13 | 50 µl | 184 ± 34 | 48 | 311 |
| | 100 µl | 162 ± 40 | 26 | 310 |
| Precipitate | | | | |
| 2:00–21:10 | 50 µl | 287 ± 69 | 150 | 333 |
| | 100 µl | 204 ± 40 | 68 | 355 |
| 21:10–46:20 | 50 µl | 148 ± 46 | 11 | 323 |
| | 100 µl | 198 ± 44 | 62 | 325 |
| | 200 µl | 1299 ± 565 | 1138 | 346 |

Note:
1. Total TNF released is corrected for TNF release by 199 Medium 1X.
2. Reconstitution: first fraction in double distilled water, second fractions in PBS.
3. Number of patients tested: 2.
4. Osmolarities are averages of patients tested: standard errors very small, therefore, not reported.
5. All samples in 1X 199 Medium.

E. TNF-α Releasing by Different Medis

It was observed that the seitch from RPMI 1640 to Medium 199 resulted in a lower TNF-α release was evaluated in Medium 199 and RPMI 1640 (Table 27). The results show that LPD from 10 to 200 ng is much more effective in releasing TNF-α in RPMI 1640 Medium than in Medium 199. Presumably the composition also gives greater release in RPMI 1640 Medium. Thus, cultural conditions can influence the degree of TNF-α release.

TABLE 27

Evaluation of TNF Release in Different Media

| | 1X 199 Medium | | 1640 RPMI Medium | |
|---|---|---|---|---|
| Sample Tested | TNF Released (pg/ml) | Osmolarity (mOsm) | TNF Released (pg/ml) | Osmolarity (mOsm) |
| Medium | 23 | 296 | 47 | |
| LPS: | | | | |
| 10 ng/10 µl | 124 | 291 | — | |
| 50 ng/10 µl | 155 | 292 | 356 | 285 |
| 100 ng/ml µl | 147 | 293 | 323 | 289 |
| 200 ng/10 µl | 213 | 294 | 455 | 288 |
| 1000 ng/10 µl | 404 | 298 | 558 | 292 |

Note:
1. Number of patients tested: 1.

F. Osmolarity of the Composition

Table 28 shows the osmolarities of different batches of the composition. BO213 is moderately high at 675 mOsm. BO222 shown to have TNF-releasing activity even better than BO213 is less hyperosmolar, 581 mOsm. The fractions BO226, BC11-06 and BC11-09 range from 540 to 603 mOSm.

TABLE 28

OSMOLARITIES OF WHOLE BATCHES

| Batch # | pH | Osmolarity (mOsm) |
|---|---|---|
| Concentrated: | | |
| B0222 | pre-pH | 411 |
| B0222 | pH adjusted | 581 |
| B0216 | pH adjusted | 872 |
| B0219 | pH adjusted | 886 |
| Nonconcentrated: | | |
| B0221 | pre-pH | 652 |
| B0221 | pH adjusted | 533 |
| B0213 | pH adjusted | 675 |
| B0225 | pH adjusted | 590 |
| B0226 | pH adjusted | 540 |
| BC 11-06 | pH adjusted | 445 |
| BC 11-09 | pH adjusted | 603 |

EXAMPLE 11

A. Tumor Necrosis Factor (TNF) Releasing Activity of a Composition of the Invention 1. Acetonitrile Precipitate and Supernatant of the Composition As, shown in the prior Example, 80% acetonitrile precipitated material and the unprecipitated (hence forth called Supernatant) composition were tested further to determine where the TNF-releasing activity resided.

Table 29 shows that the TNF-releasing component of the composition is precipitated by 80% acetonitrile, an organic solvent. Whereas the whole composition at 0.04 ml released about 15 pg/ml of TNF, 0.05 ml of precipitated Batches of the composition released 58 (BO222), O (BO221), and 17 (BO213) pg/ml, suggesting recovery of the TNF-releasing component by 80% acetonitrile precipitation. The precipitated composition was reconstituted in the same volume of liquid from which it had been precipitated. Thus, 0.1 ml of precipitate comes from 0.1 ml of whole composition and equals 0.1 ml whole composition.

TABLE 29

TNF Releasing Activity of Precipitates of Virulizin* Prepared in 80% Acetonitrile.

| Sample Tested | 199 Medium Used | Quantity in Wells | TNF Released (pg/ml) Total | -LPS | Osmo- larity (mOsm) |
|---|---|---|---|---|---|
| LPS | 1X | 50 ng | 322 ± 115 | 0 | 308 |
| Virulizin: B0222 | | | | | |
| Whole | 80% 1X | 40 µl | 337 ± 107 | 15 | 312 |
| Precipitate | 70% 1X | 200 µl | 1091 ± 137 | 769 | 351 |
| | 70% 1X | 100 µl | 620 ± 186 | 298 | 317 |
| | 70% 1X | 50 µl | 380 ± 132 | 58 | 297 |
| | 70% 1X | 25 µl | 312 ± 137 | 0 | 294 |
| Virulizin: B0221 | | | | | |
| Whole | 90% 1X | 40 µl | 282 ± 75 | 0 | 306 |
| Precipitate | 70% 1X | 200 µl | 981 ± 205 | 660 | 348 |
| | 70% 1X | 100 µl | 526 ± 169 | 205 | 314 |
| | 70% 1X | 50 µl | 308 ± 104 | 0 | 298 |
| | 70% 1X | 25 µl | 318 ± 185 | 0 | 292 |
| Virulizin: B0213 | | | | | |
| Whole | 90% 1X | 40 µl | 383 ± 72 | 61 | 312 |
| Precipitate | 70% 1X | 200 µl | 1143 ± 172 | 821 | 366 |
| | 70% 1X | 100 µl | 687 ± 186 | 365 | 326 |
| | 70% 1X | 50 µl | 339 ± 133 | 17 | 305 |
| | 70% 1X | 25 µl | 300 ± 144 | 0 | 298 |

Note:
1. Number of patients tested: 5.
2. Total TNF released in corrected for TNF release by 1X 199 Medium.
3. Osmolarities not corrected for 1X 199 Medium (311 mOsm).
4. Average of osmolarities given; standard errors not reported as values are very low.
5. Precipitate reconstituted in double distilled water.
6. LPS volume added to wells was 10 µl.
7. Wells contained a total volume of 1000 µl.
8. Sample volumes are equivalent.
*Composition of the invention is also referred to herein as VIRULIZIN It is of interest to note that in earlier studies generally between 0.1 and 0.2 ml of the composition was used to stimulate TNF-release. The precipitates of BO222, BO221 and BO213, reconstituted to 0.1 and 0.2 ml released between 205 and 821 pg/ml of TNF. At 0.1 ml of precipitate, batches BO222, BO221 and BO213 released between 205 and 365 pg/ml of TNF, a very similar quantity of TNF, indicating the consistency of the TNF-releasing activity of the three different batches.

On a separate group of donor leukocytes, the supernatants remaining after 80% acetonitrile precipitation of the composition were tested. Whereas 0.04 ml of whole batches of the composition (BO222 and BO213) released 175 and 233 pg/ml of TNF, 0.05 ml of the supernatant released 42 and 41 pg/ml about 33% of the activity of the whole composition. Blanks prepared in the same fashion with 80% acetonitrile had no TNF-releasing activity. Thus, TNF-releasing activity in the precipitate was not the result of some residual substance in the buffers used to induce the precipitate.

Whereas in the aforedescribed studies the precipitate and supernatant fractions were tested on leukocytes from different donors, another study was conducted in which the two fractions were tested on leukocytes from the same donors. For the two tested batches, the whole composition at 0.04 ml released between 0 and 41 pg/ml of TNF. In comparison, the precipitate of the same batches of composition at 0.05 ml released 141 and 749 pg/ml of TNF, whereas 0.05 ml of the supernatant fraction released between 6 and 57 pg/ml of TNF. Thus the precipitate contained much of the TNF releasing activity. The supernatant fraction still had some TNF-releasing activity but much less than the precipitate and no more than the whole composition.

2. Reversed Phase-HPLC Separated Fractions of the Composition of the Invention

Figure 18:
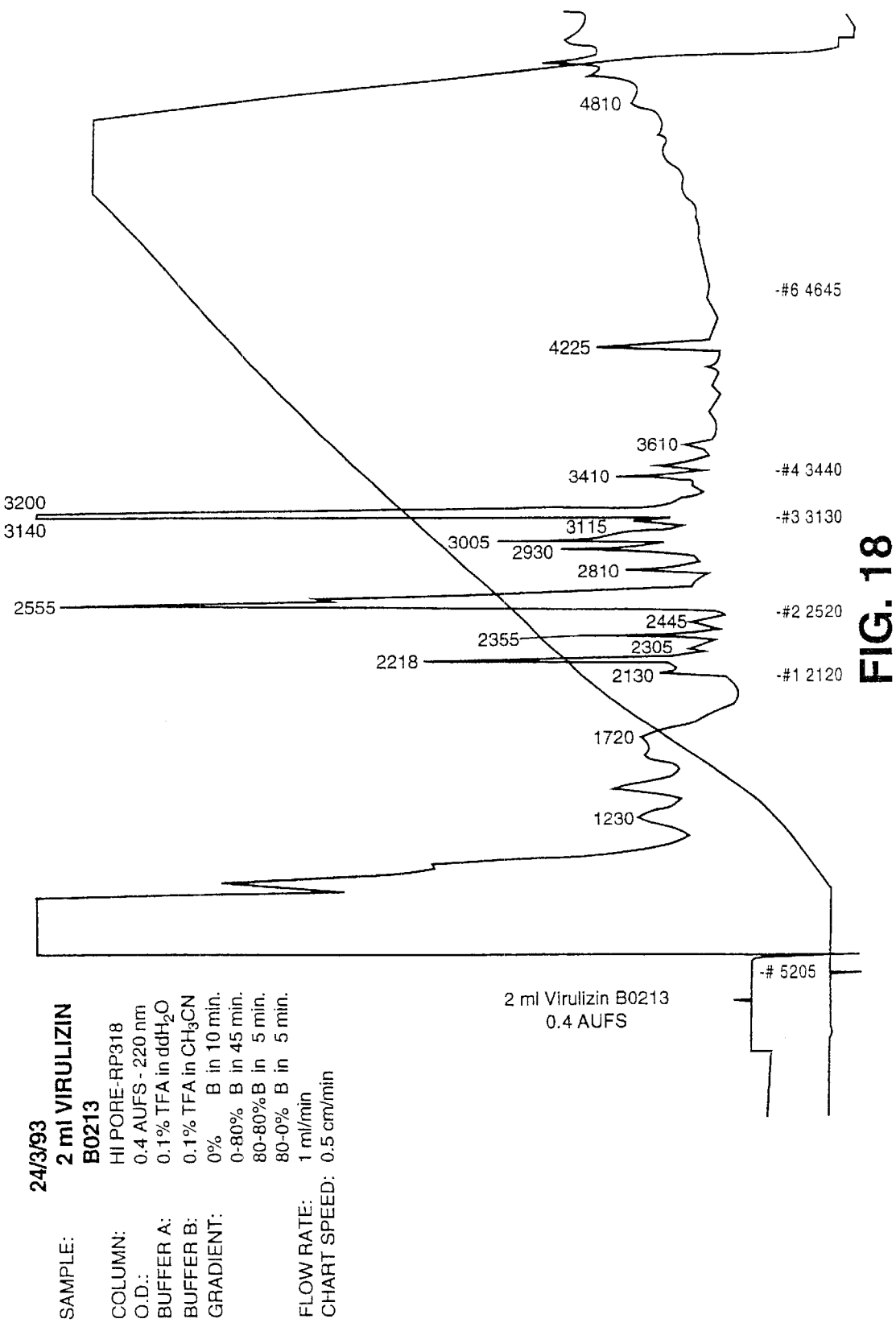
FIG. 18 is a graph showing the RP-HPLC profile of whole composition of the invention.
Figure 19:
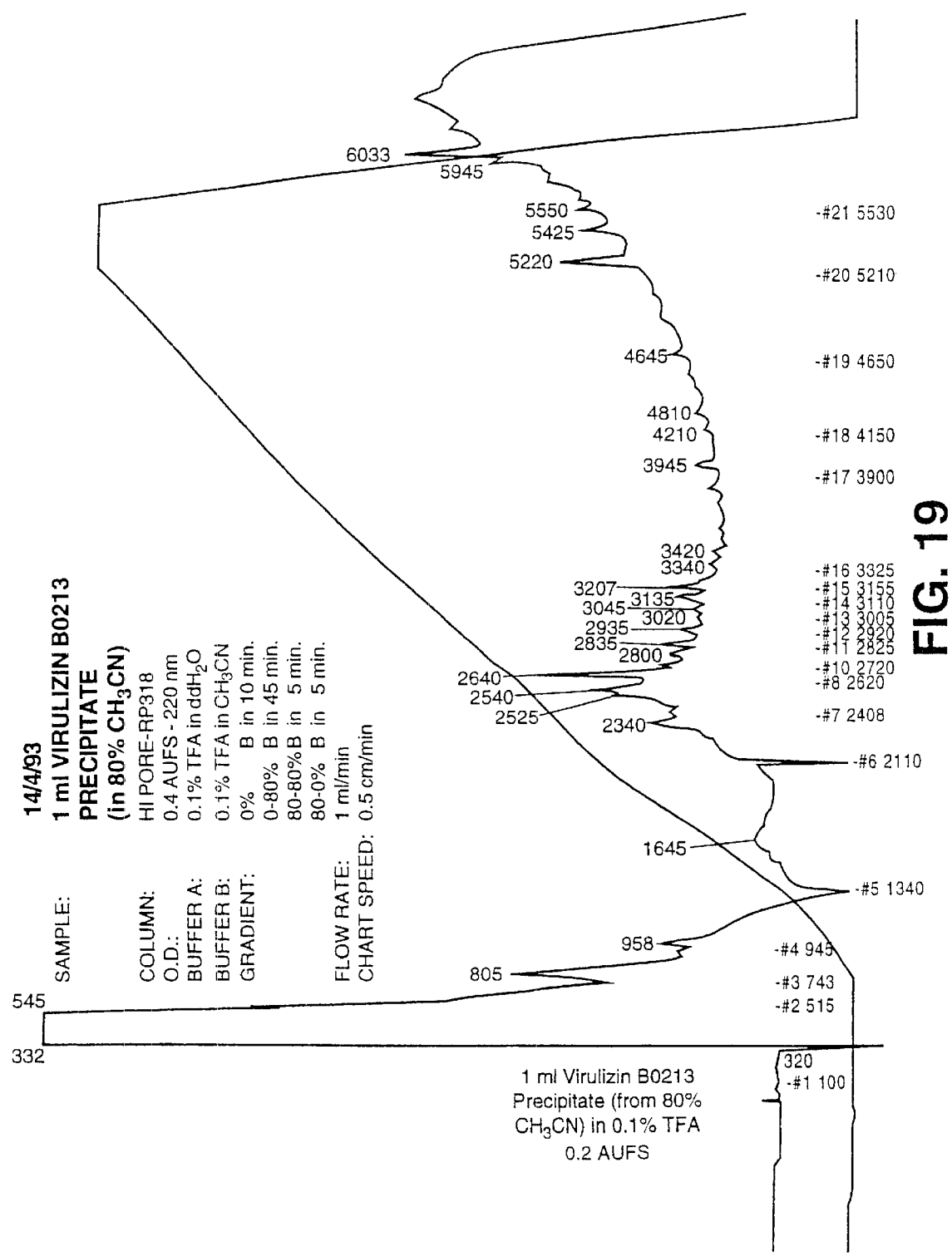
FIG. 19 is a graph showing the RP-HPLC profile of a precipitate of the composition of the invention.

As the precipitate of the composition was shown to contain much of the TNF-releasing activity, the profile of the precipitate was examined by $C_{18}$RP-HPLC. FIGS. 18, 19 and 20 show the RP-HPLC profiles of whole composition, the precipitate and the supernatant, respectively. The precipitate's profile shows principally the early eluting peak of whole composition (FIG. 19), whereas the supernatant's profile (FIG. 20) is similar to the whole composition except that the early peak is less intense.

In the next series of experiments, the activity of the precipitate and supernatants were evaluated after their separation by $C_{18}$ RP-HPLC. The precipitate and supernatant were collected as 2 pools from RP-HPLC: 2 to 21 min and 21 to 46 min. Earlier studies of fractions of whole composition separated by RP-HPLC indicated that TNF-releasing activity eluted principally in the 2 to 20 min fraction. Table 30 shows the results of testing whole composition and RP-HPLC fractions of the precipitate and supernatant. In this particular experiment, only 10 µl of the whole composition was used and caused no TNF-release. The precipitate pool from 2 to 21 min released TNF, whereas the 21 to 46 min pool did not (Table 30). The supernatant pool from 2 to 21 min also released TNF activity, whereas the 21 to 46 min pool released minimal quantities of TNF (Table 30). Thus for both the precipitate and supernatant, the TNF-releasing activity resides principally in the early eluting fraction from $C_{18}$ RP-HPLC.

TABLE 30

TNF Releasing Activity of HPLC Fractions of Precipitate and Supernatants of Virulizin Prepared in 80% Acetonitrile (2x wash)

| Sample Tested | 199 Medium Used | Quantity in Well | TNF Released (pg/ml) Total | -LPS | Osmo- larity (mOsm) |
|---|---|---|---|---|---|
| LPS | 1X | 50 ng | 99 ± 43 | 0 | 307 |
| Virulizin: B0222 | | | | | |
| Whole | 80% 1X | 10 µl | 83 ± 33 | 0 | 289 |
| HPLC Precipitate: | | | | | |
| 2:00–21:36 | 70% 1X | 100 µl | 153 ± 43 | 54 | 306 |
| | 70% 1X | 50 µl | 50 ± 14 | 0 | 289 |
| 21:36–46:28 | 1X | 100 µl | 97 ± 29 | 0 | 306 |
| | 1X | 50 µl | 103 ± 43 | 3 | 306 |
| HPLC Supernatant: | | | | | |
| 2:00–21:35 | 1X | 100 µl | 192 ± 55 | 92 | 330 |
| | 1X | 50 µl | 183 ± 72 | 83 | 320 |
| 21:35–46:30 | 1X | 100 µl | 65 ± 21 | 0 | 311 |
| | 1X | 50 µl | 142 ± 40 | 43 | 309 |
| Virulizin: B0213 | | | | | |
| Whole | 90% 1X | 10 µl | 93 ± 36 | 0 | 296 |
| HPLC Precipitate: | | | | | |
| 2:00–21:12 | 70% 1X | 100 µl | 165 ± 52 | 66 | 310 |
| | 70% 1X | 50 µl | 48 ± 15 | 0 | 287 |
| 21:12–46:12 | 1X | 100 µl | 88 ± 31 | 0 | 307 |
| | 1X | 50 µl | 101 ± 38 | 1 | 307 |
| HPLC Supernatant: | | | | | |
| 2:00–21:15 | 1X | 100 µl | 193 ± 76 | 93 | 317 |
| | 1X | 50 µl | 126 ± 43 | 26 | 306 |
| 21:15–46:20 | 1X | 100 µl | 59 ± 24 | 0 | 309 |
| | 1X | 50 µl | 126 ± 32 | 26 | 312 |

Note:
1. Number of patients tested: 5.
2. Total TNF released is corrected for TNF release by 1X 199 Medium.

TABLE 30-continued

TNF Releasing Activity of HPLC Fractions of Precipitate and
Supernatants of Virulizin Prepared in 80% Acetonitrile (2x wash)

| Sample Tested | 199 Medium Used | Quantity in Well | TNF Released (pg/ml) Total | -LPS | Osmo-larity (mOsm) |
|---|---|---|---|---|---|

3. Osmolarities not corrected for 1X 199 Medium (309 mOsm); standard errors are very low and, therefore, not reported.
4. Reconstitution: precipates in Type 1 water, supernatants in PBS buffer.
5. LPS volume added to wells was 10 μl.
6. Wells contained a total volume of 1000 μl.

The results suggest that the TNF-releasing substance in the precipitate and supernatant are likely closely related molecules, if not identical, with the only difference, if any, perhaps being the degree of solubility in 80% acetonitrile.

In another experiment the TNF-releasing activity of the two RP-HPLC pools of the precipitate were examined for three batches of the composition. Table 31 shows again that for three different batches (B0222, B0221, and B0213), the TNF-releasing activity is principally in the pool 2 to 21 min. Thus different batches are consistent.

TABLE 31

TNF Releasing Activity of HPLC Precipitate Fractions of
Virulizin Prepared in 80% Acetonitrile

| Sample Tested | 199 Medium Used | Quantity in Well | TNF Released (pg/ml) Total | -LPS | Osmo-larity (mOsm) |
|---|---|---|---|---|---|
| LPS (1) | 1X | 50 ng | 136 ± 62 | 0 | 299 |
| LPS (1) | 1X | 50 ng | 81 ± 25 | 0 | 306 |
| Virulizin: B0222 | | | | | |
| Whole | 1X | 40 μl | 734 ± 276 | 659 | 329 |
| | | 10 μl | 119 ± 11 | 38 | 303 |
| HPLC Precipitate: | | | | | |
| 2:00–21:25 min | 70% 1X | 200 μl | 20 ± 4 | 0 | 354 |
| | | 100 μl | 155 ± 32 | 74 | 307 |
| 21:23–46:20 | 1X | 200 μl | 67 ± 39 | 0 | 313 |
| | | 100 μl | 78 ± 10 | 0 | 310 |
| Virulizin: B0221 | | | | | |
| Whole | 90% 1X | 40 μl | 626 ± 90 | 490 | 315 |
| | | 10 μl | 62 ± 31 | 0 | 290 |
| HPLC Precipitate: | | | | | |
| 2:00–21:45 min | 70% 1X | 200 μl | 20 ± 7 | 0 | 365 |
| | | 100 μl | 170 ± 6 | 90 | 329 |
| 21:45–46:50 min | 1X | 200 μl | 45 ± 5 | 0 | 336 |
| | | 100 μl | 73 ± 15 | 0 | 311 |
| Virulizin: B0213 | | | | | |
| Whole | 90% 1X | 40 μl | 620 ± 123 | 484 | 315 |
| | | 10 μl | 80 ± 17 | 0 | 290 |
| HPLC Precipitate: | | | | | |
| 2.00–21.30 min | 70% 1X | 200 μl | 6 ± 4 | 0 | 393 |
| | | 100 μl | 153 ± 45 | 72 | 314 |
| 21:30–46:30 min | 1X | 200 μl | 182 ± 96 | 47 | 312 |
| | | 100 μl | 78 ± 20 | 0 | 310 |

Note:
1. For 100 & 10 μl samples; 3 patients tested for these samples.
2. For 200 & 40 μl samples; 4 patients tested for these samples.
3. Total TNF released is corrected for TNF release by 199 Medium 1X.
4. 199 Medium 1X @ 100 & 10 μl - 306 mOsm, @ 200 & 40 μl - 305 mOsm.
5. Osmolarities are averages and not corrected for 199 Medium 1X; standard errors are not reported as values are very low.

TABLE 31-continued

TNF Releasing Activity of HPLC Precipitate Fractions of
Virulizin Prepared in 80% Acetonitrile

| Sample Tested | 199 Medium Used | Quantity in Well | TNF Released (pg/ml) Total | -LPS | Osmo-larity (mOsm) |
|---|---|---|---|---|---|

6. LPS volume added to wells was 10 μl.
7. Wells contained a total volume of 1000 μl.
8. Sample volumes are equivalent.
9. Reconstitution: first fractions in double distilled water, second in PBS buffer.

In a further experiment, the effect of washing the precipitate with 80% acetonitrile was examined. The point of the experiment was to prove that the TNF releasing activity was not being simply trapped. Whole composition, 0.04 ml, released 325 pg/ml of TNF. The precipitate pool from 2 to 24 min at 0.1 ml released 324 pg/ml of TNF and at 0.05 ml, 3 pg/ml. The pool from 24 min to 46 min released no TNF. Likewise the supernatant pool from 2 to 24 min released TNF at 0.1 and 0.05 ml, whereas the pool from 24 to 46 min had some, but considerably less, TNF-releasing activity on RP-HPLC.

To be certain that the handling of RP-HPLC isolates of the composition were not responsible for the presence of TNF-releasing activity, samples were prepared in the same fashion but without the composition. RP-HPLC profiles of PBS and $H_2O$ blanks, their precipitates and supernatants were essentially free of any peaks.

Using mononuclear cells from identical donors, the samples were tested on leukocytes from the same donors. Whole composition and the precipitate eluting from 2 to 24 min released TNF, whereas PBS, $H_2O$ or their precipitates separated on RP-HPLC had no TNF releasing activity in the pool from 2 to 23 min. Thus, the precipitate eluting from 2 to 24 min causes specific TNF-release.

The precipitate pool of the composition eluting from 24 to 46 min released no TNF. The controls of water and PBS showed release of 114 and 40 pg/ml, respectively. Thus there was no specific release of TNF from the precipitate pool 24 to 46 min.

The supernatant fraction pool 2 to 24 min and 24 to 46 min released 82 and 68 pg/ml of TNF, respectively. The water and PBS blank pools from RP-HPLC released some TNF activity. The water pool 2 to 25 min and 25 to 46 min released 149 and 216 pg/ml of TNF respectively, and the PBS pools released O and 126 pg/ml respectively.

Thus, both the precipitated and supernatant fraction had TNF-releasing activity. RP-HPLC separation of the TNF-releasing activity showed that both eluted early from RP-HPLC, suggesting that the active components are physically very similar if not identical.

Table 32 provides a summary result of further testing, for 80% acetonitrile precipitates and supernatants after RP-HPLC separation, minus the activity in similarly prepared blank samples.

TABLE 32

Releasing activity of Virulizin less release by reconstitution solutions.

| Sample Tested | 199 Media Used | Quantity in Well | Actual Released (pg/ml) TNF-a | GM-CSF | IL-1β | Osmolarity (mOsm) |
|---|---|---|---|---|---|---|
| Virulizin: B0222 | | | | | | |
| Whole | 80% 1X | 40 μl | 178 | 136 | 142 | 310 |
| HPLC Precipitate (min): | | | | | | |
| 2:20–24:10 | 70% 1X | 100 μl | 75 | 13 | 18 | 314 |
| 24:10–46:20 | 70% 1X | 100 μl | 0 | 16 | 0 | 292 |
| HPLC Supernatant (min): | | | | | | |
| 2:00–23:55 | 1X | 100 μl | 82 | 86 | 0 | 336 |
| 23:55–46:20 | 1X | 100 μl | 0 | 45 | 29 | 316 |

Note:
1. Data derived from Virulizin Sumtable Table 24.4.
2. Virulizin reconstitution: 1st precipitate fraction in Type 1 water, all other fractions in PBS.
3. Whole amounts are unreconstituted and therefore not corrected.
4. Sample volumes are equivalent.

Whole composition releases TNF, GM-CSF and IL-1β in vitro from mononuclear cells at 24 hrs. The 80% acetonitrile precipitate contains the same releasing activity and most elutes in the early fraction from RP-HPLC. The supernatant fraction retains releasing activity and most elutes in the early fraction from RP-HPLC. The supernatant fraction retains releasing activity, but it also elutes in the early eluting RP-HPLC fraction for TNF and GM-CSF. The results suggest that likely the same component releases the three cytokines. For GM-CSF and IL-1β, the fact that some releasing activity elutes in the late fraction from RP-HPLC suggest that there may be another substance in the composition that can act on monocytes to release GM-CSF and IL-1β.

Physicochemical Analysis SDS Gel Electrophoresis

Having identified that TNF, IL-1β and GM-CSF releasing activity can be precipitated, in part, by 80% acetonitrile and that much of the releasing activity elutes early from $C_{18}$ RP-HPLC, the physicochemical properties of the precipitate fraction have been studied and compared to the whole composition and supernatant fraction of the composition.

SDS gell electrophoresis of whole composition and precipitates and supernatants of the composition was conducted. In all three instances, the composition runs near the SDS front, indicating a low molecular weight. The smallest standard used was 14,400 daltons.

Molecular Sieve HPLC

The molecular size of the composition was also examined by determining its time of elution from a molecular sieve HPLC column. The elution times of whole composition, precipitate and supernatant compared to standards. All three eluted later than insulin, which eluted at 24.5 min. Once again, physicochemical analysis indicates a mol. wt. less than 2,400 daltons.

Hydrophilic (Polyhydroxyethyl) HPLC

Figure 21B:
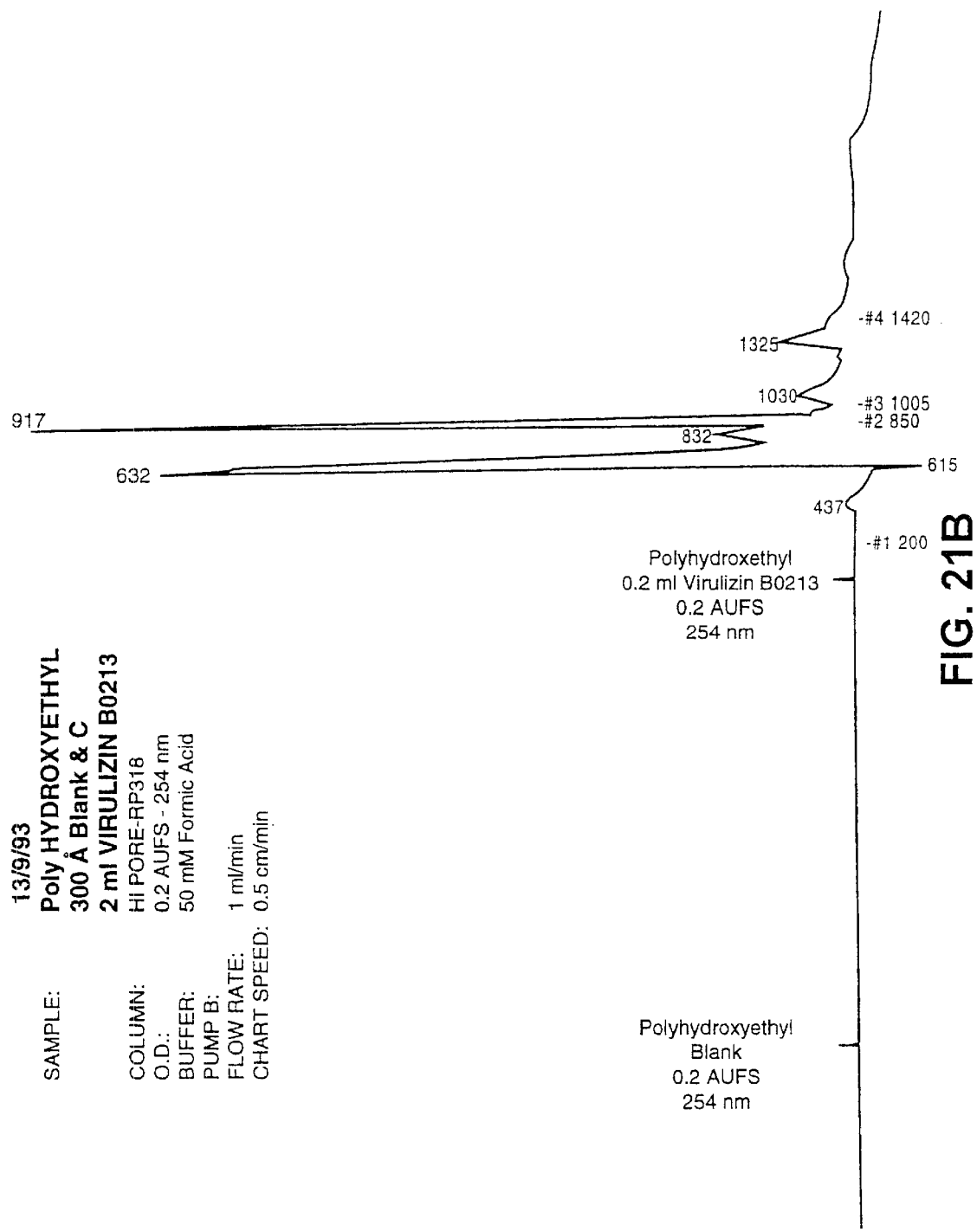
FIG. 21 shows the conditions and times of elution of the composition of the invention on hydrophilic HPLC (a) and the elution profile for a supernatant of the composition of the invention (b)
Figure 22:
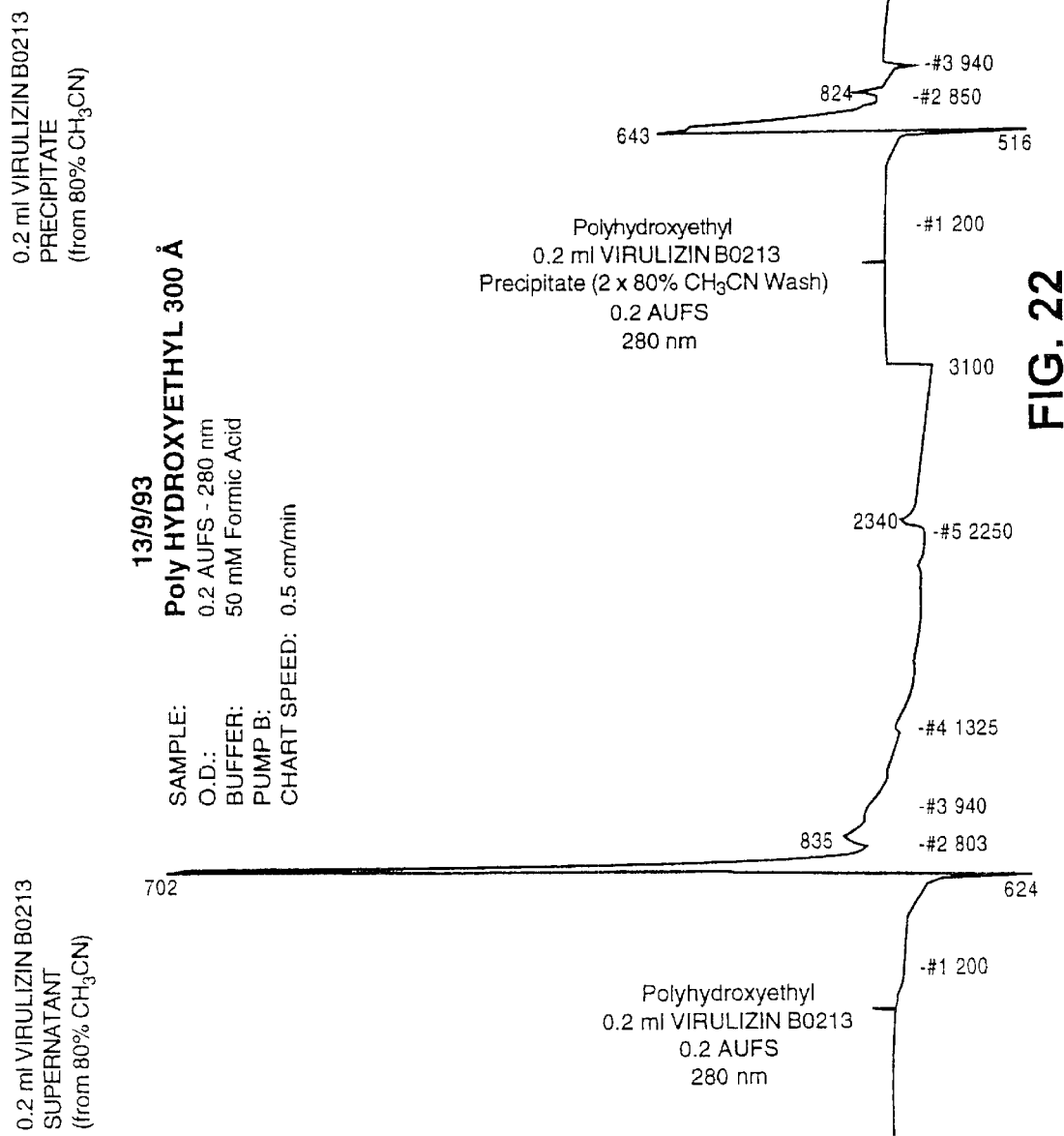
FIG. 22 shows the elution of a precipitate of the composition of the invention on hydrophilic HPLC.

The TNF-releasing component elutes early. Thus a column with the opposite effect was chosen, a hydrophilic column in the presence of organic solvents. The ideal eluting conditions for the polyhydroxyethyl column is 80% acetonitrile. However, as indicated in the prior Example, some of the substances in the preparation precipitated at this concentration. Consequently, the composition as analyzed at a low concentration of acetonitrile where the column functions mostly as a molecular sieve column. FIGS. 21 and 22 show the profile of whole supernatant and precipitate. The front sheet summarizes the elution time for the different peaks. The elution times indicate the active component of the composition has a low molecular weight.

Amino Acid Analysis and Sequencing of the Precipitated Component

Two samples were submitted for protein analysis by amino acid compositional analysis before and after acid hydrolysis: the acetonitrile precipitate and 2–20 min RP-HPLC eluted pool of the precipitate. The two samples were very similar by comparison of amino acid content before and post acid hydrolysis. There are, however, significant differences between the amino acid composition (post acid hydrolysis), and the free amino acid content which suggests that peptide bonds were hydrolyzed. The composition of the samples were peculiar in that they were very rich in glycine plus glutamate/glutamine.

From the foregoing, it may be speculated that at least one of the active components is proteineous. Analysis reveals potentially significant quantities of unidentified ninhydrin positive (most likely amino acid compounds, but other compounds may yield a response) components that appear to be stable to acid hydrolysis. The principal amino acids per 1000 residues in the sample are Asx (asparagine) 143, Thr (Threonine) 31, Glx (glutamate) 381, Gly (glycine) 187, and Ala (alanine) 170.

A comparison was made between free and released—(acid hydrolysis) amino acids. This shows the following amino acids per 1000 residues: Asx (asparagine) 51, Threonine 8.6, Serine 18, Glx (glutamine) 375, Pro (proline) 17, Glycine-(Glyj 429 and Alanine 86.

The ratio of Free/1000 is as follows:

| | Released/1000 |
|---|---|
| Asx | 4.09 |
| Thr | 2.03 |
| Ser | 1.65 |

-continued

| | Released/1000 |
|---|---|
| Glx | 1.18 |
| Gly | 0.37 |
| Ala | 1.69 |

There are 5 unidentified (ninhydrin positive) components. Highly speculative assignments are cysteic acid, glucosaminic acid and sarcosine. Also there may be methionine sulfoxide and methionine sulfone. The major unidentified ninhydrin component appears to be free components in the sample.

EXAMPLE 12

Release of IL-1β and IL-8

Table 33 shows that the composition of the invention stimulates human mononuclear cells in culture to release IL-1β and the 80% acetonitrile precipitate of the composition releases more than the remaining supernatant. Whereas the whole composition does not stimulate IL-8 release, fractionated composition seems to release some IL-8. The results shown in Table 33 are minus the release of IL-1β and IL-8 with mock samples.

TABLE 33

Releasing activity of Virulizin less release by reconstitution solutions.

| Sample Tested | 199 Media Used | Quantity in Well | Actual Released IL-1β (pg/ml) | IL-8 (ng/ml) | Osmolarity (mOsm) |
|---|---|---|---|---|---|
| Virulizin: B0222 | | | | | |
| Whole | 80% 1X | 40 μl | 171 | 0 | 304 |
| Precipitate | 70% 1X | 100 μl | 160 | 71 | 292 |
| Supernatant | 90% 1X | 100 μl | 17 | 87 | 335 |

Note:
1. Number of patients tested: 5.
2. Reconstitution: precipitate in Type 1 water, supernatant in PBS buffer.
3. Samples are corrected for release by 1X 199 Medium and LPS: 154, 1065 pg/ml, and 68, 294 ng/ml, respectively, for IL-16 and IL-8.
4. Osmolarities for media and LPS are: 311 and 309, respectively.
5. LPS volume added to wells: 10 μl.
6. Total volume of wells: 1000 μl.
7. Sample volumes are equivalent.

Physicochemical Characteristics

The composition and its precipitate and supernatant were separated by ion-exchange HPLC. Both by AX300 (anion exchange) chromatography and by CMX 300 (cation exchange) chromatography, there was no significant separation of components. Hydrophobic reverse phase chromatography did not separate the peaks.

Capillary Electrophoresis

The precipitate was analyzed by capillary electrophoresis. At high pH, a W absorbing peak was observed at 190 nm but completely disappeared at 200 nm. There were no significant peaks at 214 nm Uv absorption.

Free amino acid are not visualized unless they are derivatized. It is thought that the W peak at 190 nm is likely a salt.

EXAMPLE 13

The composition was evaluated for stimulatory activity in the following 3 indicator systems: 1) Stimulation of lymphocyte DNA synthesis; 2) Induction of lymphocyte-mediated cytotoxic function; and 3) Induction of monocyte/macrophage-mediated cytotoxic function. These tests were chosen for the screen because they measure immunological functions which have been shown to be associated with different clinical parameters in patients with malignant disease. These indicators of immune function also can be modulated in cancer patients who are treated with different biological response modifying agents such as interferon or interleukin-2. The results of the initial screening procedure are presented below.

1) Stimulation of Lymphocyte DNA synthesis: comparison with an optimal stimulating concentration of phytohemagglutinin (PHA)

| Stimulant | Counts per Minute |
|---|---|
| Medium | 374 |
| PHA | 125, 817 |
| Composition (#222) | 1,116 |
| Composition (1:10) | 1,021 |
| Composition (1:50) | 649 |

Results: Unlike the prototypic mitogen, PHA, the Composition does not stimulate lymphocytes to undergo blastogenesis and cell division.

2) Stimulation of Lymphocyte-mediated Cytotoxic Function: comparison with an optimal stimulating concentration of Interleukin-2 (IL-2)

| Stimulant | Lytic Units |
|---|---|
| Medium | 30.8 |
| IL-2 | 472.5 |
| Composition (neat) | 48.1 |
| Composition (1:10) | 33.3 |
| Composition (1:50) | 44.8 |

Results: Unlike the prototypic stimulator of lymphocyte cytotoxic function, Interleukin-2, the composition does not elicit lymphocyte cytotoxicity.

3) Stimulation of Monocyte-Mediated Cytotoxic Function by the Composition: Comparison with Gamma Interferon & Endotoxic (γ-IFN+LPS)

| Stimulant (E/T = 20/1) | % Cytotoxicity |
|---|---|
| Medium | 4.3 |
| IFN + LPS | 24.4 |
| Composition (neat) | 19.7 |
| Composition (1:10) | 20.0 |
| Composition (1:50) | 11.5 |

Results: The composition is capable of stimulating peripheral blood monocytes to express tumoricidal function in a dose dependent manner. The magnitude of stimulation is comparable to that elicited by the prototypic macrophage activator combination of γIFN+LPS. It is important to recognize that the action of the composition in these in vitro assays did not require the addition of endotoxin as in the case with any other macrophage activators. If the composition is free of endotoxin contamination, its biological activity in this assay of macrophage activation would be considered biologically significant.

Monocyte/Macrophage Studies with the Composition

Because the screen procedures demonstrated that the composition does not stimulate lymphocyte functions but can stimulate monocyte functions, subsequent studies were aimed at further characterization of the monocyte/macrophage stimulatory activities of this compound. A number of comparative studies aimed at determining the dose response characteristics of the composition in stimulating monocyte/macrophage tumoricidal function, were performed as well as testing different batches of the compound. The main emphasis of the studies was to test the capacity of the composition to stimulate tumoricidal function in monocytes and macrophages from different anatomical sites of cancer patients. The central hypothesis guiding these studies is that the therapeutic efficacy of any biological stimulator will depend, in large part, on its ability to elicit tumoricidal function in environments which contain malignant disease. That could come about by direct stimulation of resident immune cells in tumor microenvironments. Alternatively, this could come about by stimulation of circulating immune cells if those cells were then able to home on sites of malignant disease and to function in that environment. For these investigations, the following were relied upon: 1) peripheral blood monocytes from cancer patients and control subjects; 2) alveolar macrophages from lung cancer patients and control patients with non-malignant lung diseases; and 3) Peritoneal macrophages from patients with gynecological malignancies.

1. Dose Response and Different Batch Studies with the Composition

Figure 23:
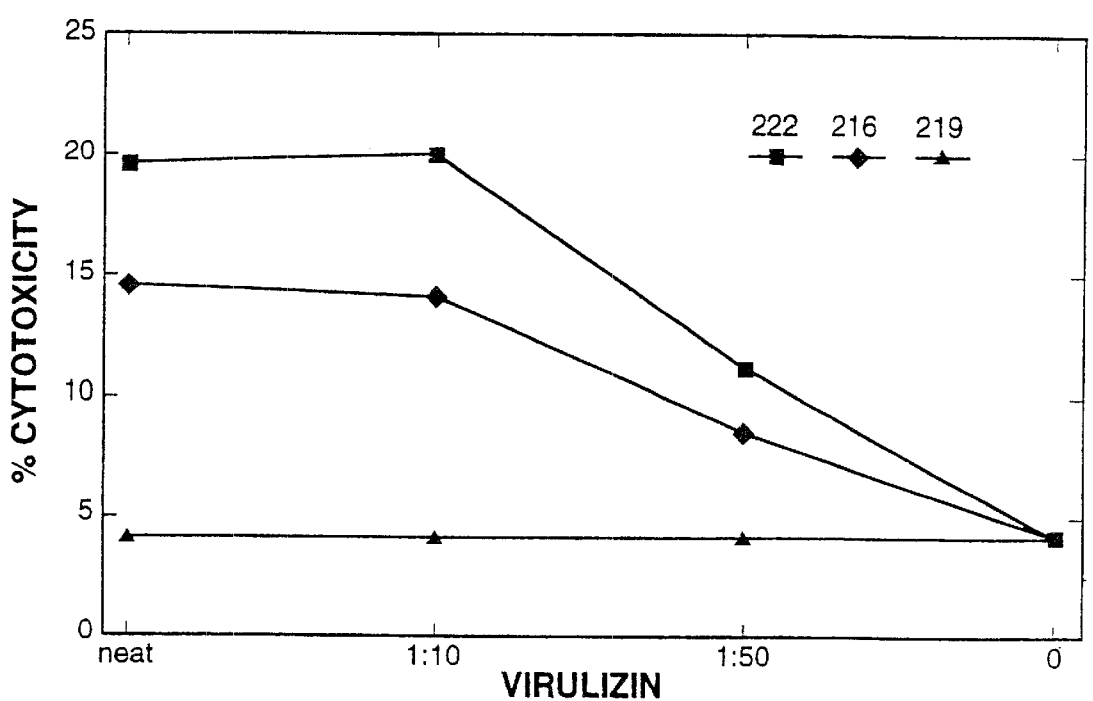
FIG. 23 is a graph showing dose response of the composition of the invention in stimulating peripheral blood monocyte function.

These studies relied on peripheral blood monocytes to test the stimulatory activities of different doses and different batches of the composition. Three batches of the composition were provided for testing. These were designated as batch #s 216, 219 and 222. Each batch of the composition was tested without dilution (neat), a 1:10 dilution and a 1:50 dilution of material. The results are depicted graphically in FIG. 23.

Results: Batch #222 and 216 stimulate monocyte tumoricidal function, Batch #219 did not. It appeared that #222 was superior to 216 in these preliminary investigations. Batch #222 appears to stimulate equivalent levels of tumoricidal function at the undiluted (neat) and 1:10 dilution concentration with less, but still detectable activity at the 1:50 dilution. Batch #216 gave the greatest stimulation of tumoricidal function at the undiluted (neat) concentration, with less activity at the 1:10 dilution and no detectable activity at the 1:50 dilution. As stated above, Batch #219 did not elicit detectable monocyte tumoricidal function at any concentration tested.

2. Tumoricidal Function in Peripheral Blood Monocytes

Tests have been performed on 4 peripheral blood monocyte samples from control subjects. These tests utilized an optimal stimulating concentration of the composition (1:10 dilution of batch #222) and an optimal stimulating concentration of γ-IFN+LPS. The target cells in these studies were a cultured, NK-insensitive cell line, the Chang Hepatoma

| Stimulant (E/T = 20/1) | % Cytotoxicity |
| --- | --- |
| Medium | 5.4 +/− 1 |
| γ-IFN + LPS | 15.6 +/− 4 |
| Composition | 22.3 +/− 6 |

A test was also performed on 1 monocyte sample from a patient with cervical cancer. This test was important because the patient's own tumor cells were available to be used as target cells in the assay. As before, this test utilized an optimal stimulating concentration of the composition (1:10 dilution of batch #222) and an optimal stimulating concentration of γ-IFN+LPS. Also, the effector/target cell ratio was reduced to 15/1 to conserve patient tumor cells.

| Stimulant (E/T = 20/1) | % Cytotoxicity |
| --- | --- |
| Medium | 5.5 |
| γ-IFN + LPS | 14.4 |
| Composition | 20.9 |

Results: In the peripheral blood monocyte from control subjects, the composition stimulated monocyte tumoricidal function against the Chang Hepatoma at a level equal to or greater than the level elicited by an optimal stimulating concentration of γ-IFN+LPS. In the peripheral blood monocytes from a patient with cervical cancer, the composition stimulated tumoricidal function against the patient's own tumor cells at a level which exceeded that elicited by γ-IFN+LPS by <30%.

3. Tumoricidal Function in Peritoneal Macrophages from Patient with Gynecological Malignancies These tests were performed on peritoneal macrophage samples isolated from lavage fluids of 1 patient with cervical cancer and 1 patient with Ovarian Cancer. These tests were performed with the patient's own tumor cells as target cells in the assay. As before, an optimal stimulating concentration of the composition (1:10 dilution of batch #222) and an optimal stimulating concentration of γ-IFN+LPS were compared. Also, the effector/target cell ratio was reduced to 15/1 to conserve patient tumor cells.

| Stimulant | Cervical Cancer | Ovarian Cancer |
| --- | --- | --- |
| Medium | 8.2 | 0.6 |
| IFN + LPS | 29.8 | 4.1 |
| Composition (1:10) | 13.2 | 8.9 |

Results: These test results highlighted the fact that the local tumor environment may be a determinant of the response of immune cells to immunological activators. In this case of cervical cancer, there was no pathological evidence of malignant disease within the peritoneal cavity and the development of tumoricidal function against the autologous tumor was better with γ-IFN+LPS than the composition. In the patient with ovarian cancer, there was significant tumor in the peritoneal cavity. The response against the patient's own tumor to γIFN+LPS was minimal at best, whereas the response to the composition was greater.

4. Tumoricidal Function in Alveolar Macrophages from Lung Cancer Patients and Control Subjects These tests were performed on alveolar macrophage samples isolated from broncholveolar lavage fluids of a patient with non-small cell lung cancer and 3 patients with non-malignant diseases of the lung. These tests utilized an optimal stimulating concentration of the composition (1:10 dilution of batch #222) and an optimal stimulating concentration of γ-IFN+LPS. The target cells in these studies were the Chang Hepatoma cells and the effector/target cell ratio was 20/1.

| Stimulant | Cancer Patients | Control |
|---|---|---|
| Medium | 2.6 +/− 2 | 19.5 +/− 4 |
| γ-IFN + LPS | 10.9 +/− 13 | 1.2 +/− 5 |
| Composition | 5.2 +/− 2 | 18.6 +/− 8 |

Results: Alveolar macrophages from lung cancer patients are impaired in their development of tumoricidal function in response to conventional macrophage activators such as γIFN+LPS. These results are consistent with this observation; they show that the tumoricidal function of alveolar macrophages from lung cancer patients is greatly reduced compared to control subjects. They also show that the composition does not activate tumoricidal function in either the alveolar macrophages of lung cancer patients or the alveolar macrophages of control subjects with non-malignant lung diseases.

These preliminary in vitro tests with the composition demonstrate that it is a macrophage activator. The material provided was able to elicit tumoricidal activity in a standard cytotoxicity assay against both an NK insensitive cell line and against freshly dissociated human tumor cells. The activity elicited was also found to be concentration dependent in these tests. The capacity of the composition to active macrophage tumoricidal function in vitro is comparable to that of the best macrophage activating combination presently available, namely, γIFN+endotoxin. As stated above, the capacity of the composition to elicit this level of tumoricidal function in the absence of endotoxin would be considered important biologically if the material is free of endotoxin contamination.

As has been found for other macrophage activators, the activity of the composition in stimulating macrophage tumoricidal function varies with the source of the macrophages. It appears that the composition is an excellent activator of peripheral blood monocytes being equivalent to γIFN+LPS with normal donors and possibly superior to γIFN+LPS with cancer patient donors. Malignant disease has a significant impact on the development of monocyte tumoricidal function depending on the activator used (Braun et al, 1991). One determinant of the biological activity of different macrophage activators in cancer patients monocytes is the sensitivity of the activator to arachidonic acid metabolism and the secretion, by the cell of prostaglandins. From these initial studies with the composition, it appears that activity elicited with the compound is not sensitive to the inhibitory effects of prostaglandins. If prostaglandin insensitivity can be proven definitively for cancer patient monocytes stimulated with the composition, this would be considered important therapeutically since the effectiveness of many other biological activators is limited by prostaglandins. Preliminary studies with 2 specimens indicate that the composition may have good activity in peritoneal macrophages, particularly when malignant disease is present in the peritoneal cavity.

These preliminary results also illustrate what has been found when comparing the capacity of different activators to stimulate tumoricidal function in peritoneal macrophages of patients with different gynecological malignancies. In those studies, it was found that the presence of malignant disease within the peritoneal cavity influences the responsiveness of the peritoneal macrophages to specific activators. In patients with cervical cancer, malignant disease is not present in the peritoneal cavity in general, and thus, the response of the resident macrophages to γIFN+LPS is normal. When disease is present in the cavity, however, as in the case with ovarian cancer, the response to y1FN+LPS is suppressed. This is related, in part, to changes in the arachidonic acid metabolism of the peritoneal macrophages when malignant disease is present (Braun et al, 1993). The fact that the composition apparently can activate tumoricidal function in peritoneal macrophages from ovarian cancer patients against the patient's own tumor cells may reflect, once again, a mechanism for activation which is independent of the arachidonic acid metabolic pathway.

On the other hand, the composition clearly does not activate alveolar macrophages to become tumoricidal whether malignant disease is present in the lung or not. Alveolar macrophages from lung cancer patients have been found to be inhibited significantly in their development of tumoricidal function when compared to either peripheral blood monocytes from the same patients or to control alveolar macrophages from patients with non-malignant lung diseases (Siziopikou et al., 1991). Thus, the lack of activity of the composition in this case is not surprising.

EXAMPLE 14

The development of tumoricidal function in response to the composition of the invention and other macrophage activators was investigated in peripheral blood monocytes and peritoneal macrophages from patients with gynecological disease. More particularly, the patient population consisted of 7 patients, 3 with benign disease and 4 with malignant disease (2 ovarian cancers, 1 endometrial cancer, and 1 cervical cancer). Samples were removed from patients at the time of surgical procedure. Preparations containing peripheral blood monocytes were isolated from blood samples using the procedure set out in Braun et al. Cancer Immunol. Immunother 32:55–61, 1990 and preparations containing peritoneal macrophages were isolated as set out in Braun et al., Cancer Research 53:3362, 1993. Tumor cell cytotoxicity in response to the composition of the invention (1:10 dilution of stock batch 222) and other activators namely gamma interferon (100 U/ml), interleukin-12 (55 U/ml), and monocyte-CSF (55 U/ml) was assessed using the monocyte cytotoxicity assay described in Braun, et al., Cancer Immunol. Immunother 32:55–61, 1990.

The results as shown in Table 34, demonstrate that the composition of the invention stimulates tumoricidal function in both the peripheral blood monocytes and the peritoneal macrophages from patients with malignant and non-malignant gynecological diseases. The tumor cytotoxicity elicited by the composition of the invention is equal to or greater than that elicited by the other biological stimulators which were tested.

TABLE 34

The Development of Tumoricidal Function in Response to the Composition of the invention and other Macrophage Activators in Peripheral Blood Monocytes and Peritoneal Macrophages from Patients with Gynecological Diseases (3 benign disease, 4 malignant disease)
% Tumor Cytotoxicity (+/− S.E.)
at Monocyte/Tumor Cell ratio - 15/1

| Activator | Peripheral Blood | Peritoneal Macrophage |
|---|---|---|
| Medium | 8.6 ± 3 | 3.1 ± 1 |
| Gamma Interferon | 18.3 ± 2 | 9.5 ± 1 |
| Interleukin-12 | 26.0 ± 4 | 8.5 ± 2 |

TABLE 34-continued

The Development of Tumoricidal Function in Response to the
Composition of the invention and other Macrophage Activators
in Peripheral Blood Monocytes and Peritoneal Macrophages
from Patients with Gynecological Diseases (3 benign disease,
4 malignant disease)
% Tumor Cytotoxicity (+/− S.E.)
at Monocyte/Tumor Cell ratio − 15/1

| Activator | Peripheral Blood | Peritoneal Macrophage |
| --- | --- | --- |
| Monocyte-CSF | 16.0 ± 2 | 7.0 ± 2 |
| Composition of the Invention (Virulizin) | 23.0 ± 6 | 12.5 ± 2 |

EXAMPLE 15

The effect of indomethacin, a prostaglandin synthesis inhibitor, on the development of tumoricidal function in response to the composition of the invention and other macrophage activators in peripheral blood monocytes from cancer patients was also investigated. Samples from the Patients with malignant disease in Example 14 were tested using the assay system as described in Example 14 with the exception that indomethacin (up to 5 ng/ml) was simultaneously added with the composition of the invention, interleukin-12 (500 U/ml), and monocyte-CSF (500 U/ml).

The results as shown in Table 35 indicate that indomethacin augments cytotoxicity in response to IFNa, GM-CSF and N-CSF. Thus, the development of tumoricidal function in response to IFN-y, GM-CSF, and M-CSF was regulated by an indomethacin-sensitive function. In contrast, the development of tumoricidal function in response to Phorbol Ester (PNA), IL-12 and the composition of the invention was not regulated by an indomethacinsensitive function i.e. indomethacin did not augment cytotoxicity in response to the composition of the invention, IL-12 and PNA.

TABLE 35

The Effect of Indomethacin, a Prostaglandin Synthesis Inhibitor,
on the Development of Tumoricidal Function in
Response to the Composition of the Invention and
other Macrophage Activators in Peripheral Blood Monocytes from
Cancer Patients.

| Activation Conditions | # donors | % cytotoxicity |
| --- | --- | --- |
| *IFN-γ | 23 | 11.9 ± 9 |
| *IFN-γ + Indomethacin |  | 25.2 ± 17 |
| *GM-CSF | 10 | 7.8 ± 6 |
| *GM-CSF + Indomethacin |  | 17.8 ± 8 |
| *PMA | 6 | 27.3 ± 14 |
| *PMA + Indomethacin |  | 22.0 ± 17 |
| IL-12 | 3 | 24.7 ± 5 |
| IL-12 + Indomethacin |  | 25.6 ± 6 |
| M-CSF | 3 | 14.1 ± 3 |
| M-CSF + Indomethacin |  | 19.0 ± 3 |
| Composition (Virulizin) | 4 | 18.7 ± 6 |
| Composition (Virulizin) + Indomethacin |  | 16.4 ± 6 |

EXAMPLE 16

The effect of prostaglandin $E_2$ on the development of tumoricidal function in response to the composition of the invention in the presence of indomethacin was investigated. The subject population consisted of one normal and eight patients (one patient with a pancreatic tumor, two patients with head and neck tumors, one with endometriosis, and four with HIV). Preparations containing peripheral blood monocytes were isolated from blood samples from the patients using the procedure set out in Braun et al. Cancer Immunol. Immunother 32:55–61, 1990. Tumor cell cytotoxicity in response to the composition of the invention (1:10 dilution of stock batch 222) and indomethacin (up to 5-g/ml), with or without $PGE_2$ ($10^8$ M), was assessed using the monocyte cytotoxicity assay described in Braun et al., Cancer Immunol. Immunother 32:55–61, 1990.

The results in Table 36 show that 36 pathophysiological levels of $PGE_2$ ($10^8$ M) failed to suppress the level of tumoricidal function which developed in response to the composition of the invention. This is in contrast to the capacity of $PGE_2$ to suppress tumoricidal function in monocytes stimulated with γ-interferon (Braun et al, Cancer Research 53:3362, 1993).

TABLE 36

The Effect of Prostaglandin $E_2$ on the Development of Tumoricidal
Function In Response to the Composition of the
Invention in the Presence of Indomethacin.
% Tumor Cytotoxicity at Menocyte/Tunor Cell ration = 15/1

| Diagnosis | Composition (Virulizin) | Composition (Virulizin) + Indomethacin | Composition (Virulizin) + Indomethacin + $PGE_2$ |
| --- | --- | --- | --- |
| Normal | 19 | 20 | 27 |
| Pancreatic | 15 | 14 | 22 |
| HNSCC | 9 | 8 | 12 |
| HNSCC | 11 | 3 | 12 |
| Endometriosis | 37 | 37 | n.d. |
| HIV | 6 | 7 | 8 |
| HIV | 15 | 12 | 19 |
| HIV | 21 | 16 | 20 |
| HIV | 23 | 22 | n.d. |

EXAMPLE 17

The development of tumoricidal function against autologous tumor cells in monocytes stimulated with the composition of the invention was investigated. Preparations containing peripheral blood monocytes were isolated from blood samples from 6 patients (three ovarian cancers, one endometrial cancer, one cervical cancer and one ENT cancer) using the procedure set out in Braun et al., 1900. Tumor cell cytotoxicity in response to the composition of the invention (1:10 dilution of stock batch 222) and indomethacin (up to 5-g/ml), with or without $PGE(10^8 N)$ was assessed using the monocyte cytotoxicity assay described in Braun et al., 1990, with the exception that the patient's tumor cells were used in place of the Chang hepatoma cells. The patient's tumor cells were treated with collagenase and DNase, single cell preparations were prepared, and the cells were labelled as described in Braun et al., 1990.

The result shown in Table 37 demonstrate that the composition of the invention is capable of activating the patient's own monocytes to kill the patient's tumor. The composition of the invention is at least as effective as the standard biological activators which are currently being used.

TABLE 37

The Development of Tumoridical Function against Autologous Tumor Cells in Monocytes Stimulated with the Composition of the Invention (Virulizin)

| Diagnosis | Culture Conditions | % Tumor Cytotoxicity (E/T - 15/1) |
|---|---|---|
| Ovarian Cancer | Medium | 2 |
|  | Composition (Virulizin) | 11 |
| Ovarian Caucer | Medium | 1 |
|  | γ-Interferon + LPS | 4 |
|  | Composition (Virulizin) | 9 |
| Ovarian Cancer | Medium | 0 |
|  | γ-Interferon + LPS | 14 |
|  | Composition (Virulizin) | 11 |
| Endometrial Cancer | Medium | 6 |
|  | γ-Interferon + LPS | 14 |
|  | Composition (Virulizin) | 21 |
| Cervicial Cancer | Medium | 8 |
|  | γ-Interferon + LPS | 30 |
|  | Composition (Virulizin) | 13 |
| ENT Cancer | Medium | 11 |
|  | γ-Interferon + LPS | 12 |
|  | Composition (Virulizin) | 25 |

The experimental results in Examples 14 to 17 indicate that the composition of the invention is capable of activating monocytes to express tumoricidal function, and it is at least as effective as other activators currently being used in the clinical setting; it works in the blood with peritoneal macrophages; and it appears to not be subject to the inhibitory effects of prostaglandins, which is one of the principle forms of immunosuppression in patients. The experimental data also supports the utility of the composition in the treatment of peritoneal and gynecological malignancies.

EXAMPLE 18

Early Toxicity Studies

Toxicity studies were conducted on a variety of animal species. The studies are summarized in Table 38. All animals were assessed on the basis of daily clinical observation while receiving the injections on days, 14, 21 and 30 thereafter. No adverse effects were noted throughout the period that injections were administered or during the follow-up period (one month for all species except the dogs which were followed for 4 months).

TABLE 38

Summary of Early Toxicity Studies

| Animal | Quantity | Dose |
|---|---|---|
| White Mice | 100 | 0.2 ml i.m. at three day intervals four times |
| Male Wistar Rats | 100 | 2.0 ml i.m at three day intervals four times |
| Golden Hamsters | 60 | 1.5 ml i.m. at four day intervals four times |
| Guniea Pigs | 60 | 3.0 ml at three day intervals four times |
| Rabbits | 15 | 5.0 ml i.m. at three day intervals four times |
| Cats | 10 | 3.0 ml i.m. at three day intervals six times |
| Dogs | 12 | 2 ml/kg i.m. given once - observed for four months** |

Hematologic data collected every third day for the first 30 days and once monthly thereafter.

A toxicity study was conducted to determine the effect of a single large intramuscular dose of the composition. Thirteen rats received a single intramuscular dose of 5 ml/kg of the composition. Three rats were observed for 7 days. Ten rats were observed for 14 days followed by euthanasia and necropsy. No symptoms of toxicity were observed in either group and no gross pathologic findings were observed in the animals that were necropsied. Based on these observations the $LD_{50}$ for intramuscular administration of the composition in rats was determined to be greater than 5 ml/kg. Table 39 summarizes these results.

TABLE 39

Estimation of $LD_{50}$ on Sprague-Dawley Rats

| Animal | Quantity | Admin. | Dose | Route of Units/kg* | LD50 |
|---|---|---|---|---|---|
| Sprague Dawley Rats | 3 male 10 (5 male/ 5 female) | i.m. i.m. | 5 ml/kg 5 ml/kg | 52.5 52.5 | >5 >5 ml/kg |

*Units calculated on the expected range of bioactivity of Lot #B0201 measured at 10.5 units/ml.

Toxicity Trial In Dogs

In a study conducted by the Ontario Veterinary College, the composition was administered to two mixed breed dogs. The protocol is summarized in Table 40. In each case one dose was given in the right leg and the second dose 7 days later was given in the left rear leg. Both dogs were observed for 14 days after the first injection. Appetite, activity, temperature, pulse rate, respiratory rate were monitored twice daily throughout the study. Routine urinalyses, hematology and serum chemistry profiles were performed, pretreatment and 24 hours, 72 hours, 7 days and 14 days after the first injection. Neither animal showed signs of pain associated with either injection. There was no evidence of anaphylaxis associated with the second injection. No abnormalities or changes in physical or laboratory parameters were observed that could be attributed to the drug. The drug appeared to be well tolerated by healthy dogs.

TABLE 40

Toxicity Study in Dogs

| Animal | Age and Weight | Dose 1 Units Calculated* | Dose 2 Units Calculated* | Dose Interval |
|---|---|---|---|---|
| Male Mixed Breed | Adult 5 kg | 5.5 ml i.m. 28.6–50.6 Units | 0.6 ml i.m. 3.1–5.5 Units | 7 days |
| Female Mixed Breed | 6 months 13 kg | 12.5 ml i.m. 65.0–115.0 Units | 1.3 ml i.m. 6.8–12.0 Units | 7 days |

Treatment of Animals with Malignant Neoplasmas

The composition of the invention was used clinically in a veterinary hospital for the treatment of various malignant tumors in companion animals. Eleven cats and ten dogs with advanced neoplastic disease that was not responding to conventional therapy were treated with the composition given intramuscularly in weekly doses. Table 41 summarizes the individual clinical cases in this study. The number of injections ranged from 2 to 69, with volumes up to 7.5 ml given into a single intramuscular site. Protocols of weekly injections allowed for examinations and careful monitoring of the individual cases with diagnostic tests determined individually for each case. The clinician noted that there was no local irritation nor severe allergic reactions, including anaphylaxis. The clinician and the owners of the animals did not observe any systemic adverse reactions. The investigators noted some clinical improvements consisting of minor reductions, improved appetite and activity levels, significant weight gain in a few animals and a decrease in pain and/or discomfort.

TABLE 41

Table 5-5 Summary of Results from Treatment of Animals with Malignant Neoplasms

| No. | Name-Age | Species-Sex | Diagnosis | From-To | Injections | Surgeries | Results |
|---|---|---|---|---|---|---|---|
| 01 | Bandit - 13 | Canine-M/n | Orinasal Fibrosarcoma | 01.31.87–05.19.87 | 16 | 3 | Minor Partial Response Progressive Disease Euthanasia |
| 02 | Bob - 5 | Feline-M/n | Focal Osseous Metaplasia with Osteosarcomatous development, Spindle Cell | 04.02.87–08.10.87 | 18 | 11 | First recurrence 16 months all complete response |
| | | | Sarcoma, Feline Fibrosarcoma, Squamous, Recurrent Spindle Cell Sarcoma - invasive (necropsy diagnosis) | 11.08.88–02.21.90 | 69 | | Response with subsequent treatment evolving to Progressive Disease (tumor became Rapidly invasive) Euthanasia |
| 03 | J. D. - 7 | Canine-M/n | Oral Amelanotic Melanoma, Benign Papilloma Recurrent Round Cell Sarcoma | 03.02.02.03.87 08.24.87 12.14.87–04.05.88 04.04.89–08.01.89 11.09.89–11.30.89 241290 25029189 | 26 20 14 17 15 4 94 | 3 | Complete Response. Currently Asymptomatic (4 months) |
| 04 | Mimi - 7 | Canine-F/s | Invasive Fibrosarcoma recurrent | 02.27.87–08.10.87 | 22 | 5 | Stable (No Change), Limb amputation. No recurrence |
| 05 | Goliath - 17 | Feline-M/n | Malignant Melanoma Fibrosarcoma | 04.02.87–09.14.87 11.30.87–07.25.88 | 22 31 | 3 | Initial Major Partial Response. Subsequent Minor Partial Response. Progressive Disease Euthanasia. |
| 06 | Diablo - 15 | Feline-M/n | Malignant Squamous Cell Carcinoma | 05.28.89–06.29.87 | 5 | 1 | Initial Minor Response Then Progressive Disease Euthanasia |
| 07 | Oliver - 10 | Canine-M/n | Malignant Round Cell Sarcoma | 02.24.89–05.30.89 | 12 | 1 | Complete Response. Asymptomatic 1 year. |
| 08 | Karu - 7 | Canine-M/n | Mucinous Intestinal Carcinoma - Metastatic | 06.01.87–09.14.87 | 14 | 1 | Minor Partial Response. Then Progressive Disease. Euthanasia |
| 09 | Puppy - 12 | Feline-M/n | Ceruminous Gland Adenocarcinoma | 07.22.88–10.04.88 | 10 | 1 | Minor Partial Response. Then Progressive Disease. Died 10.10.87 |
| 10 | Grandpa - 16 | Feline-M/n | Anaplastic Neoplasm High Grade Malignancy | 01.17.89–03.20.89 | 9 | 2 | Minor Partial Reponse. Then Progressive Disease. Euthaniasia 03.26.87 |
| 11 | Sam - 7 | Feline-F/s | Mediastinal Lymphoma | 11.02.87–12.21.87 | 7 | 0 | Minor Partial Response. Then Progressive Disease. Died 12.21.87 |
| 12 | Pete - 3 | Feline-M/n | Acute Feline Leukemia | 04.13.87–05.11.87 | 5 | 0 | Transient Minor Partial Response. Then Progressive Disease. Died 05.05.87 |
| 13 | Midnight - 8 | Feline-M/n | Feline Leukemia | 11.24.87–01.01.88 | 2 | 0 | Progressive Disease Euthanasia 01.07.88 |
| 14 | Stormy - 10 | Canine-M/n | Amelanotic Melanoma | 03.02.87–07.04.87 | | | Complete Response, Recurrence After Nine Months, Progressive Disease |
| 15 | Penny - 10 | Canine-F | Malignant Melanoma | 03.02.87–07.08.87 | | | Partial Response(?) Progressive Disease |
| 16 | Muky - 5 | Feline-F | Anaplastic Carcinoma | 02.09.87–06.08.87 | 6 | 3 | Complete Response, Recuirrence After Three Months Stable |
| 17 | George - 10 | Feline-M | Malignant Melanoma | 03.02.87–08.04.87 | 15 | 1 | Minor Partial Response, No Change After 26 Months Stable |
| 18 | Simon - 13 | Canine-M | Benign Prostatic Hyperplasia | 04.02.87–08.31.87 | 10 | 1 | Minor Partial Response |
| 19 | Tequila - 14 | Canine-F/s | Malignant Intestinal Adenocarcinoma | 11.24.89–8.09.90 | 35 | 1 | Minor Partial Response Euthanasia 08.09.90. |
| 20 | Sheba - 12 | Canine-F/s | Invasive Osteosarcoma Skull | 12.06.89–06.28.90 | 25 | 1 | Initial Minor Partial Response. Then Progressive Disease Euthanasia |

TABLE 41-continued

Table 5-5 Summary of Results from Treatment of Animals with Malignant Neoplasms

| No. | Name-Age | Species-Sex | Diagnosis | From-To | Injections | Surgeries | Results |
|---|---|---|---|---|---|---|---|
| 21 | Mesha - 14 | Feline-F/s | Osteosarcoma | 02.07.89–05.06.89 | 13 | 2 | Limb Amputation. Complete response. No recurrence or metastases 1 yr. |

The clinical results are summarized as follows: Six animals (3/10 canines and 3/11 felines) experienced complete response. One animal (1/11 felines) had initial major partial response. Eleven animals (5/10 canines and 6/11 felines) experienced minor partial response. One animal (1/10 canines) remained stable and one animal (1/11 felines) did not respond. Table 42 provides definitions of each treatment. The clinical experience in animals suggested a potential role for the composition in the treatment of malignant neoplasms.

TABLE 42

Definitions of Treatment Responses

| Response | Definition |
|---|---|
| Complete Response | Disappearance of all clinical evidence of active tumors. The patient must be free of all known disease as determined by two observations not less than four weeks apart. |
| Partial Response | |
| Major | Where there is a greater than 50% reduction in the sum of the product of the perpendicular dimension of all measurable tumor with no new lesions appearing elsewhere. |
| Minor | Where there is a 25–50% shrinkage in the sum of the products of the perpendicular diameters of all measurable tumors; or subjective responses such as improvement in performance status, appetite and feeling of well being; or tumor necrosis or lysis as seen on ultrasound, x-rays, or changes in consistancy and character of the tumors suggesting a decrease in adhesion and an increase in tumor mobility. |
| Stable Disease | Less than 25% increase or decrease in the size of one or more measurable lesions without tumoral lysis, or appearance of new lesions. |
| Progressive Disease | Increase of 25% in the size of one or more measurable lesions without tumoral lysis, or appearance of new lesions. |

EXAMPLE 19

Preliminary Clinical Trials

Patients with untreatable tumors were treated with 0.11 ml per kilogram of the composition of the invention as prepared in accordance with the methods set out in Example 1. The composition was given intramuscularly every three to five days. Of the 58 patients treated there was absolutely no significant toxicity. In the 37 evaluable patients three patients had minor responses i.e. tumor shrinkage of between 25 and 50 percent, and five patients had stable disease of at least eight weeks of duration. The most interesting results were in the pancreatic patients who seemed to have the most encouraging results. Of the seven patients one patient had the disease stabilization for a full 11 months. And a second patient with extremely advanced disease had disease stabilization for four months. It was based on these results that carcinoma of the panaceas was selected for a basic study of the composition of the invention. The objective of the study was to determine the safety and efficacy of the composition in this group of patients.

The treatment consisted of the composition of the invention 0.11 ml per kilogram with a minimum dose of 7.5 ml given as a single deep intramuscular injection to the gluteus maximus. Patients received the treatment three times weekly during the first week and then twice a week until disease progression. In all, 22 patients were enrolled in this study and all were evaluable for toxicity. Only 17 patients were evaluable for efficacy. With a total of 570 injections there was no toxicity of any kind reported in either local or systemic. There were also no objective responses. Six patients however had stable disease for three months or longer but the rest of the patients progressed within the first three months. The median survival was eight months from the time of diagnosis. There was a median survival of four months from the first injection. There were three patients who had stable disease for longer than six months. One patient, a 75 year old man relapsed with liver metastasis 18 months after a liberal procedure. He remained absolutely stable on the composition for eight months before progressing. A 71 year old woman with unresectable disease remained stable for at least ten months and continued to work full time. A 64 year old woman who relapsed regionally four months after the procedure was stable for at least eight months.

A fourth patient who had inoperable carcinoma of the panaceas and could not be enrolled in the study because tissue could not be obtained for a pathologic diagnosis, was stable for almost a year although his tumor progressed despite higher doses of the composition. In summary, the composition has no site of toxic activity against pancreatic cancer at this dosage schedule. There was a suggestion of temporary anti-proliferative activity in a minority of cases with this disease using the composition.

EXAMPLE 20

Pancreatic Cancer Clinical Studies

A Phase II trial with the composition of the invention was begun for patients with measurable, biopsy-proven pancreatic cancer. The composition was administered as a 7.5 ml (0.11 ml/kg) intramuscular injection 3 times weekly for 1 week then twice weekly until disease progression. Details of the study are set out below.

Method

Treatment consisted of the composition prepared as in Example 1, 0.11 ml/kg (minimum dose 7.5 ml) administered with a single deep intramuscular injection to the gluteus maximus, alternating buttocks with each dose. Patients received 3 injections during the first week followed by twice-weekly injections until tumor progression.

Response was defined using standard criteria. Miller et al., Cancer 1981; 47:207–214). A complete response (CR) was defined as complete disappearance of all evidence of disease for at least 4 weeks. A partial response (PR) was defined as ≧50% reduction in the product of the two largest perpendicular diameters of the largest measurable lesion, for at least 4 weeks. Progressive disease was defined as a 25%, or more increase in the size of one or more measurable lesions or the appearance of new lesions. Disease not meeting criteria for response or progressive disease was termed stable disease.

Results

A total of 22 patients were enrolled in the study, but five patients were considered inevaluable for efficacy. There were no complete or partial responses. Three patients had disease progression within the first month. Six patients had disease stabilization for more than 3 months (3.5, 3.5, 5, 8, 12+, 14+). Median survival for the entire group was 8 months from the date of diagnosis and 5 months from the start of treatment. One patient with biopsy-proven liver metastases and a CEA of 37 ng/ml (normal <3 ng/ml), had absolute stabilization of the liver metastases and CEA for 8 months. One had stable disease for 5 months. One patient had disease relapse in her pancreatic bed 4 months after a Whipple procedure and was been stable on the composition for at least one year, with the exception of a slowing rising CEA. A third patient had a percutaneous stent inserted and continued to work full-time for at least 14 months with no evidence of tumor progression.

All 22 patients were evaluable for toxicity, having received a total of over 500 injections. None developed any clinical or laboratory evidence of drug-related toxicity. There was no detrimental effect on Quality of Life which generally paralleled disease activity. No significant changes in total white blood cell counts, absolute lymphocyte counts on serum immunoglobulins were seen.

Figure 13:
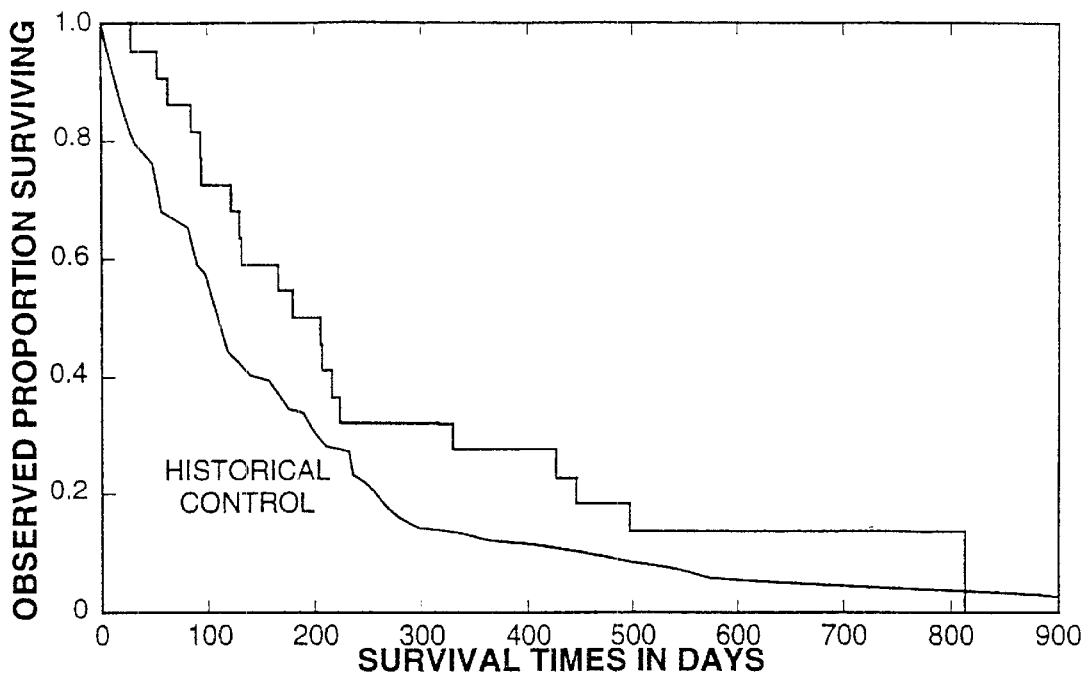
FIG. 13 is a graph showing survival taken from diagnosis of pancreatic cancer patients treated with the composition of the invention.
Figure 14:
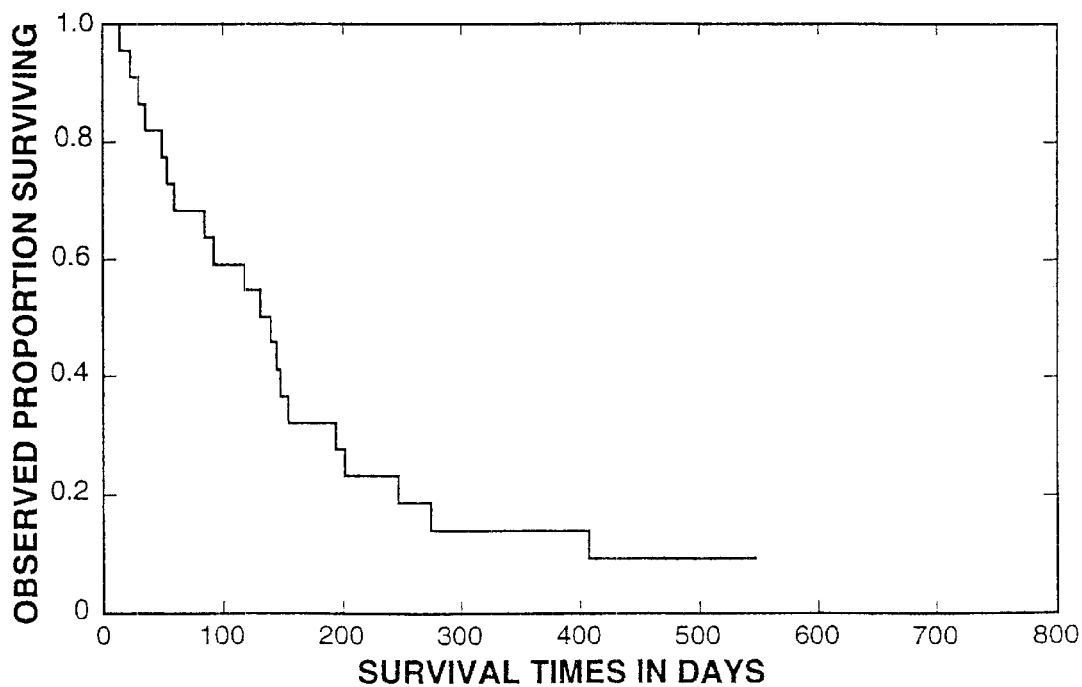
FIG. 14 is a graph showing survival taken from treatment of pancreatic cancer patients treated with the composition of the invention.

Survival curves representing the survival times from diagnosis and from treatment initiation are presented in FIGS. 13 and 14, respectively. For comparison, an historical survival curve for Gudjonsson (1987) has been superimposed in FIG. 13. Another example of a comparable historical survival curve may be found in Bakkevold, Petterson, Arnesjo and Espenhaug (1990).

The results of the survival analyses are summarized in Table 43. The mean survival time for diagnosis was 281 days (FIG. 13). The median survival was 182 days (approximately 5 months). For comparison, Gudjonsson (1987) reported the mean survival of his 188 surgical patients as 208 days with a media survival of 120 days. The mean survival time from treatment start was 166 days (FIG. 14). The median survival was 133 days (approximately 4 months and 1 week).

TABLE 43

Protocol CO2-104 Survival Estimates

| Survival | Patient Population | Mean Survival (days) | Standard Deviation | Median Survival (days) |
|---|---|---|---|---|
| From diagnosis | Protocol CO2-104 patients | 281 | 203 | 182 |
| | Protocol CO2-104 evaluable patients | 304 | 157 | 219 |
| From treatment start | Protocol CO2-104 patients | 166 | 135 | 133 |
| | Protocol CO2-104 evaluable patients | 220 | 132 | 146 |

Survival times were also estimated among a subset of evaluable patients who had each received at least 13 injections. Fourteen of the 22 patient were evaluable. Among these patients (Table 43), the median survival from diagnosis was 219 days (approximately 7 months and 1 week). The median survival from treatment start was 146 days (approximately 5 months).

EXAMPLE 21

Clinical Trials re Malignant Melanoma

Advanced malignant melanoma was defined to include all stage III or IV patients and all loco-regional or distant relapses occurring after primary treatment. The standard treatment by which all other treatments are judged is DTIC (dacarbazine) which has a reported response rate of about 15%. The median response is 3–6 months, and carries with it severe nausea and vomiting, and a potentially lethal side effect of acute liver necrosis by thrombosis of the hepatic veins. This treatment fails to show any definitive survival advantages.

This study was conducted to determine the safety and efficacy of the composition of the invention and to determine its effect on survival and on quality of life, when used in patients with advanced malignant melanoma. The study, was a non-comparative, multicenter trial.

An initial dosing schedule of 7.5 ml injections of the composition of the invention intramuscularly 3 times per week was used. After no organ or marrow toxicity was observed, the loading schedule was increased to daily injections for 15 days, followed by maintenance of 3 injections per week. Subsequently the loading dose was increased to 30 days. Duration of treatment was 36 weeks and then reduced to 16 weeks, after which patients were given the option of entering a continuation protocol.

Thirty-three patients with advanced melanoma were included in the study population (17 females and 16 males), ranging in age from 17 to 85 years of age. 64% had been previously treated and 36% were untreated. Of the 33 patients included in the study population, twenty-five were evaluable. The Karnofsky Performance Status (baseline) was in the range of 40–100%, median 80%. Eleven patients were alive at the end of the study period and five of these were under treatment.

A minor partial response was observed in 16/33 patients (48%). One patient had a reduction of 33% in the lungs, six patients had pain reductions and eight patients gained more than 1000 grams in weight for more than a month (Range 1000–2600 grams). A stable condition was observed in 19/33 patients (58%) (Range 60–170 days, median 77 days).

Figure 15:
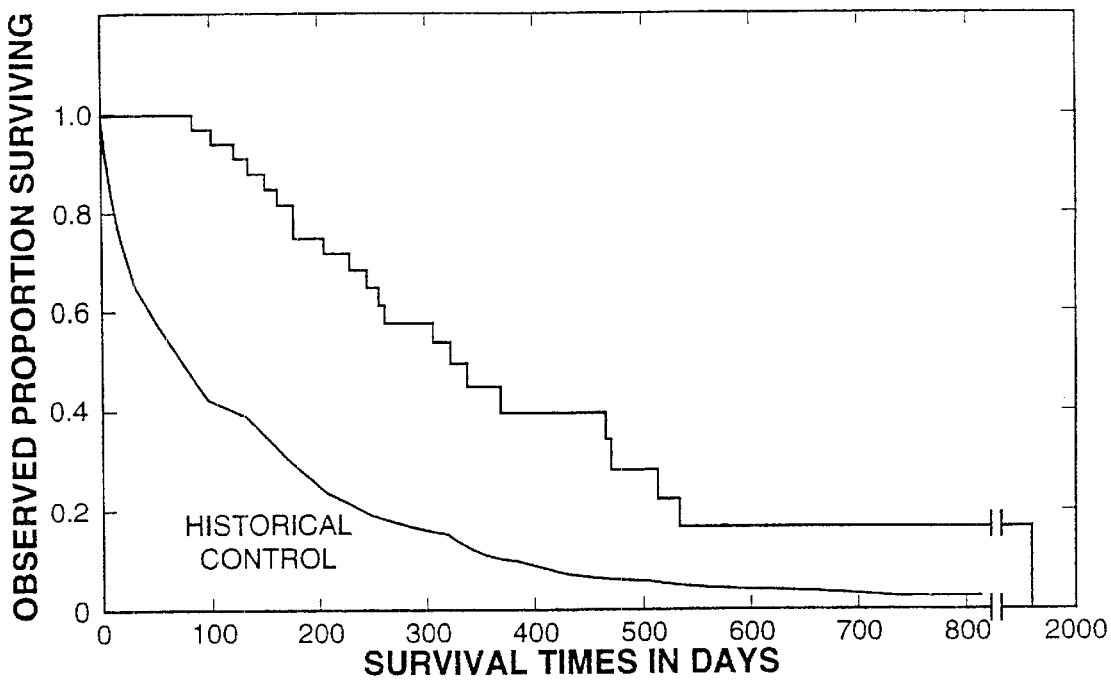
FIG. 15 is a graph showing survival of all melanoma patients treated with the composition of the invention.
Figure 16:
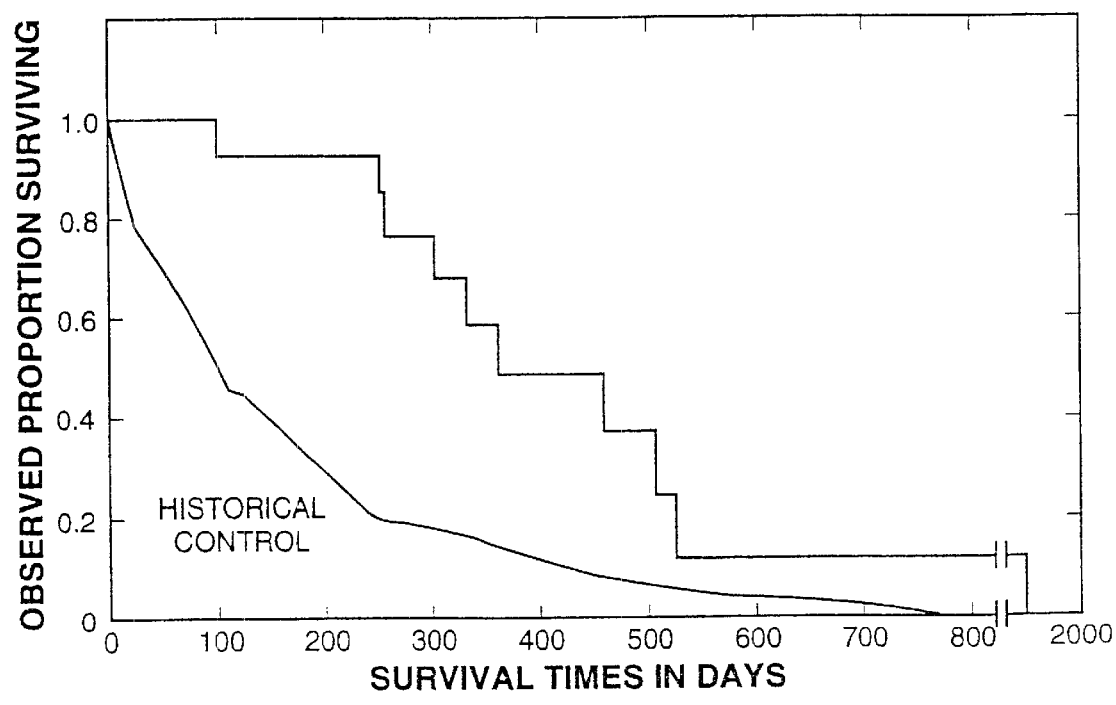
FIG. 16 is a graph showing survival of melanoma patients with two or more tumor sites treated with the composition of the invention.
Figure 17:
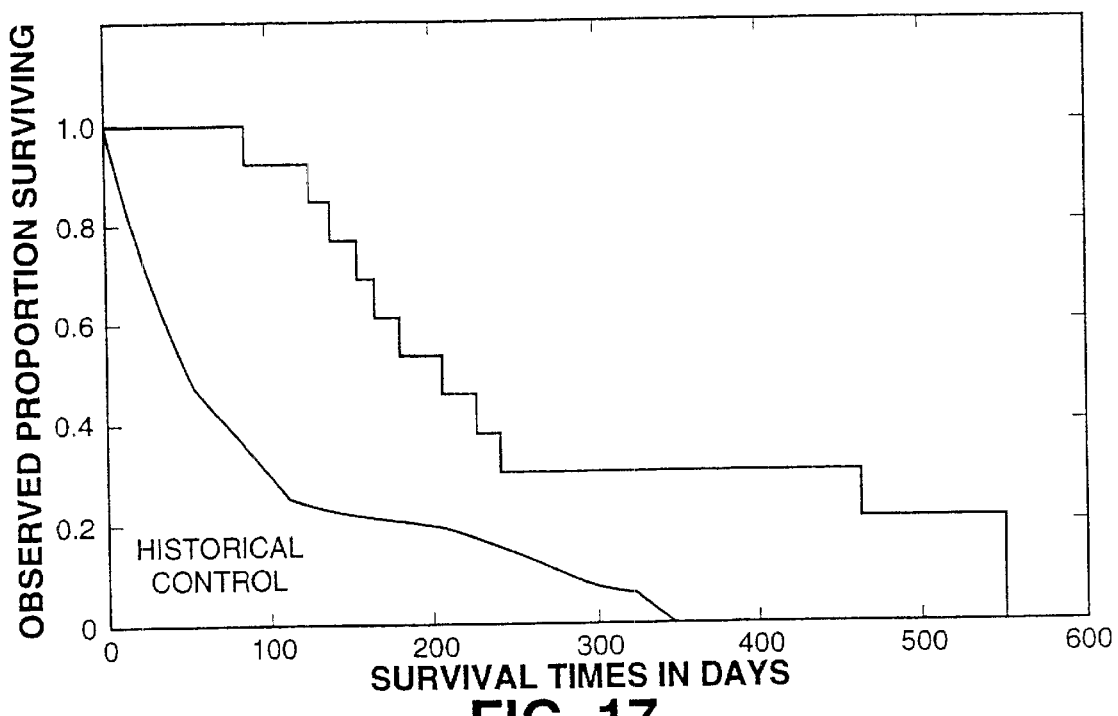
FIG. 17 is a graph showing survival of melanoma patients with three or more tumor sites treated with the composition of the invention.

FIGS. 15, 16 and 17 show the survival of patients treated with the composition of the invention compared to historical controls, measured as survival from diagnosis of metastases/recurrence in days. The solid line represents the survival curve for patients treated with the composition of the invention and the broken line represents the historical survival curve (Balch, C. M. et al., *Cutaneous Melanoma*, 2nd. ed. 1992, Chps. 14 and 39, pp. 165–187 & 499–508, Lippincott Co., Philadelphia, Pa.). The survival of all patients treated with the composition of the invention, including patients with one to over three tumor sites, is shown in FIG. 15. Survival of patients with two tumor sites and with three or more tumor sites is shown in FIGS. 16 and 17 respectively.

The group of all patients treated with the composition of the invention had a 39% survival (Kaplan—Meier estimation) at one year. The survival rate at one year for all advanced malignant melanoma (AMM) patients is approximately 11% in historical controls (matched by number of tumor sites). The group had a median survival of 315 days compared to the historical median of 89 days.

With two tumor sites the one year survival was 49% in the patients treated with the composition of the invention, as compared with 13% in historical controls. This group had a median survival of 360 days compared to the historical median of 120 days. With three or more tumor sites the one year survival was 31% in the patients treated with the composition of the invention, as compared with 0% in historical controls. The group with three or more tumors had a median survival of 205 days compared to the historical median of 60 days.

Quality of life was assessed by weight gain, performance status (Karnofsky), Quality of Life Index (Spitzer) and pain scale (Linear Analogue). Weight gain over time is shown in Table 39.

TABLE 41

| | Number of patients/evaluable | | | | | |
|---|---|---|---|---|---|---|
| | 1st month | 2nd month | 3rd month | 4th month | 5th month | 6th month |
| | 11/25 | 12/25 | 4/25 | 4/25 | 1/25 | 1/25 |
| Percent (%) | 44% | 48% | 16% | 16% | 4% | 4% |
| Range (gr) | 100–2400 | 200–6000 | 100–1000 | 100–2000 | | |
| Average (gr) | 900 | 1480 | 525 | 775 | 100 | 2000 |

The Karnofsky and Spitzer scales are both subjective and were found to approximately agree in each individual. Fifteen patients reported no change in these parameters. Four patients showed fluctuations which later returned to previous levels. One patient had a decrease (from 40–20%).

The results of pain evaluation showed that in six patients by week 4 the pain dropped from 5 (worst possible) to 2 (moderate) or 0 (no pain). One patient had a drop in pain from 3 to 0. One patient with hepatic metastasis had pain reduction to 0 and stabilisation for 11 months. Nine patients who entered the study with 0 pain maintained that level throughout the study. Five patients had a moderate (2 unit) increase in pain. Three patients had transient pain increases (1 to 2 units) during the second or third month.

Out of 1734 injections administered to 33 patients, 21 patients had no adverse drug reactions. Fourteen adverse drug reactions were reported in 12 patients. The adverse drug reactions usually occurred at weeks 4 or 8 and were mild to transient, and most frequently were a low grade fever.

The difference in survival between the historical groups and the protocol groups treated wit the composition of the invention suggests a survival benefit for patients treated with the composition of the invention. The cancer seemed to stabilize in 19 patients. All patients treated for AMM were included in the survival data. Also included were 21 previously treated patients (many clinical trials require untreated patients, because of the poor prognosis of failed previous treatments). The tumor burden was high (82% had more than one metastatic site).

The survival and quality of life data suggest that most patients received some benefit from the treatment. Eleven patients were still alive at the end of the study period and of those 11, 5 continued treatment.

EXAMPLE 22

Pathology Protocol Malignant Melanoma

The following is a report of a 73 year old female with progressive malignant melanoma of the hard palate and gums. When the malignant melanoma was viewed under the microscope, looking from top to bottom, one can see the epithelial layer with accompanying keratin, beneath which the malignant cells start to become more apparent. These melanoma cells can be seen to be rounded or oval, with an abundant eosinophilic cytoplasm, and pleomorphic hyperchromatic nuclei. These cells have substituted the normal submucosal tissue. The blood vessels which are seen appear normal, and there is a paucity of any kind of inflammatory/immune response as would be represented by the presence of leukocytes (polymorphonuclear and mononuclear cells). This is an example of tumor tissue which is thriving, i.e. the tumoral architecture is intact.

A tumor tissue sample from the same patient, who had been treated with the composition for two months was observed. Starting from top to bottom, one can see that the continuity of the epithelium has been disrupted by a necrotic process. This necrosis, while common in the center of any tumor that has reached a critical mass, is rarely seen on the periphery, especially in malignant melanoma, and is a sign that the host's immune response is mounting an attack against the tumor. Throughout the tissue are a massive number of cells different from the original tumor cells. These are the immune cells-neutrophils, lymphocytes, macrophages—which have orchestrated the disruption of the typical tumoral architecture. The blood vessel walls have become densely infiltrated with a large number of host immune cells (arrow). This cellular infiltrate subsequently will cause the destruction of the blood vessel, which in turn prevents the tumor from receiving its supply of nutrients and oxygen (ischemic necrosis). This immune response which contributed to the tumoral disruption seen in this patient's tissue slide is consistent with reported changes known to be brought about by TNF (tumor necrosis factor) and with the results of the work described in the previous examples.

The immune response demonstrated in the after treatment with the composition strongly links the in vitro TNF immune modulation by the composition with known in vivo antitumoral TNF effects.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

EXAMPLE 23

Isolation of Active Fractions

A 300 ml sample of the composition was evaporated to dryness on a rotovap in which the temperature of the bath did not exceed 40° C. In order to ensure that the solution remained basic during the evaporation, 5 drops of a concentrated ammonium hydroxide solution was added every half hour to the composition until the evaporation was complete. The resulting residue had a weight of 11.6 g.

20 ml of a 10% concentrated ammonium hydroxide in methanol solution was then added to 2 g of the above residue. The insoluble material was filtered off and the filtrate was chromatographed through 101.93 g of 60 Å flash silica gel in a column with dimensions of 5 cm×12.5 cm. The solvent system used was 10% concentrated ammonium hydroxide in methanol solution. The column was run at a pressure of 10 p.s.i. and a flow rate of 11 ml/min. After 100 ml of solvent had passed through the column, twelve 20 ml. fractions were collected. The collection of these fractions correlated to the appearance of an off-white band that was quickly moving down the column.

Thin layer chromatography (TLC) of these fractions was run on silica gel plates in a 10% concentrated ammonium hydroxide solution in methanol and visualized with a ninhydrin spray. Fractions having similar TLC profiles were combined, resulting in the following fraction combinations, which were dried on a rotovap.

| Fractions | Volume Through Column to Obtain Fraction | Yield (g) |
|---|---|---|
| 1–4 | 100–180 | 0 |
| 5–6 | 180–220 | 0.1175 |
| 7–8 | 220–260 | 0.1969 |
| 9–10 | 260–300 | 0.0151 |
| 11–12 | 300–340 | 0.0053 |

Fractions 5–6, 7–8 and 9–10 had a positive reaction with ninhydrin at an $R_f$ value of 0.81.

EXAMPLE 24

Fractions 5–6 and 9–10 from Example 23 were tested in vitro for anti-proliferative effect (in accordance with the procedure of Example 4) and TNF stimulation (in accordance with Example 9). The results are shown below:

| FRACTION | ASSAY | ACTIVITY |
|---|---|---|
| 5–6 | Anti-Proliferative Effect | 11.57 units/mg |
| 5–6 | TNF Stimulation - LPS | 50 pg/ml |
| 9–10 | Anti-Proliferative Effect | 2.6 units/mg |
| 9–10 | TNF Stimulation - LPS | 1814 pg/ml |

Thus, fraction 5–6 was an active anti-proliferative, and fraction 9–10 was an extremely active TNF stimulator, and a moderately active anti-proliferative.

EXAMPLE 25

Samples of Fraction 5–6 was analyzed by Electron Impact Mass Spectroscopy (EI MS) and Electrospray Mass Spectroscopy to identify specific compounds likely to be present in the fraction. The Electrospray MS was performed on a Perkin-Elmer Sciex API-III spectrometer, using 5% acetic acid in water as the solute. In some instances, methanol was added to aid dissolution. The EI MS using a direct insertion probe was performed on a VG Analytical model ZAB-SE spectrometer using glycerol as a matrix, and using a DCI probe on a Kratos Analytical Profile Mass Spectrometer.

A review of the resultant spectra indicated that the following compounds were likely present in Fraction 5–6: phosphocholine, taurocholic acid, choline-stearic acid diglyceride, stearic acid, stearic acid diglyceride, palmitic acid-stearic acid diglyceride, and a sphingosine-oleic acid conjugate.

EXAMPLE 26

100 ml of the composition was acidified with 4 ml of a 1N HCl solution such that the pH of the composition was equal to 3. The composition was then extracted with three 100 ml. portions of HPLC grade dichloromethane. The dichloromethane fractions were then combined and dried over a small amount of anhydrous sodium sulfate. The dichloromethane solution was then filtered through paper into a round bottom flask and evaporated to dryness on a rotovap to yield 0.0049 g of a brown film.

0.0017 g of this film was dissolved in a 214 ppm $NH_3 \cdot H_2O$ solution at pH 7, and was screened for anti-proliferation activity as is set forth in Example 4. This screen revealed that the solution was an active anti-proliferative, with an activity of 14 Units/mg.

EXAMPLE 27

Example 23 was repeated on a larger scale, as follows. 10 ml of a concentrated ammonium hydroxide solution was added to 900 ml of the composition and the resulting solution evaporated to dryness on a rotovap in which the temperature of the bath did not exceed 40° C. In order to ensure that the solution remained basic during the evaporation, 5 drops of a concentrated ammonium hydroxide solution was added every half hour to the composition until the evaporation was complete, leaving a residue.

150 ml of a 10% concentration ammonium hydroxide in methanol solution was then added to the total residue. The solution was sonicated for 15 min. and the insoluble material was filtered off. The filtrate was chromatographed through 1695 g of 60 Å flash silica gel in a column with dimensions of 30 cm ×12 cm. The solvent system used was 10% concentration ammonium hydroxide in methanol solution. The column was run at a pressure of 6 p.s.i. and a flow rate of 30 ml./min. The results of the column are summarized in the table below.

| Fraction # | Volume of each fraction (ml.) | Observations |
|---|---|---|
| 1 | 550 | colorless |
| 2 | 450 | colorless |
| 3 | 400 | colorless |
| 4 | 150 | colorless |
| 5 | 100 | colorless |
| 6–7 | 75 | colorless |
| 8–13 | 50 | colorless |
| 14 | 50 | tan colored solution begins to elute |
| 15–35 | 50 | tan colored solution |
| 36–40 | 50 | colorless |

TLC was run on silica gel plates in a 10% concentration ammonium hydroxide solution and visualized with a ninhydrin spray. Fractions having similar TLC profiles were combined, resulting in the following fraction combinations, which were dried on a rotovap.

| Fraction # | Volume Through Column to Obtain Fraction | Yield (g) | Comments |
|---|---|---|---|
| 3 | 1000–1400 | 0.0504 | white powdery solid |
| 4–5 | 1400–1650 | 0.0855 | white powdery solid |
| 6–3 | 1650–1850 | 0.1555 | white powdery solid |
| 9–12 | 1850–2050 | 0.3014 | white powdery solid |
| 13–14 | 2050–2150 | 0.3595 | white powdery solid |
| 15–16 | 2150–2250 | 0.6914 | slight brown color - solid is tacky |
| 17–18 | 2250–2350 | 1.0284 | tan color - solid is clumpy |
| 19 | 2350–2400 | 0.3432 | tan color - solid is clumpy |

-continued

| Fraction # | Volume Through Column to Obtain Fraction | Yield (g) | Comments |
|---|---|---|---|
| 20–23 | 2400–2600 | 1.1531 | brown color - solid is clumpy |
| 24–30 | 2600–2950 | 0.3517 | brown color - solid is clumpy |
| 31–34 | 2950–3150 | 0.0813 | brown oil |

All fraction combinations from 15–16 through Fraction 31–34 had a positive reaction with ninhydrin at an $R_f$ value of 0.87, a value vary similar to the $R_f$ value for the active fractions of Example 23. Fractions 24–30 and 31–34 had an additional positive reaction with ninhydrin at an $R_f$ value of 0.85.

EXAMPLE 28

Fractions 4–5, 15–16 and 17–18 were tested in vitro for anti-proliferative effect (in accordance with Example 4) and TNF stimulation (in accordance with Example 9). The results are shown below:

| Fraction | Assay | Activity |
|---|---|---|
| 4–5 | Anti-proliferative Effect | 4.7 units/mg |
| 4–5 | TNF Stimulation | — |
| 15–16 | Anti-proliferative Effect | 4.5 units/mg |
| 15–16 | TNF Stimulation | — |
| 17–18 | Anti-proliferative Effect | 3.9 units/mg |
| 17–18 | TNF Stimulation | — |

Thus, fractions 4–5, 15–16, and 17–18 showed anti-proliferative activity, but no TNF stimulation activity. Elemental analysis of the above fractions showed them to be high in $NH_4Cl$, which inhibits TNF production.

EXAMPLE 29

Sample of fractions 15–16 and 24–30 was dialyzed and then was analyzed by mass spectroscopy, using the methods described in Example 25. Undialyzed samples from fractions 17–18 and 24–30 were also analyzed. A review of the resultant spectra indicated that the following compounds were likely present: glycocholic acid, a trihexosamine trimer, and taurocholic acid (Fraction 15–16); stearic acid, and a hexasamine dimer; and glycocholic acid (Fraction 24–30).

EXAMPLE 30

The composition was dialyzed in separate dialysis tubing as follows:

100 ml of the composition was placed inside a Spectra/Por® CE membrane tubing which had a molecular weight cut off of 11. The ends of the tubing were sealed with clips and the tubing was placed into a stirred bath of 10 L of distilled water. The dialysis was monitored daily by removing 1 ml. of solution from the dialysis tubing and adding 3–4 drops of a 1/10 N silver nitrate solution. The presence of chloride indicated that the dialysis was not complete. If the dialysis was not complete the bath was replaced with fresh distilled water. Dialysis completion occurred after 3–4 days. After dialysis was complete, the dialyzed material was dried on a rotovap to yield an average of 0.3 mg of solid per ml of original volume.

A sample of the solid material was then dissolved in HPLC grade water, and TLC was run on silica gel plates in a 10% concentrated ammonium hydroxide solution in methanol, and visualized with a ninhydrin spray. A positive reaction with ninhydrin was obtained at an $R_f$ value of 0.83.

EXAMPLE 31

A sample of the solid material from Example 30 was also analyzed by mass spectroscopy, using the methods described in Example 25. A review of the resultant spectra indicated that the following compounds were likely present: a sphingosine-oleic acid conjugate, diacetyl sialic acid, a fucose-hexosamine dimer, deoxyglycocholic acid, taurocholic acid, a sialic acid-fucose dimer, and a di(fucose) hexosamine trimer.

EXAMPLE 32

Previous results indicated that the active components of the composition (at least according to a TNFα release assay) were present in the unbound fractions (void volume) after reversed-phase high performance liquid chromatography (RP-HPLC) on a C18 μBondapack column. As well, most of the mass (70%) of the composition extract, which was loaded onto a C18 μBondapack column, eluted in the void volume. These results suggested the active components of the composition are, very likely, very polar or even ionic molecules.

To further examine the above results, purification of the active components by ion-exchange chromatography was performed. Negatively charged active components (assessed by its anti-proliferation effect on tumor cells and not on normal cells, and as well by its TNFα release-inducing activity), if present, would thus become bound to an anion exchange resin.

Experimental Procedure 10 ml of total Virulizin extract was loaded onto an anion-exchange chromatography column (Bio-Rad AG-1, hydroxide form, total resin wet volume was 10 ml (column dimensions 1.5 cm×6.0 cm), equilibrated with Millipore deionized water). The volume of resin used was calculated to be sufficient for the binding of all the anions present in the extract. The unbound fraction was collected and reloaded onto the column in order to maximize the binding to the resin. The unbound fraction from this second passage was collected and saved. Any unbound material remaining on the column's void volume was removed by washing with deionized water (2×20 ml). Bound molecules were eluted with a step gradient of ammonium bicarbonate ($NH_4HCO_3$) (20 ml/step).

| The elution steps were | 0 M |
|---|---|
| | 0.1 M |
| | 0.2 M |
| | 0.3 M |
| | 0.4 M |
| | 0.5 M |
| | 0.6 M |
| | 1.0 M |
| | 1.5 M |

EXAMPLE 33

Samples from all the fractions of Example 32 were analyzed for anti-proliferation activity and TNF stimulation activity, in accordance with the procedures of Examples 4 and 9, respectively.

The results are shown below:

| Sample | Anti-proliferative activity (U/mg) | TNFα release-inducing activity-LPS (pg/ml) |
|---|---|---|
| 0 M | 0 | 35 |
| 0.1 M | 0 | −79 |
| 0.2 M | 0 | −76 |
| 0.3 M | 0 | |
| 0.4 M | 2.5 | |
| 0.5 M | 555.6 | |
| 0.6 M | 0 | 107 |
| 1.0 M | 0 | 105 |
| 1.5 M | 0 | 189 |

The results from the activity assays show that TNF production stimulation was found in the 0.6 M, 1.0 M, 1.5 M fractions. Anti-proliferation activity was found in fractions 0.4 M (minor activity) and 0.5 M (major active fraction).

EXAMPLE 34

Thin layer chromatography analysis of the active fractions revealed a mixture of several components. A sample of the 1.0 M fraction from Example 32 was analyzed by mass spectroscopy in accordance with Example 25. A review of the spectra generated suggested that the following compounds may be present: a sialic acid-glycerol dimer, cholesterol sulfate, and taurocholic acid.

EXAMPLE 35

Reversed Phase (C18) HPLC analysis was performed on a sample of the composition in accordance with the procedure of Example 2, except that (1) a Phenomenex WP60009-C18 column, 250×4.6 mm, was used, (2) the sample was lyophilized and then reconstituted in 0.1% trifluoroacetic acid (TFA) in water, and (3) 150 μl of the reconstituted sample was applied to the column.

Various fractions of eluent were collected, including a fraction which eluted at approximately 2.40–3.40 minutes after the reconstituted sample was applied to the column.

EXAMPLE 36

A sample of the fraction eluting at approximately 2.40–3.40 minutes from Example 35 was analyzed three times for TNF stimulation activity in accordance with the procedure of Example 9. The following results were obtained.

| Assay # | TNF Stimulation - LPS |
|---|---|
| 1 | 259 pg/ml ± 107 pg/ml |
| 2 | 311 pg/ml ± 14 pg/ml |
| 3 | 572 pg/ml ± 176 pg/ml |

EXAMPLE 37

A sample of the fraction eluting at approximately 2.40–3.40 minutes from Example 35 was subjected to tandem column reversed-phase (C18) HPLC as follows. The column from Example 35 was used in tandem with a Phenomenex prime-sphere HC-C18 column, 250×4.6 mm. The sample was lyophilized, reconstituted in 0.1% TFA in water (Buffer A) and 150 μl of reconstituted sample was applied to the column. Buffer A was run for twenty minutes, then a linear gradient of 0–80% of 0.1% TFA in acetonitrile (Buffer B) was run for 35 minutes. At the end of this period, 80–0% Buffer B was run for 5 minutes. Flow rate was 0.9 ml/min. Six eluent fractions were collected, at the following approximate times from injection:

| Fraction # | Time (min.) |
|---|---|
| 1 | 5.6–6.25 |
| 2 | 6.25–6.6 |
| 3 | 6.6–7.1 |
| 4 | 7.1–8.2 |
| 5 | 8.8–9.6 |
| 6 | 14.7–16 |

EXAMPLE 38

A sample of Fraction 1 ("1") and a sample of Fraction 2 ("2") from Example 37 were lyophilized and reconstituted in 214 ppm $NH_3 \cdot H_2O$. These reconstituted samples were then analyzed for anti-proliferative effect in accordance with the procedure of Example 4. The following results were obtained:

| Sample | Anti-proliferative Effect |
|---|---|
| 1 | 17.8 unit/ml |
| 2 | 0 |

EXAMPLE 40

Samples from each of the six fractions of Example 37 were analyzed by mass spectroscopy in accordance with Example 25. A review of the resultant spectra for the six fractions indicated that the following compounds were likely present: taurocholic acid, a sialic acid-glycerol dimer, NaCl, trimethylamine, methylethylamine, and propylamine.

EXAMPLE 41

Anti-proliferative effect, according to the method of Example 4, was measured for the following three samples: (1) 10–11 mg taurocholic acid in 2 ml of $H_2O$; (2) 214 ppm $NH_3 \cdot H_2O$; and (3) 0.7 mg of taurocholic acid in 4.0 ml of 214 ppm $NH_3 \cdot H_2O$. Neither sample (1) nor sample (2) had any detectable anti-proliferative effect. Sample (3), however, had an anti-proliferative effect of 14 units/mg.

This result indicates that bile acids, such as taurocholic acid, in combination with ammonium ions, exhibits anti-proliferative activity at concentrations below that which the components, tested individually, show no activity. Thus, the combination of these two components, apparently synergistically, affects anti-proliferative activity.

What is claimed is:

1. A substantially pure and consistently potent composition for use as an immunomodulator prepared by a process comprising:

(a) mixing bovine bile with an equal amount of a solvent to produce a bile/solvent solution;

(b) separating out the solvent to obtain a solution substantially free of solvent;

(c) removing bile pigments from the solution to obtain a colorless liquid;

(d) extracting the colorless liquid to obtain an aqueous phase;

(e) dialyzing the aqueous phase in a dilute buffer solution having a pH of about 7.0 to about 8.56;

(f) subjecting said dialyzed aqueous phase to a reversed phase HPLC column to obtain a substantially pure and consistently potent composition which has a consistently reproducible pattern on reverse-phase HPLC where peaks are seen early in the exclusion fraction at about 27 and 32 minutes; said composition consisting of:

small molecular weight components of less than 3000 daltons in a buffered salt solution having a pH of about 7.0 to about 8.56, not more than 10 ppm ethanol and not more than 5 ppm ether, and no measurable levels of IL-1$a$, IL-1$b$, TNF, IL-6, IL-8, IL-4, GM-CSF, or IFN-gamma, wherein said composition is capable of stimulating monocytes and/or macrophages in vitro, is capable of modulating tumor necrosis factor production, shows no cytotoxicity to human peripheral blood mononuclear cells, and is not an endotoxin.

2. The composition of claim 1, further comprising the step of adjusting the osmolarity of the aqueous phase so that the composition is hyperosmolar.

3. The composition of claim 1, further comprising the step of concentrating the colorless liquid to about one-eight the original volume of the bile/solvent solution.

4. The composition of claim 1, further comprising the step of concentrating the colorless liquid to about one-tenth the original volume of the bile/solvent solution.

5. The composition of claim 1, wherein the dialyzed aqueous phase has a finished fill volume of about 3 mL and has a biological activity of about 2.5 × compared to manufacturing processes resulting in about a 7.5 mL dosage fill volume.

6. The composition of claim 1, wherein the solvent is ethanol.

7. The composition of claim 1, wherein components responsible for the release of TNF from PBMN are obtained from the dialyzed aqueous phase.

8. The composition of claim 7, wherein the TNF-releasing components are precipitated by 80% acetonitrile.

9. The composition of claim 1, wherein the extraction is an ether extraction.

10. The composition of claim 1, wherein the dialyzed aqueous phase has a release of TNF to release of GM-CSF ratio of about 2:1.

11. The composition of claim 1, wherein said composition contains peptides and amino acids selected from the group consisting of glutamate/glutamine, glycine, asparagine, threonine, serine, alanine, ninhydrin positive residues, and mixtures thereof.

12. The composition of claim 1, wherein the bile pigments are removed from the solution by using activated charcoal.

13. The composition of claim 1, further comprising the step of removing residual ether from the aqueous phase by heating the solution up to 55° C. for about 5–15 hours.

14. The composition of claim 1, wherein the dilute buffer solution is obtained using dibasic and monobasic sodium salts as buffers.

15. The composition of claim 1, wherein said composition contains about 15–21 mg/ml solids and about 720–880 µg/ml amino acids.

16. The composition of claim 15, wherein less than 1% of the solids in said composition is organic material, there are no lipids in the solids, around half of the solids are carbohydrates, and the rest of the solids are amino acids.

17. The composition of claim 1, wherein the dialyzed aqueous phase which provides RP-HPLC peaks at about 27 and 32 minutes has a TNF release of at least 526±169 pg/ml for a 100 µl quantity.

18. A composition for use as an immunomodulator prepared by a process comprising:

(a) mixing bovine bile with an equal amount of ethanol to produce a bile/ethanol solution;

(b) separating out ethanol to obtain a solution substantially free of ethanol;

(c) removing bile pigments from the solution to obtain a colorless liquid;

(d) concentrating the colorless liquid to about one-eighth the original volume of the bile/ethanol solution;

(e) conducting an ether extraction on the colorless liquid to obtain an aqueous phase;

(f) adjusting the osmolarity of the aqueous phase so that the aqueous phase is hyperosmolar;

(g) concentrating the colorless liquid to about one-tenth the original volume of the bile/ethanol solution;

(h) dialyzing the aqueous phase in a dilute buffer solution having a pH of about 7.0 to about 8.56; and (i) subjecting said dialyzed aqueous phase to a reversed phase HPLC column to obtain a substantially pure and consistently potent composition which has a consistently reproducible pattern on reverse-phase HPLC where peaks are seen early in the exclusion fraction of about 27 and 32 minutes; said composition consisting of:

small molecular weight components of less than 3000 daltons in a buffered salt solution having a pH of about 7.0 to about 8.56, not more than 10 ppm ethanol and not more than 5 ppm either, and no measurable levels of IL-1$a$, IL-1$b$, TNF, IL-6, IL-8, IL-4, GM-CSF, or IFN-gamma, wherein said composition is capable of stimulating monocytes and/or macrophages in vitro, is capable of modulating tumor necrosis factor production, shows no cytotoxicity to human peripheral blood mononuclear cells, and is not an endotoxin, and wherein the composition has a finished fill volume of about 3 mL and has a biological activity of about 2.5 × compared to manufacturing processes resulting in about a 7.5 mL dosage fill volume.

19. A composition for use as an immunomodulator prepared by a process comprising:

(a) mixing bovine bile with an equal amount of ethanol to produce a bile/ethanol solution;

(b) separating out ethanol by centrifuging said bile/ethanol solution at 3000–5000 RPM for at least 2 hours at about 15–25° C. and heating to a temperature of about 80–85° C. for up to about 10 hours to obtain a solution substantially free of ethanol;

(c) removing bile pigments from the solution by using activated charcoal to obtain a colorless liquid;

(d) concentrating the colorless liquid to about one-eight the original volume of the bile/ethanol solution by heating the colorless liquid to a temperature of less than about 85° C.;

(e) conducting an ethyl ether extraction on the colorless liquid to obtain an aqueous phase;

(f) removing residual ether from the aqueous phase by heating the solution up to 55° C. for about 5–15 hours;

(g) adjusting the osmolarity of the aqueous phase so that the aqueous phase is hyperosmolar;

(h) concentrating the aqueous phase to about one-tenth the original volume of the bile/ethanol solution by heating the aqueous phase to a temperature of about 80–85° C.;

(i) dialyzing the aqueous phase in a dilute buffer solution obtained using dibasic and monobasic sodium salts as buffers and having a pH of about 7.0 to about 8.56;

(j) eluting components responsible for the release of TNF from PBMM from the dialyzed aqueous phase by passing the dialyzed aqueous phase through a reversed phase HPLC column so that peaks are provided at about 27 and 32 minutes; and (k) precipitating the TNF-releasing components and GM-CSF components by 80% acetonitrile;

wherein the release of TNF and the release of GM-CSF have a release ratio of about 2:1;

said composition consisting of:

small molecular weight components of less than 3000 daltons in a buffered salt solution having a pH of about 7.0 to about 8.56, not more than 10 ppm ethanol and not more than 5 ppm ether, and no measurable levels of IL-1a, IL-1b, TNF, IL-6, IL-8, IL-4, GM-CSF, or IFN-gamma; said composition containing about 15–21 mg/ml solids and about 720–880 µg/ml amino acids wherein less than 1% of the solids is organic material, there are no lipids in the solids, around half of the solids are carbohydrates, and the rest of the solids are peptides and amino acids selected from the group consisting of glutamate/glutamine, glycine, asparagine, threonine, serine, alanine, ninhydrin positive residues, and mixtures thereof; wherein said composition is capable of stimulating monocytes and/or macrophages in vitro, is capable of modulating tumor necrosis factor production, shows no cytotoxicity to human peripheral blood mononuclear cells, and is not an endotoxin, and wherein the composition has a finished fill volume of about 3 mL and has a biological activity of about 2.5 × compared to manufacturing processes resulting in about a 7.5 mL dosage fill volume.

20. A method of stimulating a patient's immune system comprising administering to said patient an effective amount of the composition of claim 1.

* * * * *

UNITED STATES PATENT AND TRADEMARK OFFICE
CERTIFICATE OF CORRECTION

PATENT NO.    : 6,551,623 B1
DATED         : April 22, 2003
INVENTOR(S)   : Rang It is certified that error appears in the above-identified patent and that said Letters Patent is hereby corrected as shown below:

<u>Column 68,</u>
Line 36, after "not more than 5 ppm" and before "and no", please replace "either" with -- ether --.

<u>Column 69,</u>
Line 10, after "from" and before "from the dialyzed aqueous phase", please replace "PBMM" with -- PBMN --.

Signed and Sealed this

Tenth Day of June, 2003

JAMES E. ROGAN
*Director of the United States Patent and Trademark Office*